(12) United States Patent
Tillim

(10) Patent No.: US 7,010,835 B2
(45) Date of Patent: Mar. 14, 2006

(54) PARALLEL HANDLE SYSTEM AND METHOD FOR DESIGNING A PARALLEL HANDLE SYSTEM

(76) Inventor: Stephen L. Tillim, 11730 Magdalena Ave., Los Altos, CA (US) 94024

( * ) Notice: Subject to any disclaimer, the term of this patent is extended or adjusted under 35 U.S.C. 154(b) by 0 days.

(21) Appl. No.: 10/692,340

(22) Filed: Oct. 24, 2003

(65) Prior Publication Data
US 2004/0088827 A1    May 13, 2004

Related U.S. Application Data

(63) Continuation-in-part of application No. 10/279,111, filed on Oct. 24, 2002, and a continuation-in-part of application No. PCT/US02/33956, filed on Oct. 24, 2002.

(60) Provisional application No. 60/330,527, filed on Oct. 24, 2001.

(51) Int. Cl.
*B25G 1/04* (2006.01)
*A45C 13/26* (2006.01)

(52) U.S. Cl. .................. 16/430; 16/110.1; 16/DIG. 12

(58) Field of Classification Search .................. 16/430, 16/431, 421, DIG. 12; 15/143.1, 145, 160, 15/257.5, 257.76; 30/232, 295, 308, 340, 30/341; 33/1 G, 510–512, 514.2; 74/551.1, 74/551.9, 553, 557; 81/177.1, 177.8, 124.5, 81/489; 173/162.1, 162.2, 169, 170; 482/47, 482/49, 44, 128; 280/821; 473/203, 526; 606/205–210; D8/303, 313, DIG. 1, DIG. 6–7, D8/61, 68, 80, 107; D7/649; D22/118
See application file for complete search history.

(56) References Cited

U.S. PATENT DOCUMENTS

| | | |
|---|---|---|
| 288,096 A | 11/1883 | Morgan |
| 336,540 A | 2/1886 | Wyttenbach |
| 340,382 A | 4/1886 | Smith |
| 700,492 A | 5/1902 | Henstock |
| 825,985 A | 7/1906 | Schwertenberg |
| 987,095 A | 3/1911 | Bonta |
| D43,242 S | 11/1912 | Bernstein |
| 1,188,394 A | 6/1916 | Bernstein |
| 1,229,658 A | 6/1917 | Sandow |
| 1,648,354 A | 11/1927 | Lied |

(Continued)

OTHER PUBLICATIONS

"Grotenhuis Endoscopic Fenestration System developed in cooperation with J. A. Grotenhuis, M.D.," Synergetics, Inc., 1998, one page.

(Continued)

*Primary Examiner*—Chuck Y. Mah
(74) *Attorney, Agent, or Firm*—Reed Smith LLP; Stanley P. Fisher, Esq.; Juan Carlos A. Marquez, Esq.

(57) ABSTRACT

A parallel handle, parallel handle system and method for designing parallel handles for a hand for use with tools or control mechanisms, that includes a handle having a radial section having a side for receiving the thumb and having a side for receiving the index finger, the radial section having a surface for engaging a portion of the palmar surface of the hand, a middle section having a side for receiving at least a portion of the middle finger and at least a portion of the ring finger and having a surface that avoids placing undue pressure on a surface of the hand located over the carpal tunnel, and an ulnar section having a side for receiving the small finger and having a surface for engaging a portion of the palmar surface of the hand so as to position the end of the small finger.

106 Claims, 25 Drawing Sheets

U.S. PATENT DOCUMENTS

| | | |
|---|---|---|
| 1,879,456 A | 9/1932 | Parsons |
| 1,919,968 A | 7/1933 | Trabold |
| 2,047,635 A | 7/1936 | Johst |
| 2,370,026 A | 2/1945 | Elia |
| 2,540,255 A | 2/1951 | Graves |
| 2,561,941 A | 7/1951 | Moskowitz |
| 2,621,688 A | 12/1952 | Wales |
| 2,669,991 A | 2/1954 | Curutchet |
| 2,669,993 A | 2/1954 | Curutchet |
| 2,975,505 A | 3/1961 | Linskey et al. |
| 3,129,939 A | 4/1964 | Stock |
| 3,407,816 A | 10/1968 | Curutchet |
| 3,557,792 A | 1/1971 | Rubin |
| 3,713,350 A | 1/1973 | Brilando |
| 3,741,665 A | 6/1973 | Smagala-Romanoff |
| 3,972,333 A | 8/1976 | Leveen |
| 4,043,343 A | 8/1977 | Williams |
| 4,127,338 A | 11/1978 | Laybourne |
| 4,161,051 A | 7/1979 | Brodwin |
| 4,413,034 A | 11/1983 | Anderson |
| 4,462,404 A | 7/1984 | Schwarz et al. |
| 4,553,746 A | 11/1985 | Lee |
| 4,572,227 A | 2/1986 | Wheeler |
| 4,599,915 A | 7/1986 | Hlavac et al. |
| 4,599,920 A | 7/1986 | Schmid |
| 4,632,383 A | 12/1986 | Tsuzuki |
| 4,641,857 A | 2/1987 | Gailiunas |
| 4,644,651 A | 2/1987 | Jacobsen |
| 4,674,330 A | 6/1987 | Ellis |
| 4,674,501 A | 6/1987 | Greenberg |
| D292,297 S | 10/1987 | Bingham |
| 4,738,158 A | 4/1988 | Christol |
| 4,785,495 A | 11/1988 | Dellis |
| 4,798,377 A | 1/1989 | White |
| 4,802,704 A | 2/1989 | Burns |
| 4,830,002 A | 5/1989 | Semm |
| 4,850,355 A | 7/1989 | Brooks et al. |
| 4,877,280 A | 10/1989 | Milano |
| 4,885,818 A | 12/1989 | Arterbury |
| 4,899,618 A | 2/1990 | Christol |
| 4,924,851 A | 5/1990 | Ognier et al. |
| 4,941,460 A | 7/1990 | Working |
| 4,962,747 A | 10/1990 | Biller |
| 5,002,561 A | 3/1991 | Fisher |
| 5,005,674 A | 4/1991 | Piatt |
| 5,024,119 A | 6/1991 | Linden |
| 5,031,640 A | 7/1991 | Spitzer |
| 5,044,058 A | 9/1991 | Voss |
| 5,046,381 A | 9/1991 | Mueller |
| 5,046,722 A | 9/1991 | Antoon |
| 5,047,046 A | 9/1991 | Bodoia |
| 5,047,049 A | 9/1991 | Salai |
| 5,076,569 A | 12/1991 | Gootter |
| 5,125,878 A | 6/1992 | Wingate et al. |
| 5,143,463 A | 9/1992 | Pozil et al. |
| 5,146,809 A | 9/1992 | Ruana |
| 5,146,810 A | 9/1992 | Mueller |
| 5,147,380 A | 9/1992 | Hernandez et al. |
| 5,159,851 A | 11/1992 | Rahmes |
| 5,160,343 A | 11/1992 | Brancel et al. |
| 5,176,696 A | 1/1993 | Saunders |
| 5,184,625 A | 2/1993 | Cottone, Jr. et al. |
| 5,199,324 A | 4/1993 | Sain |
| 5,211,655 A | 5/1993 | Hasson |
| 5,230,704 A | 7/1993 | Moberg et al. |
| 5,234,460 A | 8/1993 | Stouder, Jr. |
| D339,468 S | 9/1993 | Mertz |
| 5,277,683 A | 1/1994 | Wilkins |
| 5,299,991 A | 4/1994 | Sato |
| 5,318,589 A | 6/1994 | Lichtman |
| 5,339,850 A | 8/1994 | Mertz |
| 5,351,702 A | 10/1994 | Denjean |
| 5,366,476 A | 11/1994 | Noda |
| 5,379,758 A | 1/1995 | Snyder |
| 5,391,010 A | 2/1995 | Gorbunov |
| 5,417,234 A | 5/1995 | Davis |
| 5,445,479 A | 8/1995 | Hillinger |
| 5,454,380 A | 10/1995 | Gates |
| 5,470,162 A | 11/1995 | Rubin |
| 5,470,328 A | 11/1995 | Furnish et al. |
| 5,495,867 A | 3/1996 | Block |
| 5,498,256 A | 3/1996 | Furnish |
| 5,522,290 A | 6/1996 | Visser et al. |
| 5,540,304 A | 7/1996 | Hawkins et al. |
| 5,554,132 A | 9/1996 | Straits et al. |
| 5,556,092 A | 9/1996 | Theken |
| 5,562,693 A | 10/1996 | Devlin et al. |
| 5,571,127 A | 11/1996 | DeCampli |
| 5,578,050 A | 11/1996 | Webb |
| 5,606,985 A | 3/1997 | Battiston et al. |
| 5,634,382 A | 6/1997 | Fan |
| 5,653,713 A | 8/1997 | Michelson |
| 5,659,959 A | 8/1997 | Parlowski |
| 5,660,082 A | 8/1997 | Hsieh |
| 5,662,006 A | 9/1997 | Angeltun |
| 5,692,265 A | 12/1997 | Dalury |
| 5,728,121 A | 3/1998 | Bimbo et al. |
| 5,730,751 A | 3/1998 | Dillon et al. |
| 5,735,873 A | 4/1998 | MacLean |
| 5,761,767 A | 6/1998 | Barton |
| 5,782,853 A | 7/1998 | Zeevi et al. |
| 5,785,443 A | 7/1998 | Rubin |
| 5,791,671 A | 8/1998 | Tang et al. |
| 5,797,165 A | 8/1998 | Armbrust |
| 5,797,900 A | 8/1998 | Madhani et al. |
| 5,827,263 A | 10/1998 | Furnish et al. |
| 5,829,099 A | 11/1998 | Kopelman et al. |
| 5,830,231 A | 11/1998 | Geiges, Jr. |
| 5,833,580 A | 11/1998 | Chiu |
| 5,846,221 A | 12/1998 | Snoke et al. |
| 5,885,018 A | 3/1999 | Sato |
| 5,893,877 A | 4/1999 | Gampp, Jr. et al. |
| 5,897,571 A | 4/1999 | Kazama |
| 5,908,432 A | 6/1999 | Pan |
| 5,920,944 A | 7/1999 | Biggs et al. |
| 5,923,467 A | 7/1999 | Pericic et al. |
| 5,935,149 A | 8/1999 | Ek |
| 5,961,430 A | 10/1999 | Zuckerman et al. |
| 5,976,121 A | 11/1999 | Matern et al. |
| 5,979,015 A | 11/1999 | Tamaribuchi |
| 5,980,511 A | 11/1999 | Bilitz et al. |
| 5,991,956 A | 11/1999 | Chapman |
| 6,007,570 A | 12/1999 | Sharkey et al. |
| 6,012,623 A | 1/2000 | Fealey |
| 6,024,737 A | 2/2000 | Morales |
| 6,029,780 A | 2/2000 | Phillips |
| 6,030,409 A | 2/2000 | Lang |
| 6,041,258 A | 3/2000 | Cigaina et al. |
| 6,042,559 A | 3/2000 | Dobak, III |
| 6,063,087 A | 5/2000 | Agee et al. |
| 6,079,523 A | 6/2000 | Irvine |
| 6,085,611 A | 7/2000 | Valdez |
| 6,094,780 A | 8/2000 | McGlothlin et al. |
| 6,119,309 A | 9/2000 | Lu |
| 6,129,622 A | 10/2000 | Seaman et al. |
| 6,129,740 A | 10/2000 | Michelson |
| 6,134,994 A | 10/2000 | Gomas |
| 6,145,151 A | 11/2000 | Herron et al. |
| 6,161,256 A | 12/2000 | Quiring et al. |
| 6,161,974 A | 12/2000 | Nakagawa |
| 6,217,536 B1 | 4/2001 | Gustafson |
| 6,305,244 B1 | 10/2001 | Takahama |
| 6,354,618 B1 | 3/2002 | Liao |
| 6,427,565 B1 | 8/2002 | Ping |

| | | |
|---|---|---|
| 6,530,125 B1 | 3/2003 | Shippert |
| 6,592,160 B1 | 7/2003 | Nicolay et al. |
| 6,637,962 B1 | 10/2003 | Roche et al. |
| 2001/0001630 A1 | 5/2001 | Nakagawa |

OTHER PUBLICATIONS

"Reverse Cut Diamond Arachnoid Knife developed with James E. Benecke, M.D.," Synergetics, Inc., 1996, one page.

"Deep Neuro Dissection Set," Synergetics, Inc., 1996, two pages.

"Dacey TruMicro Vertical Scissors," Synergetics, Inc., 1998, four pages.

"Skull Base Instruments developed with James E. Benecke, M.D.", Synergetics, Inc., 1996, two pages.

"Spetzler TruMicro Scissors," Synergetics, Inc., 1998, two pages.

"Spetzler TruMicro Pituitary & Micro Cup Forceps," Synergetics, Inc., 1998, two pages.

"Spetzler Microsurgical Set," Synergetics, Inc., 1999, one page.

"Dacey Microvascular Repair Instruments developed in cooperation with Ralph G. Dacey, Jr., M.D.," Synergetics, Inc., 1996, two pages.

Photocopy of Carpal Lock, 2000, one page, Working, U.S. Patent 4,941,460.

Splints, Dynamic Splints, Hand Splints, AliMed Catalog, 2000, pp. D25, D26, D29 and D30.

Web site brochure for Ergo Pen, 1999, five pages, www.ergopen.com/ergopen/contact.html.

Steering Wheels and Quick Release Hubs, Pegasus Catalog, 2000, p. 107.

"Guide to the 2000 SAP United States Grand Prix", Road & Track, 2000, cover pages, pp. 16 & 18, three advertisement pages for Ferrari, Kumo tires, and Suzuki.

Illustration of hammer in article entitled "Quake insurance is less of a bargain but it's still a good investment", San Jose Magazine, 2001, two pages.

"Carpal Tunnel Syndrome Strike Many, Easy to Treat", Americal Association of Neurological Surgeons, 2000, one page.

Results of EAST patent search, re: Ergonomics, 2 pages, search performed in 2000.

Results of EAST patent search re: Medical Instruments, 15 pages, search performed in 2000.

Results of EAST patent search re: Pen, 1 page, search performed in 2000.

Result of Assignee patent search re: Synergetics patents, 2 pages, search performed in 2000.

"Hand Grip to Prevent and Alleviate Carpal Tunnel Syndrome", USPTO Disclosure Document No. 321372, filed Dec. 4, 1992, 3 pages and 1 page form PTOL-362.

Result of Patent Search on "parallel grip" on USPTO website.

"Jamar Dynamometer", North Coast Medical, Inc., San Jose, CA 95125.

International Search Report dated Jul. 14, 2004.

International Search Report dated Nov. 29, 2004.

International Search Report dated Feb. 28, 2005.

Photocopy illustration of known prior art rongeur.

FIG. 10L1    FIG. 10L2

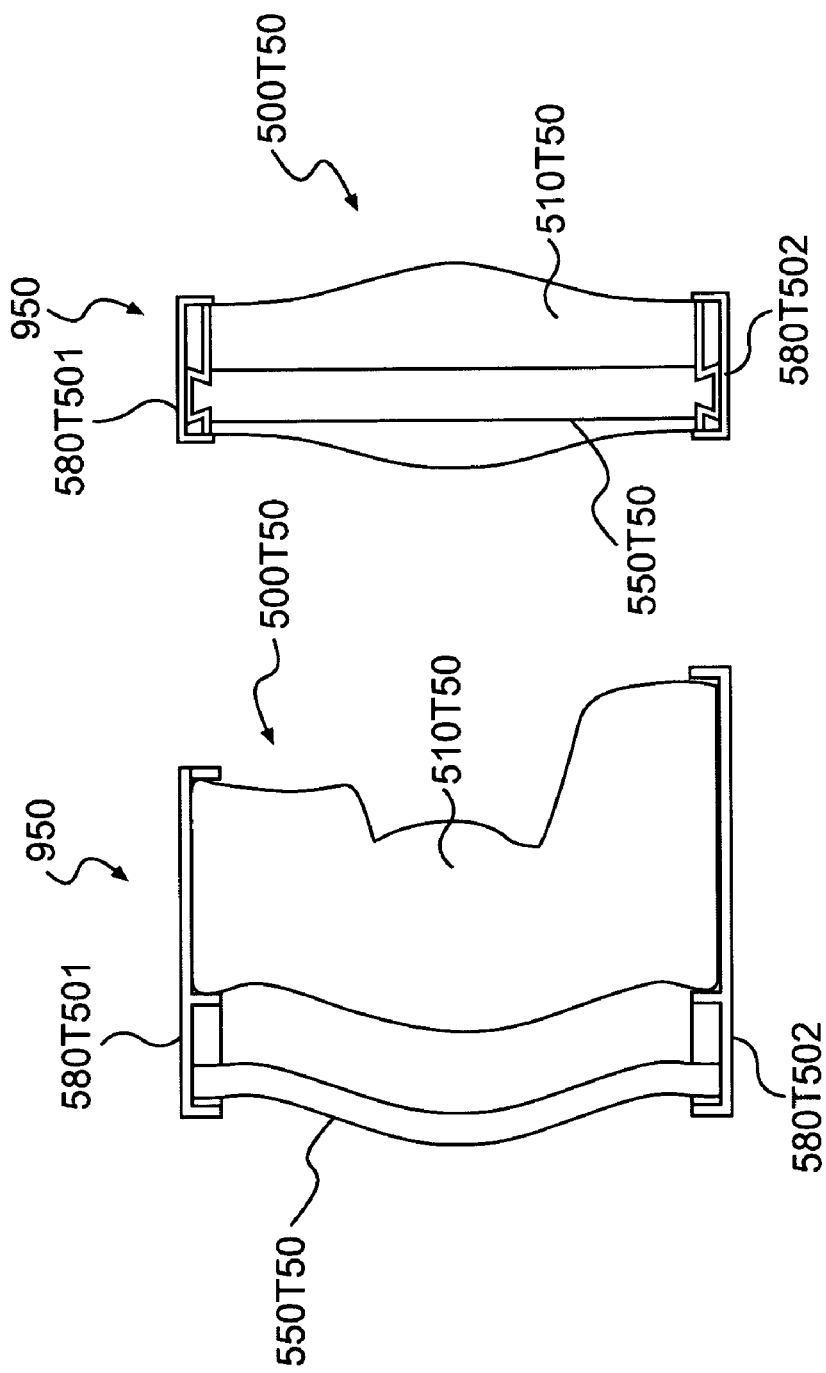

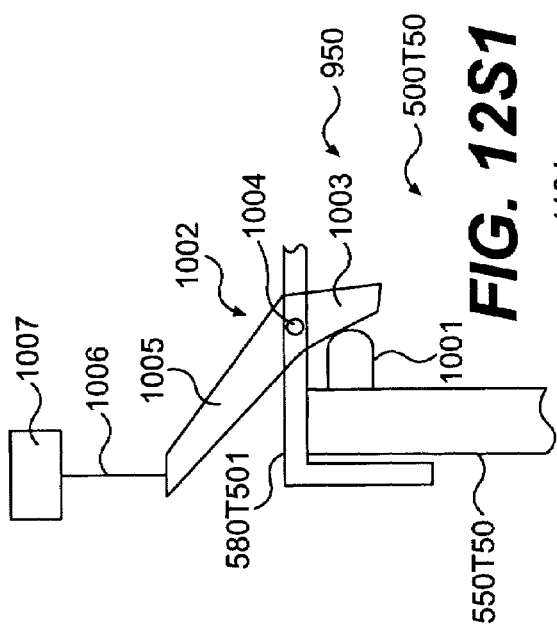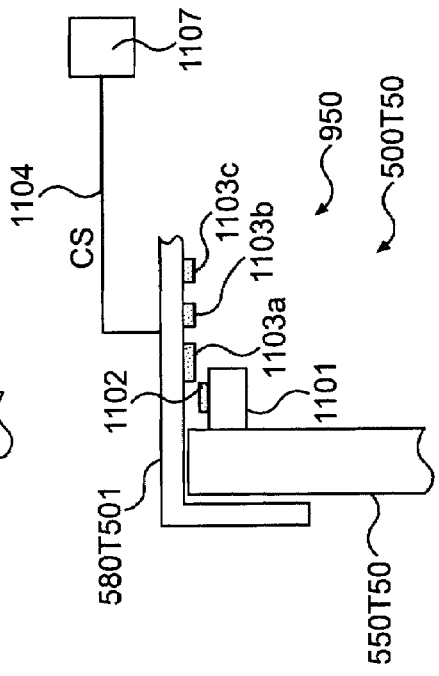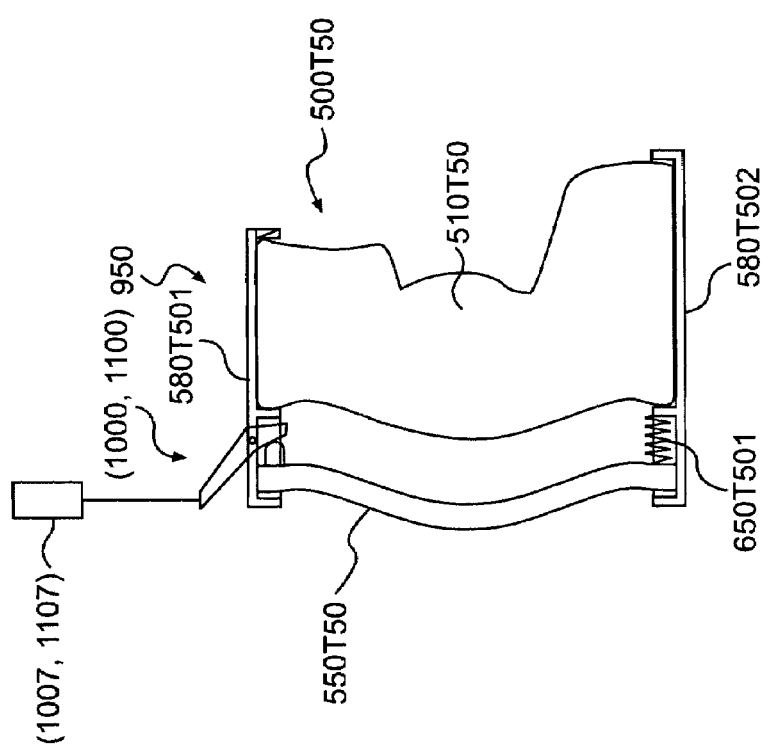

PARALLEL HANDLE SYSTEM AND METHOD FOR DESIGNING A PARALLEL HANDLE SYSTEM

CLAIM FOR PRIORITY

This application is a Continuation-in-Part of Non-Provisional Application Ser. No. 10/279,111 filed Oct. 24, 2002. Priority is claimed based on U.S. Application Ser. No. 10/279,111 and is a continuation-in-part of PCT Application No. PCT/US02/33956, both filed Oct. 24, 2002, which claims the priority of the corresponding U.S. Provisional Application No. 60/330,527 with the filing date of Oct. 24, 2001.

FIELD OF INVENTION

The present invention relates to parallel handles, parallel handle systems and methods for designing a parallel handle system for a hand for use in hold or using tools, such as those that hold, grip, cut and bite objects. The present invention also relates a parallel handle and parallel handle systems for use with control mechanisms for control of various devices and functions.

BACKGROUND OF THE INVENTION

Originally, known as pincers and used to handle hot coals, pliers are an ancient invention of hand tools that hold, grip, cut and bite objects. Pliers have two members, joined side by side on an axis and rotate relative to each other. The joint of a pliers allows each member to lever against the other and enhances the force at the working end while the handle section is moved. The joint can be a hinge joint, as used in standard pliers, or a pivot joint as in common scissors. The working end of the members can be generally short as in pliers or generally long as in scissors. The length of the handle depends on the amount of leverage needed to produce a force at the working end. The pliers handle is longer than the working end and the scissors handle is shorter than the working end. Pliers and other hinged tools are based on a triangular hinged system in which the apex is the hinge while the floor is open and the working end is attached to the apex.

As a hand grips an object the long fingers pull it to the center and/or the proximal part of the palm of the hand. Each long finger has three joints that allow a range of finger positions. The joints between the metacarpal bones of the hand and the proximal bones of the long fingers of the hand are called the metacarpal phalangeal (MP) joints. The proximal end of the MP joints lie at the horizontal creases in the palm. The joints between the proximal finger bone and second or middle finger bone of the long fingers are called the proximal interphalangeal (PIP) joints. The joints between the middle bones and end or distal finger bones are called the distal interphalangeal (DIP) joints.

When the hand is flat the extensor muscles of the forearm contract to extend the joints of the long fingers. When extensor muscles relax the hand changes from extension to the neutral or resting position. The muscular forces of extension and flexion of the forearm muscles are balanced and all the joints in the hand are partially flexed or bent. When the long fingers of the hand simultaneously flex to pull an object toward the palm the angle of each joint is related to anatomical and physiologic factors including the length of the individual finger bones and muscle contraction. Sequential joint flexion progressively closes the hand by decreasing the joint angles. When a fist is formed the long fingers flex and their fingertips align to touch the palm of the hand. If the fingertips touch the palm near the horizontal crease (distal part of the palm) then the angle formed at the PIP joints is smaller than the angle at the MP joints. However, if the fingertips touch the palm nearer to the wrist then the angle formed at the MP joints is smaller than the angle at the PIP joints. The significance of the angle of the long finger joint is related to whether the distal or middle part of the long fingers pulls an object. If the distal bones of the long fingers are pulling then the PIP joints have greater flexion and smaller angles. However, when the middle bones of the long fingers pull then the MP joints have smaller angles.

The hand adapts to the shape objects as it pulls them to the palm. Therefore, an object's shape determines which long finger bones and forearm flexor muscles that pull. For example, if the distal segments of the long fingers pull the flat side of an object all sections of the forearm's deep flexor muscle contract. When the middle bones of the long fingers pull the convex side of a flat object, all sections of the forearm's superficial flexor muscle contract. In both cases, the pull is symmetric across similar bones of the long fingers and one muscle group is used. However, if the object being gripped is round, like a cylinder, then similar segments of the long fingers do not pull. Furthermore, the muscle sections used to pull the bone segments of the fingers are asymmetric. For example, a cylinder is gripped with the distal segment of the index finger, the middle segments of the middle finger and the ring finger along and the distal segment of the small finger. The tendons of the middle sections of the contracting superficial forearm muscle pull the middle finger segments of the middle and ring fingers. Whereas, The tendons of the outside sections of the contracting deep forearm muscle pull the distal segments of the index and ring fingers. Thus, these asymmetric muscle groups pull non-similar tendons from both the superficial and deep flexor muscles of the forearm to pull the bones. Of note, the tendons pulling the middle segments of the middle and ring fingers are adjacent to the median nerve. Pulling these tendons provokes compression and pressure on the median nerve in the carpal tunnel (CT).

When viewing the palm of the flat hand from the wrist the thenar eminence lies above the hypothenar eminence. The difference increases when the thumb opposes the long fingers. When the thumb opposes the long fingers and an object, like a cylinder, is pulled toward the proximal part of the palm it first contacts the thenar eminence. Then the object tilts toward the hypothenar eminence as the ring finger and the small finger flex further to increase grip. The added grip moves tips of the ring finger and small finger closer to the palm and out of alignment with the ends of the index finger and middle finger. This can produce discomfort in the wrist as the flexor tendons of the ring and small finger move in the CT against the transverse carpal ligament (TCL) and median nerve. The discomfort is enhanced when the space in the CT is small or is compromised by repetitive wrist injury.

As discussed above, pliers are hand tools based on the triangular lever system and combine two members at an axis of rotation or hinge. The handle members of pliers are commonly convex or straight. Like a lever, one handle member can be fixed and the other moves or both handle can move. The fixed handle member can be considered held in place where it touches the thenar eminence and the hypothenar eminence at the proximal part of the palm of the hand. Long finger flexion advances moving handle member toward the fixed member to close the working end. However, both handle members can be moved toward each other from the hinge.

The working end of common pliers is usually held near the radial side of the hand and the free end of pliers' handles rests near the ulnar side of the hand. The palm holds the proximal handle and the long fingers hold the distal handle. The free end of pliers' handles is spread to open the working end. Actuating the working end of the common pliers involves reaching with the distal segment of the small finger and the distal segment of the ring finger on the ulnar side of the hand to pull the distal handle member. Next, the middle bones of the middle finger and the index finger of the long fingers of the hand advance to pull the distal handle member of the pliers. Simultaneously, the ring finger and small finger advance so their middle bones also pull the distal handle member of the pliers. This progression is related to the distance required for the long fingers to reach the distal handle member because of the hinge. The triangular hinged system forces the smallest and weakest sections of the forearm flexor muscles for small finger and ring finger to squeeze the pliers handle.

There are reasons that many people have hand and wrist problems from repetitive use of common pliers. The wide free end makes for longer reach and harder work for the ring finger and small finger. By design, common pliers have concave or straight handles. This causes the proximal member to press into the CT area of the palm of the hand and transmits pressure to the transverse carpal ligament (TCL) and the underlying median nerve. Joint and ligament stress is present at the MP joints when the long fingers of the hand reach off center for the moving pliers handle. This is because the MP joints have limited side motion and the long fingers are forced to deviate in the radial direction to reach and grasp the moving handle. Such stresses from the long fingers deviating at the MP joints can cause a problem. Furthermore, common pliers are sometimes clumsy to use and are not made for single-handed operation. It takes one hand to stabilize while the other spreads the handles apart adding time to tasks.

DESCRIPTION OF THE RELATED ART

Lever systems are used for a range tools and implements to magnify closing force at the jaws. The range of hand tools and implements integrating hinges with levers is numerous. Among levered hinged implements the hand uses are pliers, cutting tools, hand brake and clutch controls and surgical instruments. Applications for levered hinges include various hand tools, bicycles, motorcycles and many others. Levers with hinges are used in surgical instruments with various bone rongeurs using gross motor function and endoscopic instruments requiring fine motor skills.

Among many examples of handles for hand tools based on movement at a levered hinge noted in the art include patents U.S. Pat. No. 6,134,994 Pliers with Ergonomic Handles, U.S. Pat. No. 6,427,565 Parallel Grip Pliers and U.S. Pat. No. 6,129,622 Pair of Scissors for Cutting Shellfish. Other examples of hinged hand levers for bicycle brakes include patents U.S. Pat. No. 5,005,674 Bi-directional Rotating Grip Brake, U.S. Pat. No. 5,540,304 Single-handled Vehicle Brake System and U.S. Pat. No. 5,660,082 Adjustable Brake Control for A Bicycle. Aside from the common Kerrison rongeur and the Leksell double action bone rongeur an example of a surgical instrument handle using a hinge includes U.S. Pat. No. 6,129,740 Instrument Handle Design Discomfort and hand fatigue occurs with repetitive use of handles for tools with hinges based on the lever system. A previously injured hand has greater discomfort at the damaged areas than a normal hand. However, the repetitive use of such tools can result in disability for workers. The reasons include strain produced from obliging the small finger and ring finger initiate squeeze with the smallest and weakest sections of the forearm flexor muscles. Furthermore, the concave or flat handle design of the fixed member transmits pressure to the transverse carpal ligament (TCL) and the underlying median nerve. Discomfort can also occur in the wrist from squeezing, thus tightening the ring finger and small finger tendons, to increase the closing force of the jaws of such implements or tools. Such increased grip forces the tendons in the CT against the median nerve and TCL.

The Jaymar Dynamometer is one example of a common parallel handle incorporated in a device to measure grip strength. Another known parallel handle is illustrated in "Apparatus for Measurement of Grip and pinch Strength, U.S. Pat. No. 4,674,330. The handles in both of these devices place pressure in the valley of the palm between the thenar and hypothenar eminencies. Such pressure is directly over the TCL. The pressure produced in that area of the palm can cause discomfort and pain. Also such pressure on the TCL can limit the effectiveness and accuracy of a in the measurement of grip strength, such as when the wrist is injured.

Hand tools that hold, grip, cut and bite objects are in daily use. However, tools generally based on a triangular levered system typically may not comfortable. A system for hand tools efficiently using anatomical and physiological features of the fingers, hand and forearm is needed and would be more comfortable. A more efficient handle design would oblige the tips the long fingers to substantially end at a line, and promote the long fingers to form a cup. Such a handle would enable the divisions of one muscle to contract at the same time to initiate like parts of the long fingers to move across the handle's distal member. Such a handle would spread segmental long finger pull symmetrically across the distal member and result in a stronger grip.

Furthermore, the proximal member of such a handle would have an empty space so as not to touch or place pressure on the region of the CT. In addition, the proximal member would have an extension where it contacts the hypothenar area. This extension would prevent the ring finger and small finger from excessively forcing the proximal member of such a handle into the ulnar side of the hand. The result would be reduced median nerve compression and reduced pressure in the CT. This would decrease ligament and joint strain in the hand. A handle based on a parallel system with these features added to the distal member and the proximal member of a handle for pliers would require less effort to grip and be easier to use than a triangular levered handle.

SUMMARY OF THE INVENTION

The present invention relates to parallel handles, parallel handle systems and methods for designing a parallel handle system for a hand for use in hold or using tools, such as those that hold, grip, cut and bite objects. The present invention also relates a parallel handle and parallel handle systems for use with control mechanisms for control of various devices and functions. Such handles provide a hand to squeeze one member toward another member to apply force to a working end. Furthermore, the present invention provides a method and apparatus for designing such handles. Desirably, the handles have two generally parallel members designed to comfortably fit the hand as the members move toward each other. Furthermore, such a handle does not place pressure on the region of the carpal tunnel of the hand. In addition, the present invention provides systems that desirably connect both moving members. The parallel handle system of the present invention can be attached to various apparatuses to assist the hand in pinching, gripping, holding, cutting and other functions. The parallel handle system of the present invention can be used for a variety of surgical instruments, pliers and a variety of tools and instruments.

In this regard the present invention provides a handle or apparatus for use with the hand that includes: a radial section having a side for receiving the thumb of the hand and having a side for receiving the index finger of the hand, and the radial section having a surface for engaging a portion of the palmar surface of the hand; a middle section having a side for receiving at least a portion of the middle finger and at least a portion of the ring finger of the hand and having a surface that avoids placing undue pressure on a surface of the hand located over the carpal tunnel; and an ulnar section having a side for receiving the small finger of the hand and having a surface for engaging a portion of the palmar surface of the hand so as to position the end of the small finger.

Also, the present invention provides a method for designing a handle that corresponds to the sizes of a hand, that includes the steps of: setting the hand in a T position so that the tips of the of the long fingers of the hand are substantially in alignment; measuring the distance across the metacarpal bones of the long fingers of a hand from the radial side to the ulnar side of the palm of the hand thereby defining a width of the handle; and setting the distance from the ulnar palmar line to the distal side of the carpal tunnel zone equal to or less than the distance from the ulnar palmar line to the radial palmar line such that undue pressure on the carpal tunnel zone is avoided.

BRIEF DESCRIPTION OF THE DRAWINGS

The foregoing and additional features and characteristics of the present invention will become more apparent from the following detailed description considered with reference to the accompanying drawings in which like reference numerals designate like elements and wherein:

FIGS. 10A through 10M illustrate variations of a parallel handle of the present invention. With FIGS. 10A and 10B illustrating a parallel handle having guide members on the radial end and the ulnar end of the parallel handle. FIGS. 10C and 10D illustrating various connecting mechanisms related to the relationship of a guide member to the moving member. FIG. 10E illustrates a parallel handle with guide members that telescope and have coil springs in which the guide members are between the radial end and the ulnar end of a parallel handle. FIG. 10F has a track guide member and a telescoping guide member at the radial side of the parallel handle with a left spring between the moving members. FIG. 10G illustrates curved guide members at the radial end and the ulnar end of a parallel handle. FIG. 10H illustrates non-parallel guide members at radial end and ulnar ends of a parallel handle. FIG. 10I illustrates a guide member and a coil spring at the radial end and ring members allowing the thumb and long fingers to separate the moving members of a parallel handle. FIG. 10J illustrates replaceable members that can be attached to shafts to create proximal and distal moving members of various sizes with guide members at the radial end and the ulnar end of a parallel handle. FIG. 10K illustrates a locking type guide member and spring between radial end and ulnar ends of a parallel handle. FIGS. 10L1 and 10L2 illustrate narrow and wide working ends attached to moving members of a parallel handle. FIG. 10M illustrates stops that can be applied to guide members to limit travel of a parallel handle.

FIGS. 12A through 12S2 illustrate various embodiments for applications of a parallel handle of the present invention. FIGS. 12A illustrates an embodiment of a parallel handle of the present invention used as pliers. FIGS. 12N through 12S2 illustrate examples of a parallel handle control mechanism that incorporates a parallel handle of the present invention.

DESCRIPTION OF THE PREFERRED EMBODIMENTS

In order to more clearly and concisely describe the subject matter of the present invention, the following definition for the T Position, Spread T Position STP and Closed T Position CTP are intended to provide guidance as to the meanings of specific terms used in the following written description. In addition, it is to be understood that the phraseology or terminology employed herein is for the purpose of description, and not to be construed in a limiting sense. The following discussion relates to areas of the hand in relation to the present invention with reference to FIGS. 1 through 6.

Figure 1:
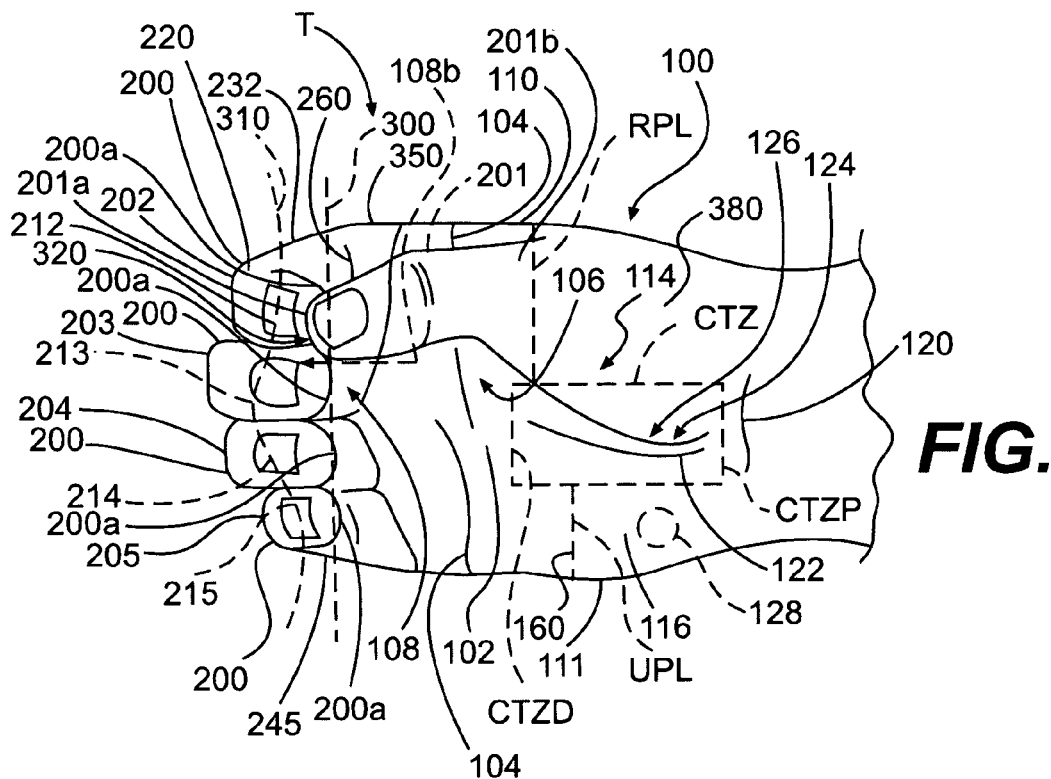
FIG. 1 is a view of the palmar side of the hand when the hand is in the T Position illustrating the long fingers ending in the same line and the thumb opposing the space between the index finger and middle finger.
Figure 2:
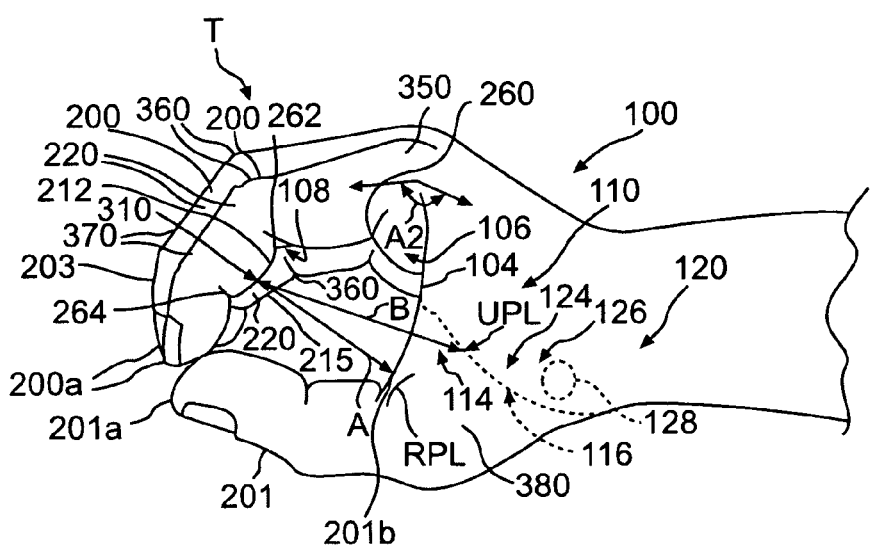
FIG. 2 is a view of the radial side of the hand when the hand is in the T Position illustrating the long fingers ending in the same line and the thumb opposing the space between the index finger and middle finger.

FIG. 1 is a view of the palm 102 of the hand 100 and FIG. 2 the radial side 110 of hand 100. FIG. 1 and FIG. 2 illustrate the hand 100 to the T Position.

The T Position is the position the hand 100 assumes when the tips 200a of the long fingers 200 are substantially aligned, line 300, and the tip 201a of the thumb 201 opposes the space 320 between the index finger 202 and middle finger 203. In the T Position the PIP joints 360 of the long fingers 200 lie adjacent to each other. The PIP joint 360 of the middle finger 203 is further away from line 300 than the PIP joints 360 of the other long fingers 200 of the hand 100. The PIP joint 360 of the small finger 205 is closer to line 300 than PIP joints 360 of the other long fingers 200. Furthermore, when the hand 100 is in the T Position the palmar surface 102 of the long fingers 200 form a cup 108 shown as curve 310. This finger cup 108 is the concave area formed across the long fingers 200 when the tips 200a of the long fingers 200 are substantially aligned at line 300 and the long fingers 200 are flexed.

When the hand is in the T position the area crossing the palm 102 of the hand 100 known as the palmar arch 106 is concave. The horizontal creases 104 of the palm 102 appear as a skin fold and align with the palmar arch 106. The thumb 201, illustrated in FIG. 1, hides the horizontal crease 104 on the radial side 110 of the hand 100. The longitudinal creases 122 also appear as a skin fold because the palm 102 of the hand 100 is not flat.

Continuing with reference to FIG. 1, the thenar muscle area 114 is on the radial side 110 of the hand 100 and radial to the CT 126. The hypothenar muscle area 116 is on the ulnar side 111 of the hand 100 and ulnar to the CT 126. The hypothenar muscle area 116 extends from the horizontal crease 104 of the ulnar side 111 of the hand 100 to the wrist 120 at the level of the pisiform bone 128. The pisiform bone 128 on the ulnar side 111 of the hand 100 is the location where the ulnar nerve and ulnar artery go under the hypothenar muscle area 116 in the palm 102 of the hand 100. The transverse carpal ligament (TCL) 124 covers the carpal tunnel (CT) 126. The CT 126 contains the median nerve, four tendons from the superficial flexor muscle of the forearm and four tendons from the deep flexor muscle of the forearm. The superficial tendons are closer to the inner surface of the TCL 124 than the deep tendons. This placing the superficial tendons next to the median nerve.

In addition, illustrated in FIG. 1 is an area of the hand, which can be called the "carpal tunnel zone" CTZ, where pressure and vibration is best avoided. The "carpal tunnel zone" CTZ contains the proximal and distal parts of the median nerve and the tendons to the long fingers 200 of the hand 100 that enter and leave the CT 126. The "carpal tunnel zone" CTZ extends proximally beyond the CT 126 toward the wrist 120 and distally toward the horizontal creases 104. The proximal end CTZP of the "carpal tunnel zone" CTZ ends at the wrist 120. The distal end CTZD of the "carpal tunnel zone" CTZ ends approximately one centimeter proximal to the horizontal creases 104 of the palm 102 of the hand 100.

Figure 3:
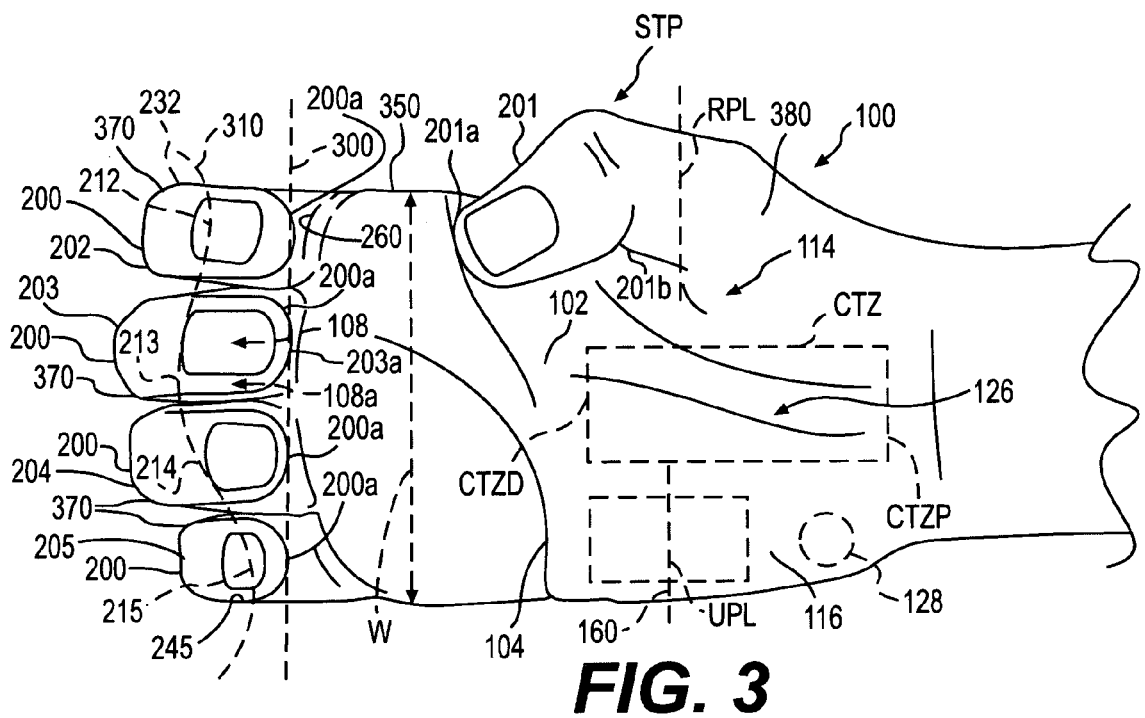
FIG. 3 is a view of the palmar side of the hand when the hand is in the Spread T Position illustrating the long fingers ending in the same line and the thumb opposing and spread apart from the tips of the long fingers.
Figure 5:
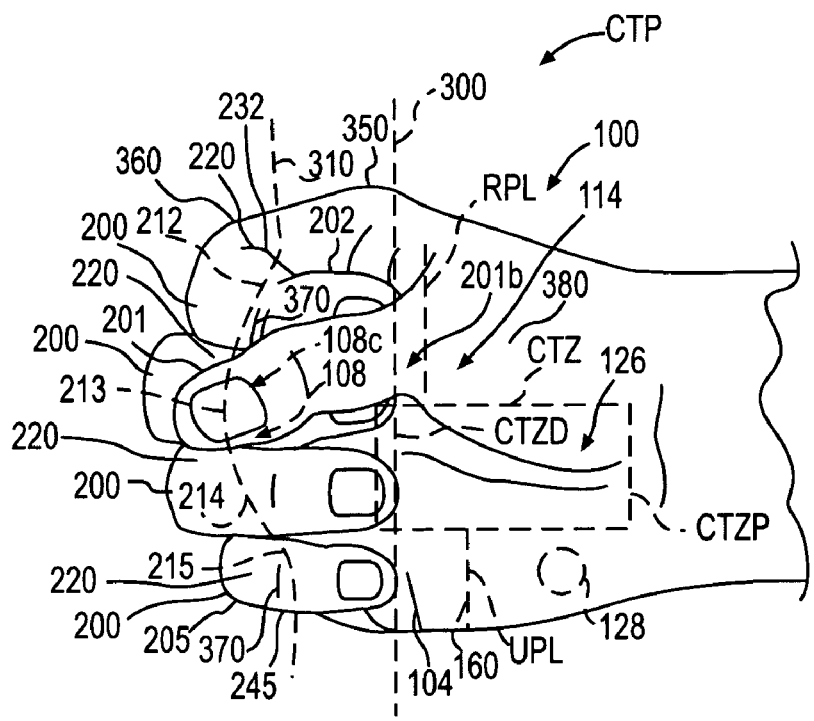
FIG. 5 is a view of the palmar side of the hand when the hand is in the Closed T Position illustrating the long fingers ending in the same line and the thumb overlapping the space between the index finger and middle finger.

As illustrated in FIG. 1, FIG. 3 and FIG. 5 the radial side CTZR of the "carpal touch zone" area CTZ meets the radial palmar line RPL and the ulnar side CTZU of the "carpal touch zone" area CTZ meets the ulnar palmar line UPL. The radial palmar line RPL crosses the thenar muscle area 114 of radial side 110 of the palm 102 of the hand 100 and defines the width of the radial side 100 of the hand 100. The ulnar palmar line UPL crosses the hypothenar muscle area 116 and defines the width of the ulnar side 111 of the hand 100.

The radial palmar line RPL starts at the radial side 110 of the base 201b of the thumb 201 and extends approximately 40% of the width W of the palm 102 of the hand 100 toward the "carpal tunnel zone" CTZ of the palm 102 of the hand 100. The ulnar palmar line UPL starts on the ulnar side 111 of the hand 100 and meets the ulnar side NTZU of the "carpal tunnel zone" CTZ. The ulnar palmar line UPL is located on the hypothenar muscle area 116 at approximately half the distance between the ulnar side 111 of the horizontal crease 104 of the palm 102 of the hand 100 and the pisiform bone 128 of the wrist 120. The ulnar palmar line UPL extends approximately 30% of the width W of the palm 102 of the hand 100. This leaves the relative width of the "no touch zone" area NTZ as approximately 30% of the central section of the palm 102 of the hand 100.

Figure 4:
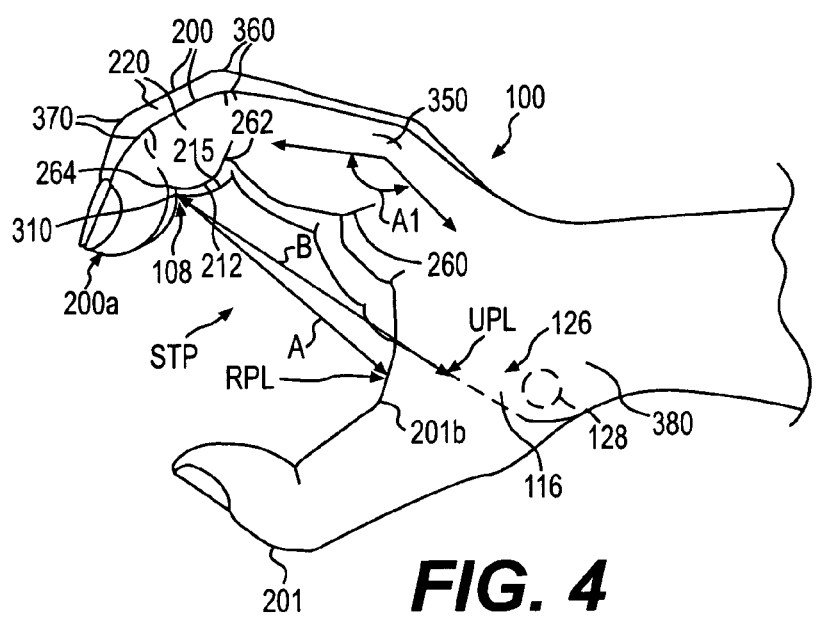
FIG. 4 is a view of the radial side of the hand when the hand is in the Spread T Position illustrating the long fingers ending in the same line and the thumb opposing the space between the index finger and middle finger.

FIG. 3 and FIG. 4 illustrate the hand 100 in the Spread T Position STP. In this variant of the T position the MP joints 350 of the long fingers 200 of the hand 100 are spread and the thumb 201 is abducted at the metacarpal (MC) joint 380 of the thumb. The tips 200a of the long fingers 200 of the hand 100 essentially remain substantially aligned at line 300. The curve 310 of the finger cup 108 is essentially the same whether the hand 100 is in the T Position or the Spread T Position STP. This occurs because the angles A1, A2 and A3 of the MP joints 350 of the long fingers 200 have no effect on the PIP joints 360 and DIP joints 370 when tips 200a of the long fingers 200 are substantially aligned.

FIG. 3 also shows the tip 201a of the thumb 201 appears directed toward the tip 203a of the middle finger 203 when the hand 100 in the Spread T Position STP. However, when the hand changes from the Spread T Position STP to the T Position, the thumb 201 moves at the MC joint 380 of the wrist 120 and the tip 201a of the thumb 201 opposes the space 320 between the index 202 finger and middle finger 203.

Figure 6:
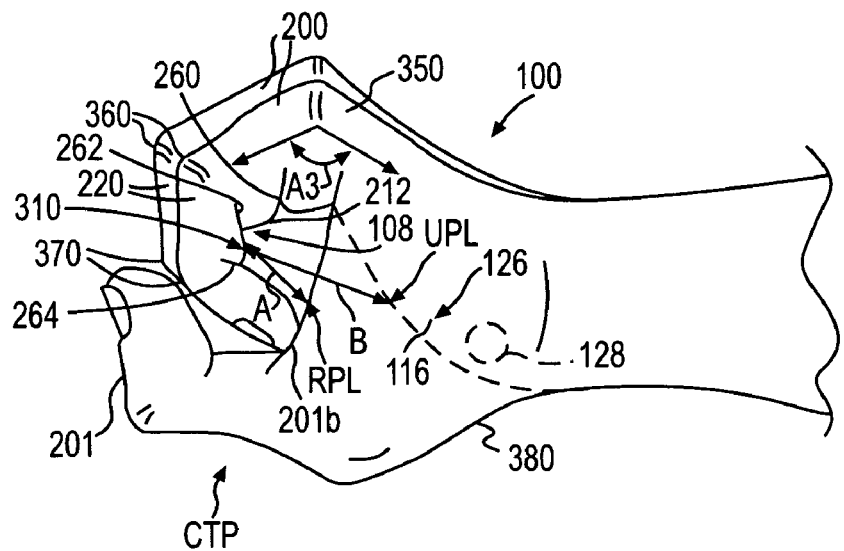
FIG. 6 is a view of the radial side of the hand when the hand is in the Closed T Position illustrating the long fingers ending in the same line and the thumb overlapping the space between the index finger and middle finger.

FIG. 5 and FIG. 6 illustrate the hand 100 in the Closed T Position CTP, which is a variant of the T position. The angle A3 at the MP joints 350 of the long fingers 200 of the hand 100 is narrow and the thumb 201 overlaps the middle finger 203. The tips 200a of the long fingers 200 of the hand 100 essentially remain substantially aligned at line 300. The curve 310 of the finger cup 108 is essentially the same whether the hand 100 is in the Closed T Position CTP, the T Position or the Spread T Position STP. Therefore, the curve 310 of the finger cup 108 is determined by the alignment of the tips 200a of the long fingers 200 of the hand 100 and not the flexion angle A1, A2 and A3 at the MP joints 350 of the long fingers 200.

FIG. 1, FIG. 2, FIG. 3, FIG. 4, FIG. 5 and FIG. 6 refer to the curve 310 of the finger cup 108. For purposes of the present application for a parallel handle system of the present invention, the curve 310 of the finger cup 108 is drawn across the inner surfaces 212, 213, 214, 215 of the middle segment 220 the long fingers 200 of the hand 100 when the hand 100 is positioned in the T Position, the Spread T Position STP and/or the Closed T Position CTP. The curve 310 of the finger cup 108 can be drawn on the inner surfaces 212, 213, 214, 215 of the long fingers 200 between the middle long finger creases 262 and the distal long finger creases 264. The curve of the finger cup 108 can be drawn starting either at the radial side 232 of the middle segment 220 of the index finger 201 or the ulnar side 245 of the middle segment 220 small finger 205. If the curve 310 of the finger cup 108 commences at any point along the radial side 232 of the middle segment 220 of the index finger 202 then it extends across the inner surface 212 of the index finger 202. The curve 310 of the finger cup 108 next crosses the inner surface 213 of the middle segment 220 of the middle finger 203 and extends to the inner surface 214 of the middle segment 220 of the ring finger 204. From the ring finger 204, the curve 310 of the finger cup 108 crosses the inner surface 215 of the middle segment 220 of the small finger 205 and ends along ulnar side 245 of the middle segment 220 of the small finger 205 of the hand 100.

The curve 310 of the finger cup 108 is related to the size, i.e. the width, length and depth of the bones of the hand 100 and flexion at the joints 350, 360, 370 of the long fingers 200 of the hand 100. The shape of the curve 310 of the finger cup 108 is similar for various hand sizes when drawn at the same location between the proximal finger creases 260 and distal finger creases 264 of the long fingers. The angles A1, A2, A3 of the MP joints 350 do not affect the curve 310 of the finger cup 108 as long as the tips 200a of the long fingers 200 end at line 300. Furthermore, the curve 310 of the finger cup 108, as illustrated in FIGS. 1, 3 and 5 is similar for hands 100 of different people when the hand 100 is in the T Position, Spread T Position STP or Closed T Position CTP.

The shape of the curve 310 of the finger cup 108 can be duplicated by placing a contour gauge across the middle segments 220 of the long fingers 200 of the hand 100 when the hand 100 is in the T Position. Such shape of the curve 310 of the finger cup 108 can generally resemble a sine curve when drawn on a graph.

Alternatively, the shape of the curve 310 of the finger cup 108 can be determined by measuring the distance of corresponding lines placed across the palm 102 parallel to line 300 and plotting the measured distance to the middle segments 220 of the long fingers 200 of the hand 100 which would fall on the curve 310. For example, the radial palmar line RPL in FIGS. 1, 3 and 5 can be such a line for determining the shape of the curve 310 if extended across the palm 102 of the hand 100.

The distances measured from corresponding lines extended from the radial palmar line RPL to the inner surfaces 213, 212, 214, 215 of the middle segments 220 of the middle finger 203, ring finger 394, index finger 202 and small finger 205 that would fall on the line 310 decrease progressively. FIGS. 1, 3 and 5 also illustrate the locations of the radial palmar line RPL and ulnar palmar line UPL for a hand 100 in the T Position, the Spread T Position STP and the Closed T Position CTP. FIGS. 2, 4 and 6 further illustrate the radial palmar line RPL and the ulnar palmar line UPL in profile as viewed from the radial side 110 of the hand 100 in the T Position in FIG. 2, the Spread T Position STP in FIG. 4 and the Closed T Position CTP in FIG. 6.

FIG. 2, FIG. 4 and FIG. 6 also illustrate the relationship of the radial palmar line RPL and the ulnar palmar line UPL to the middle segments 220 of the long fingers 200. The lines L1 and L2 in FIG. 2, the lines L3 and L4 in FIG. 4 and the lines L5 and L6 in FIG. 6 when drawn from the respective radial palmar line RPL and ulnar palmar line UPL to each of the respective middle segments 220 of the long fingers 200 can provide measurements that correspond to the shape of a parallel handle of the present invention based on the design method of the present invention for use when the hand is in the corresponding T Position, Spread T Position STP and Closed T Position CTP.

Furthermore, as shown FIGS. 1, 2, 5 and 6 the radial palmar line RPL is approximately at the same distance distal to the ulnar palmar line UPL whether the hand 100 is in the T Position or the Closed T Position CTP. However, as shown in FIG. 3, the radial palmar line RPL and ulnar palmar line UPL are almost aligned when the hand is in the Spread T Position STP when viewed from the palm 102. However, in the Spread T Position STP the opposing movement at the MC joint 380 of the thumb 201 places the radial palmar line RPL distal to the ulnar palmar line UPL as illustrated in FIG. 4. This is because the thenar muscle area 114 moves the base 201b of the thumb 201 while the hypothenar muscle area 116 remains in the same position. Also, as illustrated in FIG. 1, FIG. 2, FIG. 3, FIG. 4, FIG. 5 and FIG. 6 the distance from the curve 310 of the finger cup 108 across the middle segments 220 of the long fingers 200 to the ulnar palmar line UPL decreases progressively when measured when the hand 100 changes from the Spread T Position STP to the T Position to the Closed T Position CTP.

Figure 7:
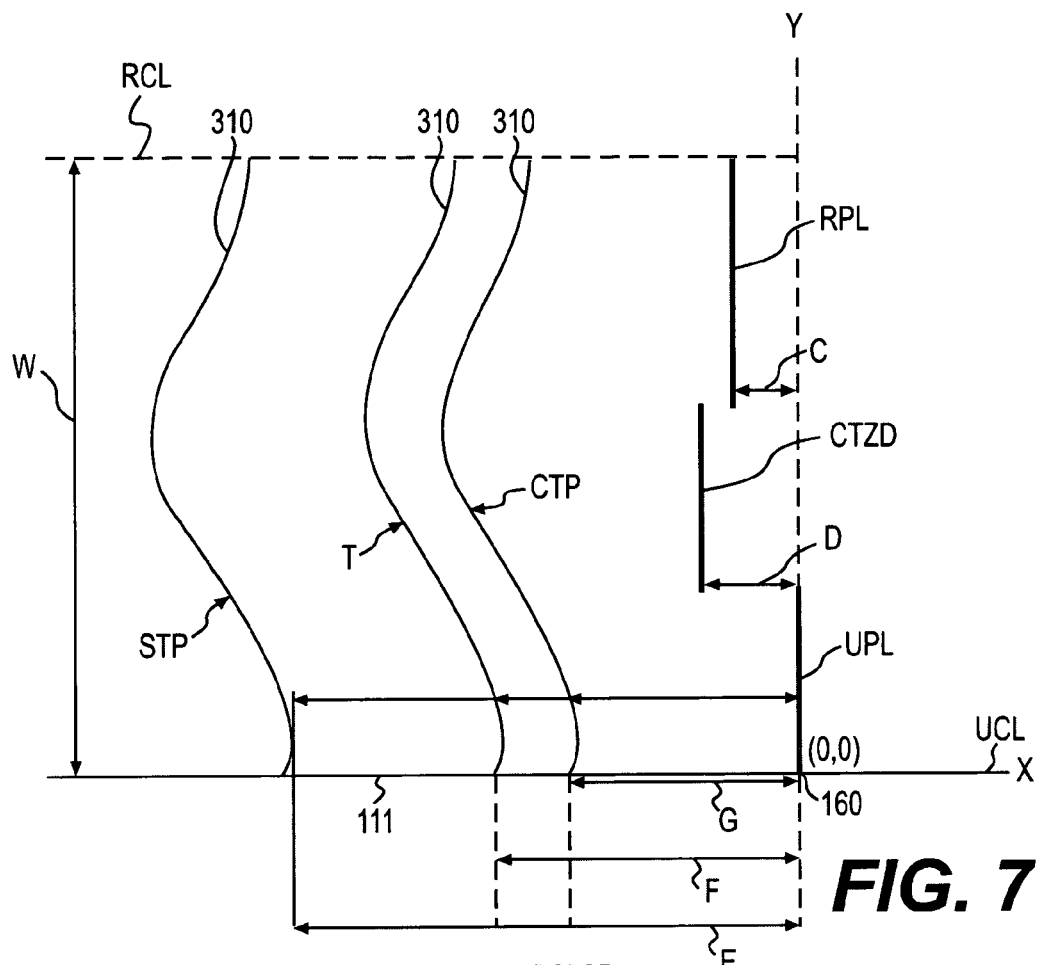
FIG. 7 is a graph representing the curves of the cup formed by the long fingers in the Spread T Position, T Position and Closed T Position in relation to described lines on the palm of the hand.

FIG. 7 illustrates a graph formatted for a right hand 100 to show the relationships of the curve 310 of the finger cup 108 for the respective Spread T Position STP, T Position and Closed T Position CTP in relation to the radial palmar line RPL, distal side CTZD of the "carpal tunnel zone" CTZ and the ulnar palmar line UPL. The zero point (0,0) for the X-axis and Y-axis is the origin of the ulnar side 160 of the ulnar palmar line UPL. The x-axis parallels the ulnar side 111 of the hand 100. Measurements for a hand 100 for the ulnar palmar line UPL, radial palmar line RPL, the distal side CTZD of the "carpal tunnel zone" CTZ can be plotted in the Y-axis direction as illustrated in FIG. 7.

Measurements for a hand 100 from the ulnar palmar line UPL to the distal side CTZD of the "carpal tunnel zone" CTZ, from the ulnar palmar line UPL to radial palmar line RPL, from the ulnar palmar line UPL to curve 310 of the finger cup 108c for a hand 100 in the Closed T Position CTP, from the ulnar palmar line UPL to curve 310 of the finger cup 108b for a hand 100 in the T Position and from the ulnar palmar line UPL to curve 310 for the finger cup 108a for a hand 100 in the Spread T Position STP can be plotted in the X-axis direction as illustrated in FIG. 7.

Continuing with reference to FIG. 7, Distance C is from the ulnar palmar line UPL to the radial palmar line RPL. Distance D extends from the ulnar palmar line UPL to the distal side CTZD of the "carpal tunnel zone" CTZ. Distance E is between the ulnar palmar line UPL to the curve 310 of the finger cup 108a when the hand is in the Spread T Position STP. Distance F spans the ulnar palmar line UPL to the curve of the finger cup 108b when the hand is in the T Position. Distance G is from the ulnar palmar line UPL to the curve of the finger cup 108c when the hand is in the Closed T Position CTP. Distance C, Distance D, Distance E, Distance F and Distance G are related to hand size and will be greater for larger hands 100. Reasonable approximations, for example, for an average hand 100, for Distance C is 1 centimeter, for Distance D is 1.5 centimeters, for Distance E is 7.5 centimeters, for Distance F is 5.5 centimeters and for Distance G is 3.5 centimeters.

Hand width W can be measured across the MP joints 350 of the long fingers 200 on the palm 102 of the hand 100 as illustrated in FIGS. 3 and 7, for example. Hand width W can be divided into three segments in a ratio of 40:30:30 corresponding to the measured distances for the lines RPL, CTZD and UPL as illustrated in FIG. 7. These segments therefore respectively represent the approximate widths of the radial palmar line RPL, "carpal tunnel zone" CTZ (represented by the line CTZD) and ulnar palmar line UPL. The width of the curve 310 of the finger cup 108 is the same as the width W of the hand 100 and starts on the x-axis at the ulnar side 111 of the hand 100. Width W of the hand 100 is related to hand sizes and the width W will be greater for larger hands 100.

Hand width sizes W were measured on 30 adult female hands and 25 adult male hands. Body height of the females in the group ranged from 4'10" to 5'10". Body height of the males in the group ranged from 5'4" to 6'3". The range of hand width W for the female group was from 7 cm to 9 cm. The hand width W for the majority of the 30 females was between 8 cm and 8.5 cm. The range of hand width W for the 25 males was from 8.5 cm to 10.5 cm. The range of hand width W for the majority of the male group was between 9.5 cm and 10 cm.

Figure 8:
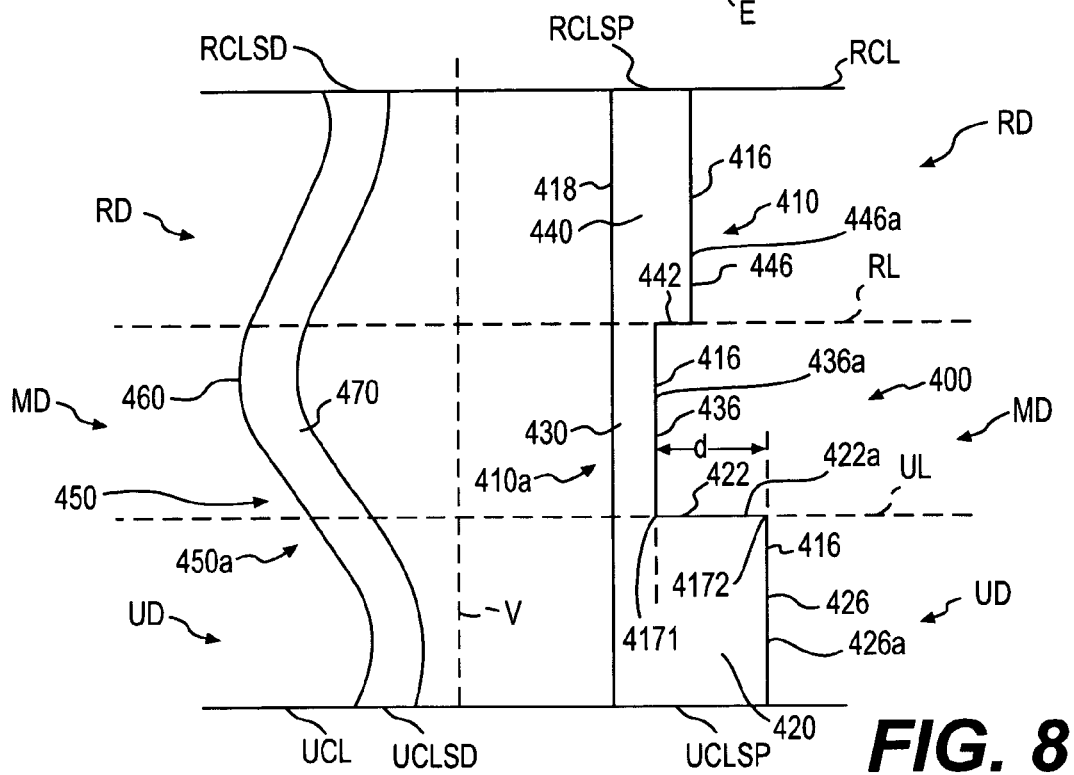
FIG. 8 is a schematic view illustrating an embodiment of parallel handles of the present invention.
Figure 9:
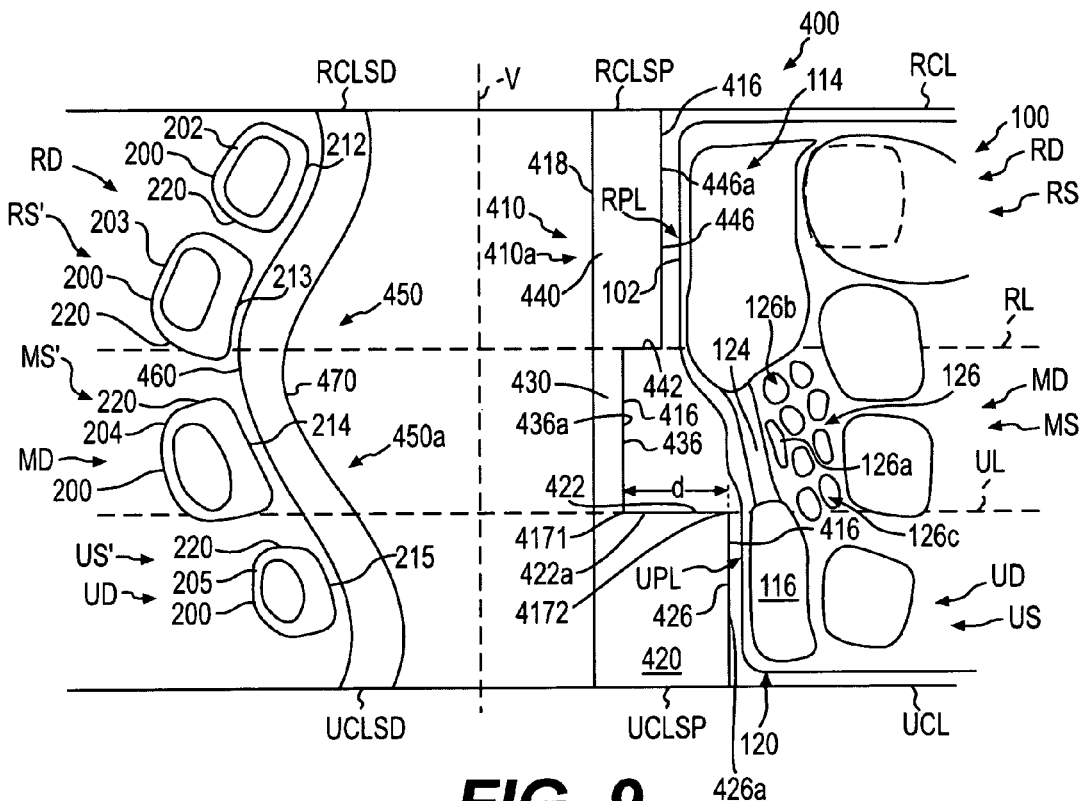
FIG. 9 is a view illustrating an outline of the hand contacting a schematic view of an embodiment of parallel handles of the present invention.

FIG. 8 and FIG. 9 illustrate a parallel handle schematic 400 of the present invention as formatted for a right hand 100. The parallel handle schematic 400 of the present invention is based on the hand measurements illustrated in the graph of FIG. 7. The parallel handle schematic 400 of the present invention relates the radial palmar line RPL, ulnar palmar line UPL, distal side CTZD of the "carpal tunnel zone" CTZ and the curve 310 of the finger cup 108 to corresponding areas on the parallel handle schematic 400 of the present invention.

Referring to FIGS. 7 through 9, the ulnar palmar line UPL illustrated in the graph of FIG. 7 corresponds to the proximal side 426 of the ulnar section 420 of the proximal part 410 of the parallel handle schematic 400 of the present invention. The distal end CTZD in the graph of FIG. 7 corresponds to proximal side 436 of the middle section 430 of the proximal part 410 of the parallel handle schematic 400 of the present invention. The radial palmar line UPL in the graph of FIG. 7 corresponds to the proximal side 446 of the radial section 440 of the proximal part 410 of the parallel handle schematic 400 of the present invention. The curve 310 of the finger cup 108 in the graph of FIG. 7 corresponds to the distal side 460 of the distal part 450 of the parallel handle schematic 400 of the present invention.

When referring to the hand 100 proximal is closer to the wrist 120 and distal is closer to the tips 200a of the long fingers 200 of the hand 100. Likewise, the parallel handle schematic 400 of the present invention can be separated by dashed line V into a proximal part 410 and a distal part 450, the proximal part or proximal moving member 410 having a first elongated body 410a and the distal part or distal moving member 450 having a second elongated body 450a. The proximal part 410 is closer to the wrist 120 and the distal part 450 is closer to the tips 200a of the long fingers 200 of the hand 100.

As illustrated in FIG. 8 and FIG. 9 two parallel lines border the proximal part 410 and distal part 450 of the parallel handle schematic 400 of the present invention. The two parallel lines are the radial contiguous line RCL and the ulnar contiguous line UCL of the parallel handle schematic 400 of the present invention. The ulnar contiguous line UCL is placed on the x-axis as shown in the graph of FIG. 7. The radial contiguous line RCL is positioned at a distance from the ulnar contiguous line UCL equal to the width W of a hand 100 described in relation to the graph in FIG. 7. The radial contiguous Line RCL includes a radial contiguous segment RCLS that forms the radial end of the radial section 440 of the proximal part 410 of the parallel handle schematic 400 of the present invention. The ulnar contiguous Line UCL includes a ulnar contiguous segment UCLS that forms the ulnar end of the ulnar section 420 of the proximal part 410 of the parallel handle schematic 400 of the present invention.

The radial line RL and the ulnar line UL illustrated in FIG. 8 and FIG. 9 separate the parallel handle schematic 400 of the present invention into a radial section 440, middle section 430 and ulnar section 420. The ulnar line UL includes an ulnar segment 422 forming a connecting surface 422a that connects an ulnar surface 426a formed by the proximal side 426 of the ulnar section 420 to a middle surface 436a formed by the proximal side 436 of the middle section 430. The connecting surface 422a of the proximal part 410 on the proximal side 416 of the first elongated body 410a connects the middle surface 436a of the middle section 430 of the proximal part 410 to the ulnar surface 426a of the ulnar section 420 of the proximal part 410, and with the connecting surface 422a extending proximally for a distance "d" from a position at one end 4171 of the middle surface 436a of the middle section 430 of the proximal part 410 to a position at one end 4172 of the ulnar surface 426a of the ulnar section 420 of the proximal part 410. The distance "d" that the connecting surface 422a extends is at least of a length whereby the ulnar surface 426a of the ulnar section 420 of the proximal part 410 extends beyond the middle surface 436a of the middle section 430 of the proximal part 410, and whereby the handle or apparatus 400 is positioned within the hand without placing substantial pressure on the surface of the hand located over the carpal tunnel. Further, the distance that the connecting surface 422a extends can be at least of a length whereby the ulnar surface 426a of the ulnar section 420 of the proximal part 410 extends beyond the radial surface 446a of the radial section 440 of the proximal part 410 on the proximal side 416 of the first elongated body 410a such as illustrated in FIGS. 8 and 9, as well as FIGS. 11 through 12R. Also, relative to the ulnar surface 426a of the ulnar section 420 of the proximal part 410 on the proximal side 416 of the first elongated body 410a, the radial surface 446a of the radial section 440 of the proximal part 410 can extend proximally for a distance different than, equal to or greater than a distance that the middle surface 436a of the middle section 430 of the proximal part 410 extends proximally, such as illustrated in FIGS. 8 and 9, as well as FIGS. 11 through 12R. Further, the radial line RL includes a radial segment 442 that connects the proximal side 446 of the radial section 440 to the proximal side 436 of the middle section 430 of the proximal part 410 of the parallel handle schematic 400 of the present invention. The distal side 418 of proximal part 410 of the parallel handle schematic 400 of the present invention connects the radial contiguous segment RCLSP to the ulnar contiguous segment UCLSP. The distal side 418 can be of any suitable configuration, such as a curved configuration or a linear configuration.

The distal part 450 of the parallel handle schematic 400 of the present invention is completed by connecting the proximal side 470 of distal part 450 to distal side 460 by the radial contiguous segment RCLSD on the radial contiguous line RCL at one end of the distal part 450 and by the ulnar contiguous segment UCLSD on the ulnar contiguous line UCL at the other end of the distal part 450. Furthermore, the distal side 460 in addition to conforming to the curve 310 of the finger cup 108 can also be of other suitable configurations, such that when the corresponding proximal part 410 engages with the hand 100, the corresponding proximal part 410 avoids contacting or putting undue pressure on the palm 102 in the area of CT 126 of the hand 100. Also, the proximal side 470 can be of any suitable configuration, such as a curved configuration or a linear configuration.

Furthermore, as illustrated in FIG. 8 and FIG. 9 the radial line RL and the ulnar line UL divide the parallel handle schematic 400 of the present invention including the proximal part 410 and the distal part 450 into a radial division RD, middle division MD and ulnar division UD. As illustrated in FIG. 9, the radial division RD corresponds to the radial section RS of the proximal part 410 and the radial section RS' of the distal part 450 and the middle division MD corresponds to the middle section MS of the proximal part 410 and the middle section MS' of the distal part 450, and the ulnar division UD corresponds to the ulnar section US of the proximal part 410 and the ulnar section US' of the distal part 450. Also referring to FIGS. 1 through 6, the radial division RD of the parallel handle schematic 400 of the present invention is related to the thenar muscle area 114 on the radial side 110 of the palm 102 of the hand 100, the index finger 202 and can include at least part of the middle finger 203 of the hand 100. The middle division MD of the parallel handle schematic 400 of the present invention is related to the CT area 126 of the palm 102 of the hand 100, can include at least part of the middle finger 203 and can include at least part of the ring finger 204 of the hand 100. The ulnar division UD of the parallel handle schematic 400 of the present invention is related to the hypothenar muscle area 116 on the ulnar side 111 of the palm 102 of the hand 100 and can include at least part of the ring finger 204 and the small finger 205 of the hand 100.

Also referring to FIG. 9, with reference to FIGS. 1 through 6, FIG. 9 illustrates the contact areas of the parallel handle schematic 400 of the present invention with the hand 100. The proximal part 410 of the parallel handle schematic 400 of the present invention contacts the thenar muscle area 114 and the hypothenar muscle area 116 of the hand 100. Specifically, the proximal side 446 of the radial section 440 of the proximal part 410 of the parallel handle schematic 400 of the present invention contacts the palm 102 of the hand 100 near the radial palmar line RPL. The proximal side 426 of the ulnar section 420 of the proximal part 410 of the parallel handle schematic 400 of the present invention contacts the palm 102 of the hand 100 near the ulnar palmar line UPL. The proximal side 436 of the middle section 430 of the proximal part 410 of the parallel handle schematic 400 of the present invention is adjacent to the area of the CT 126. However, the proximal side 436 of the middle section 430 of the proximal part 410 the parallel handle schematic 400 of the present invention avoids contacting or putting undue pressure on the palm 102 in the area of CT 126 of the hand 100. The distal side 460 of the distal part 450 of the parallel handle schematic 400 of the present invention contacts of the inner surfaces 211 of each middle segment 220 of the long fingers 200 of the hand 100.

The parallel handle schematic 400 of the present invention is the basis of a method for designing parallel handles with parallel moving members and guide members. However, for certain applications of the parallel handle of the present invention, such as for a scissors or pincer application, the proximal part 410 and the distal part 450 do not have to be parallel to each other or end parallel to each other or move parallel to each other and, while it is desirable, it is not necessary that the distal side 460 conform generally to the curve 310 of the finger cup 108. However, as mentioned previously in such a parallel handle, the proximal side 436 of the middle section 430 of the proximal part 410 the parallel handle schematic 400 of the present invention avoids contacting or putting undue pressure on the palm 102 in the area of CT 126 of the hand 100.

At least one of the moving members, based on the method for designing the parallel handles for the present invention, can move relative to a guide member when a hand is positioned in a suitable position in relation to the parallel handle, such as the T Position, or moves in a range of the suitable position, such as from the Spread T Position STP to the Closed T Position CTP. Guide members produced by the design method for parallel handles of the present invention desirably keep the moving members in substantially parallel relation when one or the other of the moving members are moved. The moving members, based on the method for designing parallel handles, are attached to the working ends of tools, instruments or other implements that cut, bite, hold, grasp, measure, pinch, pull, push, squeeze or perform other functions. Handles designed from this method can be used for bicycle brakes, calipers, hand dynamometers, pliers, spreaders, surgical instruments, wrenches and other such implements.

The parallel handle schematic 400 of the present invention combines a proximal part 410, distal part 450, and moving or supporting members for the proximal part 410 and for the distal part 450 that are positioned respectively in corresponding relation to the radial contiguous line RCL and ulnar contiguous line UCL. Continuing with further reference to FIGS. 8 through 10M, of various embodiments of parallel handles according to the present invention are illustrated. Each section, side or line of the parallel handle schematic 400 of the present invention can be used to design a parallel handle based on the design method of the present invention, such as those illustrated in FIGS. 10A through 10M, for example.

Figure 10A:
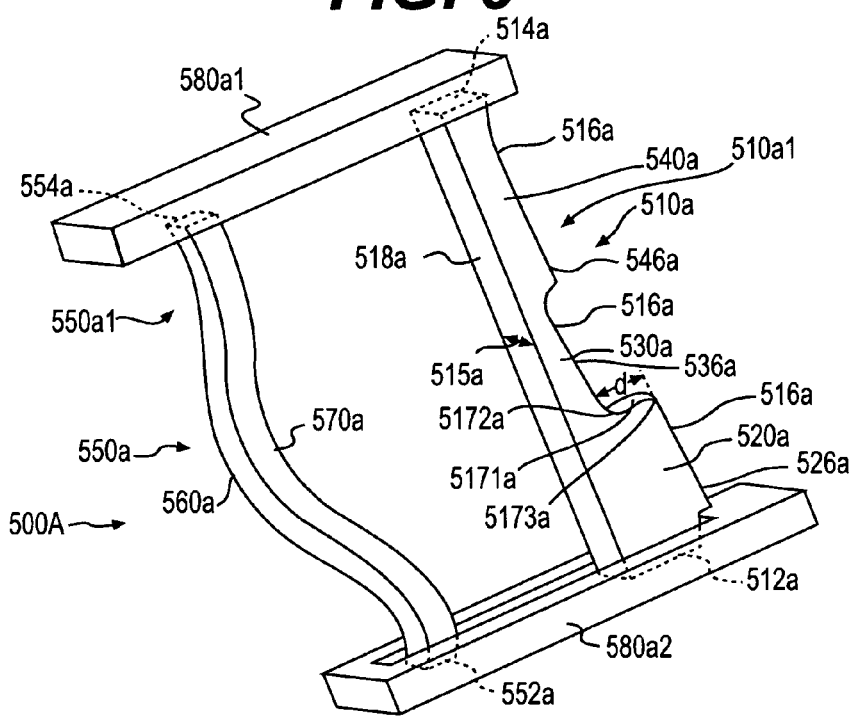

Continuing with reference to FIG. 10A a parallel handle 500A according to the present invention is illustrated. The proximal moving member 510$a$ and the distal moving member 550$a$ of the parallel handle 500A based on the design method of the present invention correspond to the proximal part 410 and distal part 450 of the parallel handle schematic 400 of the present invention. The guide members 580$a$1 and 580$a$2 of the parallel handle 500A based on the design method of the present invention correspond to the radial contiguous line RCL and ulnar contiguous line UCL of the parallel handle schematic 400 of the present invention.

Figure 10B:
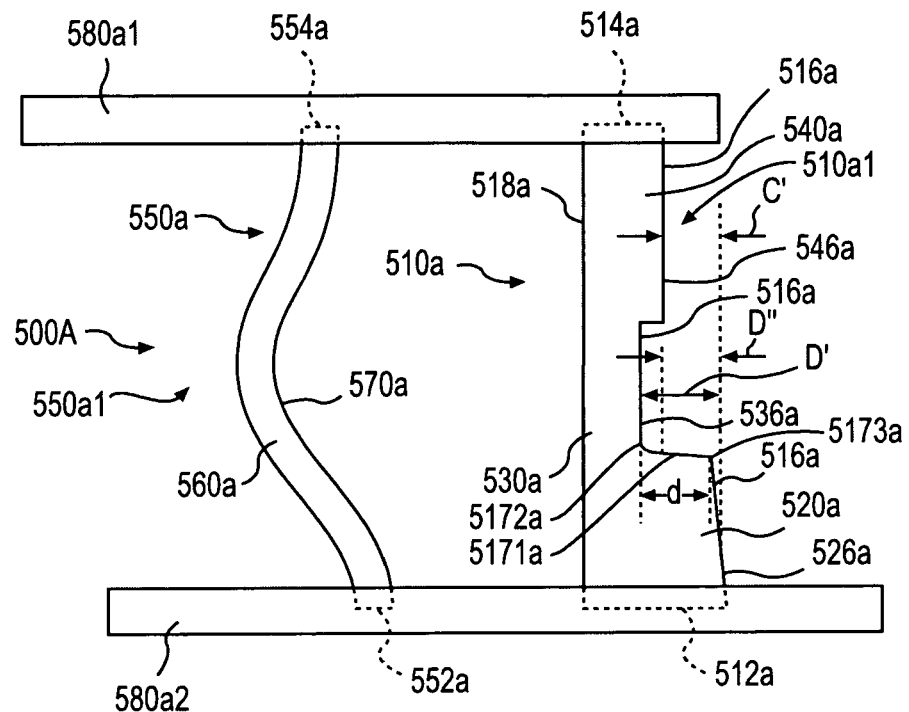

The proximal part or proximal moving member 510$a$ having a first elongated body S10$a$1 of the parallel handle 500A in FIG. 10A, based on the method for designing parallel handles or apparatus of the present invention, has an ulnar section 520$a$, a middle section 530$a$ and a radial section 540$a$. The proximal part or proximal moving member 510$a$ of the parallel handle 500A, based on the method for designing parallel handles or apparatus of the present invention, also has a proximal side or proximal surface 516$a$ and a distal side or distal surface 518$a$. The radial surface 546$a$ of the radial section 540$a$ of the proximal part or proximal moving member 510$a$ of the parallel handle 500A, based on the method for designing parallel handles or apparatus of the present invention, corresponds to the proximal side 446 of the radial section 440 of the proximal moving member or proximal part 410 of the parallel handle schematic 400 of the present invention. The middle surface 536a of the middle section 530a of the proximal part or proximal moving member 510a of the parallel handle 500A, based on the method for designing parallel handles or apparatus of the present invention, corresponds to the proximal side 436 of the middle section 430 of the proximal part 410 of the parallel handle schematic 400 of the present invention. The ulnar surface 526a of the ulnar section 520a of the proximal part or proximal moving member 510a of the parallel handle 500A, based on the method for designing parallel handles or apparatus of the present invention, corresponds to the proximal side 426 of the ulnar section 420 of the proximal part 410 of the parallel handle schematic 400 of the present invention. A connecting surface 5171a, corresponding to the connecting surface 422a, of the proximal part or proximal moving member 510a on the proximal side 516a of the first elongated body 510a1 connects. on the proximal side 516a of the first elongated body 510a1, the middle surface 536a of the middle section 530a of the proximal part 510a to the ulnar surface 526a of the ulnar section 520a of the proximal part 510a, and with the connecting surface 5171a extending proximally for a distance "d" from a position at one end 5172a of the middle surface 536a of the middle section 530a of the proximal part 510a to a position at one end 5173a of the ulnar surface 526a of the ulnar section 520a of the proximal part 510a, wherein the distance "d" that the connecting surface 5171a extends is at least of a length whereby the ulnar surface 526a of the ulnar section 520a of the proximal part 510a extends beyond the middle surface 536a of the middle section 530a of the proximal part 510a on the proximal side 516a of the first elongated body 510a1, and whereby the handle or apparatus 500A is positioned within the hand without placing substantial pressure on the surface of the hand located over the carpal tunnel. Further, the distance that the connecting surface 5171a extends can be at least of a length whereby the ulnar surface 526a of the ulnar section 520a of the proximal part 510a extends beyond the radial surface 546a of the radial section 540a of the proximal part 510a on the proximal side 516a of the first elongated body 510a1, such as illustrated in FIGS. 10A and 10B, as well as FIGS. 11 through 12R. Also, relative to the ulnar surface 526a of the ulnar section 520a of the proximal part 510a on the proximal side 516a of the first elongated body 510a1, the radial surface 546a of the radial section 540a of the proximal part 510a can extend proximally for a distance different than, equal to or greater than a distance that the middle surface 536a of the middle section 530a of the proximal part 510a extends proximally, such as illustrated in FIGS. 10A and 10B, as well as FIGS. 11 through 12R. The distal surface 518a of the proximal part or proximal moving member 510a of the parallel handle 500A based on the method for designing parallel handles of the present invention corresponds to the distal side 418 of the proximal part 410 of the parallel handle schematic 400 of the present invention.

As illustrated in FIG. 10A, the distal part or distal moving member 550a having a second elongated body 550a1 of the parallel handle 500A, based on the method for designing parallel handles or apparatus of the present invention, has a distal side or distal surface 560a and a proximal side or proximal surface 570a. The distal side or distal surface 560a of the distal moving member 550a of the parallel handle 500A, based on the method for designing parallel handles or apparatus of the present invention, corresponds to the distal side 460 of the distal part 450 of the parallel handle schematic 400 of the present invention. The proximal side or proximal surface 570a of the distal part or distal moving member 550a of the parallel handle 500A, based on the method for designing parallel handles or apparatus of the present invention, can correspond to the proximal side 470 of the distal part 450 of the parallel handle schematic 400 of the present invention.

Continuing with reference to FIG. 10A, the radial surface 546a, middle surface 536a and ulnar surface 526a of the proximal moving member 510a of the parallel handle 500A based on the method for designing parallel handles of the present invention can be flat, angled or curved. The width of the radial surface 546a, the middle surface 536a and the ulnar surface 526a of the proximal moving member 510a of the parallel handle 500A based on the method for designing parallel handles of the present invention can follow the 40:30:30 approximate ratio discussed related to width of the radial palmar line RPL, distal side CTZD of the "carpal tunnel zone" CTZ and ulnar palmar line UPL discussed in reference to hand width W in FIG. 7.

Continuing with reference to FIG. 10B which is a profile view of the parallel handle 500A of FIG. 10A and, with reference to the graph of FIG. 7, for most hands 100 one-centimeter is typically an approximation for the distance C. As illustrated in FIG. 10B one centimeter is also a reasonable approximate gap for distance C' between the radial surface 546a of the radial section 540a and the ulnar surface 526a of the ulnar section 520a of the proximal moving member 510a of the parallel handle 500A based on the method for designing parallel handles of the present invention. As discussed with reference to the graph of FIG. 7, 1.5 centimeters is an approximation for distance D on the graph of FIG. 7. 1.5 centimeters is also a reasonable approximate gap for distance D' between the middle surface 536a of the middle section 530a and the ulnar surface 526a of the ulnar section 520a of the proximal moving member 510a of the parallel handle 500A based on the method for designing parallel handles or apparatus of the present invention.

The importance of distance D', referred to in FIG. 10B, is to avoid contacting or putting undue pressure on the palm 102 in the area of CT 126 of the hand 100 between the "carpal tunnel zone" CTZ of the palm 102 of the hand 100 and the middle surface 536a of the middle section 530a of the proximal moving member 510a for a parallel handle 500A based on the method for designing parallel handles of the present invention. In this regard, distance D' can vary so to be equal to or less than distance C' and still avoid contacting or putting undue pressure on the "carpal tunnel zone" CTZ for certain designs of parallel handles based on the method for designing parallel handles of the present invention, such as the distance D" in FIG. 10B.

Therefore, distance D' can equal or be less than distance C'. However, when the distance D' is less than C', to avoid contacting or placing undue pressure on the "carpal tunnel zone" CTZ with the middle surface 536a of the middle section 530a, the depth 515a of the proximal moving member 510a of the parallel handle 500A must be significantly less than, typically one-half the distance between the distal end CTZD and the proximal end CTZP of the "carpal tunnel zone" CTZ. Therefore, as the depth 515a increases, distance D' typically will increase to avoid contacting or putting undue pressure on the "carpal tunnel zone" CTZ by the middle segment 530a of the proximal moving member 510a of a handle 500A based on the method for designing parallel handles of the present invention. Further, a relatively small depth 515a for the middle section 530a of the proximal moving member 510a, such depth 515a being equal of less than one-half the distance between the distal end CTZD and the proximal end CTZP of the "carpal tunnel zone"

CTZ, of the parallel handle 500A may not need a recessed middle section 530a to avoid contacting or placing undue pressure on the "carpal tunnel zone" CTZ. However, when the depth 515a for the middle section 530a of the proximal moving member 510a is generally greater than one-half the distance between the distal end CTZD and the proximal end CTZP of the "carpal tunnel zone" CTZ, the parallel handle 500A based on the method for designing parallel handles of the present invention typically may need a recess at the surface 536a of the middle section 530a of a proximal moving member 510a of a handle 500A to avoid contacting or putting undue pressure on the "carpal tunnel zone" CTZ.

The proximal surface or proximal side 516a of the proximal part or proximal moving member 510a of the parallel handle 500A can correspond to the proximal side 416 of the proximal part 410 of the parallel handle schematic 400 of the present invention. The distal side or distal surface 560a of the distal part or distal moving member 550a of the parallel handle 500A can correspond to the distal side 460 of the distal part 450 of the parallel handle schematic 400 of the present invention. However, the length, width and cross-sectional shape of a proximal part or proximal moving member 510a and a distal part or distal moving member 550a depend on use and design of the individual application.

As illustrated in FIG. 10A, in the embodiment of the parallel handle 500A the guide members 580a1 and 580a2 are located on the radial side 514a and ulnar side 512a of the proximal moving member 510a and the radial side 554a and ulnar side 552a of the distal moving member 550a of the parallel handle 500A based on the method for designing parallel handles of the present invention. However, the guide members 580a1 and 580a2 do not need to be placed at the radial side 514a and ulnar side 512a of the proximal moving member 510a or on the radial side 554a and ulnar side 552a of the distal moving member 550a of the parallel handle 500A based on the method for designing parallel handles of the present invention. The guide members 580a1 and 580a2 of the parallel handles 500A based on the method for designing parallel handles of the present invention can be placed on either side of the hand 100 or only a single guide member can be used. The guide member or guide members can also be placed on one side of the hand 100 or spread apart from the radial side 110 or ulnar side 111 of the hand 100, or a guide member can serve as a pivot member permitting movement of the proximal moving member and the distal moving member. Factors related to size, design and use determine the location of the guide member or guide members relative to the proximal moving member and distal moving member.

Figure 10C:
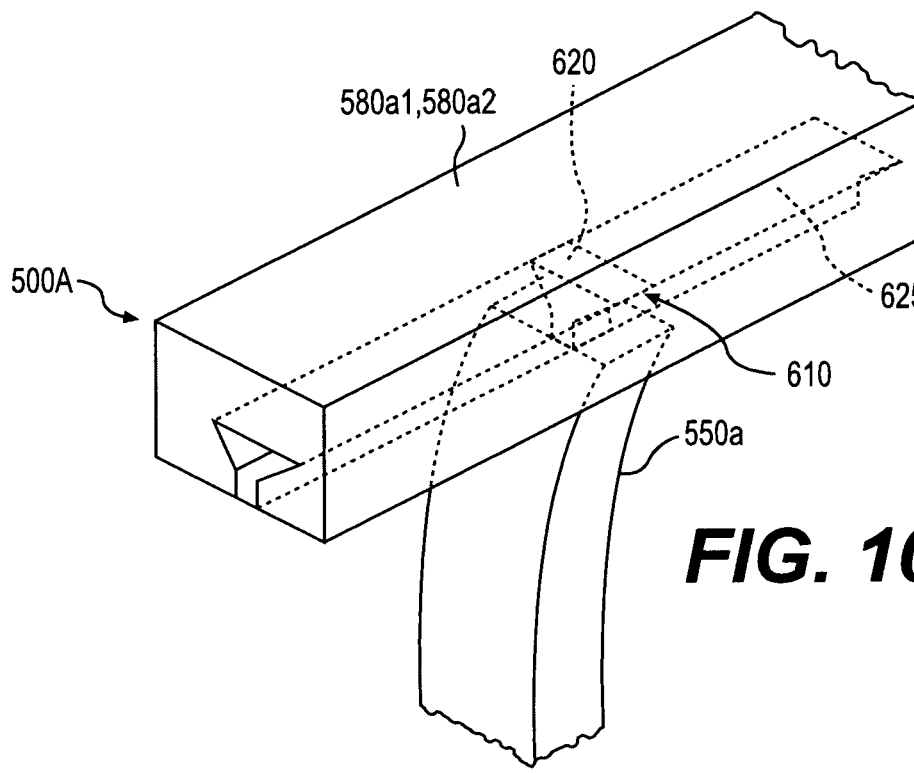
Figure 10D:
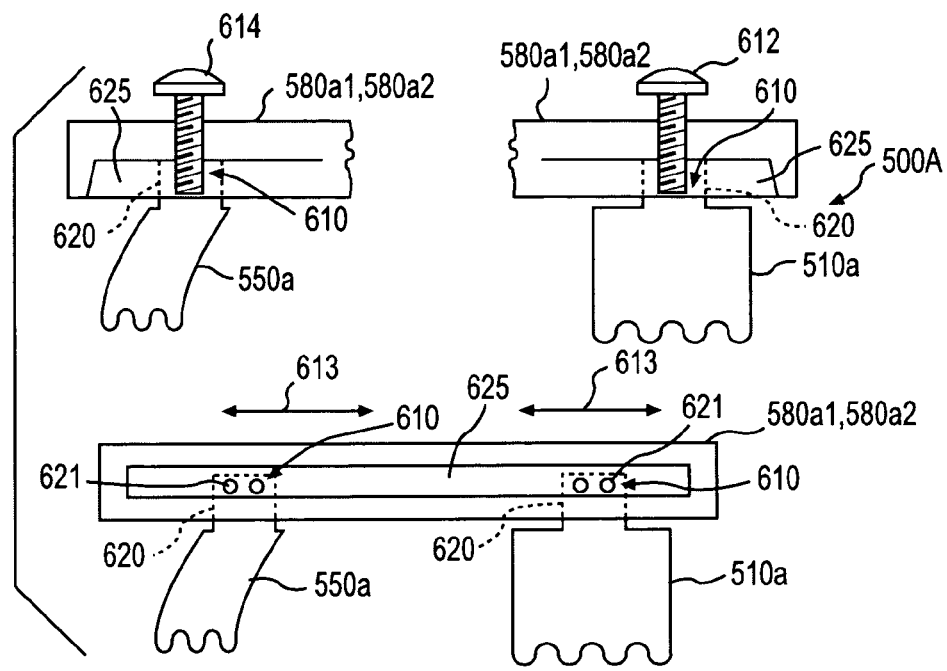

Referring to FIG. 10C and FIG. 10D, suitable connection members 610 between guide members 580a1 and 580a2 and proximal moving member 510a and distal moving member 550a for the parallel handle 500A are illustrated. The connection members 610 can be used to maintain and stabilize alignment of the proximal moving member 510a and distal moving member 550a. A suitable connection member 610 can include projecting parts 620, which can also include bearings 621, that allow the proximal moving member 510a and distal moving member 550a to move or slide along a track 625 or other device.

Also, as illustrated in FIG. 10D, the connection members 610 can include a fixed connection anchor 612, such as screws or pin members, to fix the position of the proximal moving member 510a to guide members 580a1, 580a2 to enable the distal moving member 550a to move toward or away relative to the fixed position of a proximal moving member 510a of a parallel handle 500A. Similarly, as illustrated in FIG. 10D, the connection members 610 can include a fixed connection anchor 614, such as screws or pin members, to fix the position of the distal moving member 550a to a guide member 580a1, 580a2 to enable the proximal moving member 510a to move toward or away relative to the fixed position of a distal moving member 550a of a parallel handle 500A. Moreover, as illustrated in FIG. 10D, when suitable connection members 610 are utilized, such as bearings, and the proximal moving member 510a and the distal moving member 550a are not fixed to the guide members 580a1, 580a2 then both the proximal moving member 510a and the distal moving member 550a can move toward or away from each other as illustrated by the arrows 613, such as to actuate the working ends of a parallel handle based on the method for designing parallel handles of the present invention.

Figure 10E:
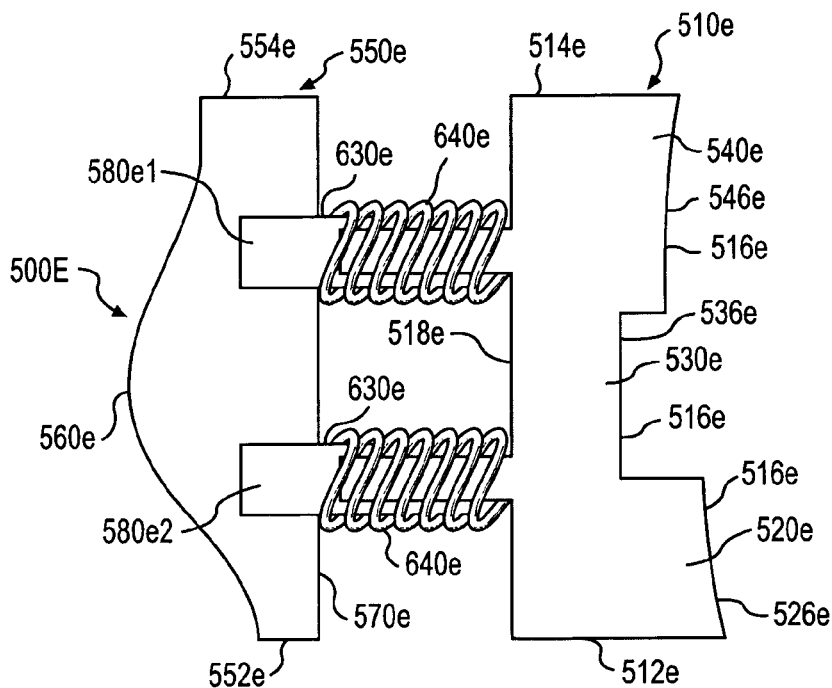

Continuing with reference to FIG. 10E another embodiment of a parallel handle 500E based on the design method of the present invention is illustrated. Similar to the parallel handle 500A of FIG. 10A, parallel handle 500E has a proximal moving member 510e and a distal moving member 550e, whereby the proximal side 536e of the middle section 530e of the proximal moving member 510e of the parallel handle 500E avoids contacting or putting undue pressure on the palm 102 in the area of CT 126 of the hand 100. The proximal moving member 510e and the distal moving member 550e of the parallel handle 500E based on the design method of the present invention correspond to the proximal part 410 and distal part 450 of the parallel handle schematic 400 of the present invention. The guide members 580e1 and 580e2 of the parallel handle 500E based on the design method of the present invention correspond to the radial contiguous line RCL and ulnar contiguous line UCL of the parallel handle schematic 400 of the present invention. However, the guide members 580e1 and 580e2 are positioned between the radial end 514e and the ulnar end 512e of the proximal moving member 510e and positioned between the radial end 554e and the ulnar end of 552e of the distal moving member 550e. Also, the guide member 580e1 and 580e2 each have a telescoping device 630e to permit relative movement of the proximal moving member 510e and the distal moving member 550e, and the telescoping device 630e can also include a coil spring 640e for control and biasing of the movement of the distal moving member 510e and proximal moving member 550e.

The proximal moving member 510e of the parallel handle 500E in FIG. 10E based on the method for designing parallel handles of the present invention has an ulnar section 520e, a middle section 530e and a radial section 540e. The proximal moving member 510e of the parallel handle 500E based on the method for designing parallel handles of the present invention also has a proximal side 516e and a distal side 518e. The radial surface 546e of the radial section 540e of the proximal moving member 510e of the parallel handle 500E based on the method for designing parallel handles of the present invention corresponds to the proximal side 446 of the radial section 440 of the proximal part 410 of the parallel handle schematic 400 of the present invention. The middle surface 536e of the middle section 530e proximal moving member 510e of the parallel handle 500E based on the method for designing parallel handles of the present invention corresponds to the proximal surface 436 of the middle section 430 of the proximal part 410 of the parallel handle schematic 400 of the present invention. The ulnar surface 526e of the ulnar section 520e of the proximal moving member 510e of the parallel handle 500E based on the method for designing parallel handles of the present invention corresponds to the proximal side 426 of the ulnar section 420 of the proximal part 410 of the parallel handle schematic 400 of the present invention. The distal surface 518e of the proximal moving member 510e of the parallel handle 500E based on the method for designing parallel handles of the present invention corresponds to the distal side 418 of the proximal part 410 of the parallel handle schematic 400 of the present invention.

As illustrated in FIG. 10E, the distal moving member 550e of the parallel handle 500E based on the method for designing parallel handles of the present invention has a distal surface 560e and a proximal surface 570e. The distal surface 560e of the distal moving member 550e of the parallel handle 500E based on the method for designing parallel handles of the present invention corresponds to the distal side 460 of the distal part 450 of the parallel handle schematic 400 of the present invention. The proximal surface 570e of the distal moving member 550e of the parallel handle 500E based on the method for designing parallel handles of the present invention can correspond to the proximal side 470 of the distal part 450 of the parallel handle schematic 400 of the present invention.

Figure 10F:
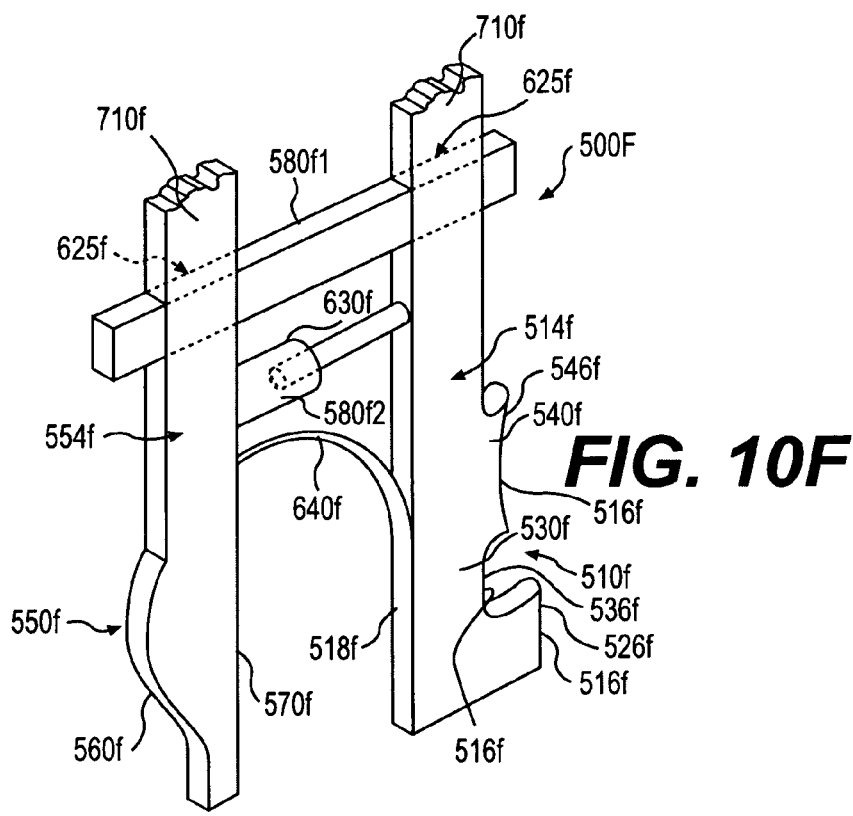

Continuing with reference to FIG. 10F another embodiment of a parallel handle 500F based on the design method of the present invention is illustrated. Similar to the parallel handle 500A of FIG. 10A, parallel handle 500F has a proximal moving member 510f and a distal moving member 550f, whereby the proximal side 536f of the middle section 530f of the proximal moving member 510f of the parallel handle 500F avoids contacting or putting undue pressure on the palm 102 in the area of CT 126 of the hand 100. The proximal moving member 510f and the distal moving member 550f of the parallel handle 500F based on the design method of the present invention correspond to the proximal part 410 and distal part 450 of the parallel handle schematic 400 of the present invention. The guide members 580f1 and 580f2 of the parallel handle 500F based on the design method of the present invention correspond to the radial contiguous line RCL and ulnar contiguous line UCL of the parallel handle schematic 400 of the present invention. However, the guide members 580f1 and 580f2 are each positioned to the radial side 514f of the proximal moving member 510f and the radial side 554f of the parallel handle 500F. Also, the guide member 580f1 slideably engages a track 625f in the proximal moving member 510f and the distal moving member 550f to permit relative movement of the proximal moving member 510f and the distal moving member 550f. Also, the guide member 580f2 has a telescoping device 630f to permit relative movement of the proximal moving member 510f and the distal moving member 550f. Additionally, the parallel handle 500F has leaf spring 640f positioned between and engaging the proximal moving member 510f and the distal moving member 550f for control and biasing of the movement of the proximal moving member 510f and distal moving member 550f. Furthermore, the parallel handle 500F has a working end 710f on each of the proximal moving member 510f and the distal moving member 550f on which an implement, such as a scissors or pincers, can be attached to the parallel handle 500F.

The proximal moving member 510f of the parallel handle 500F in FIG. 10F based on the method for designing parallel handles of the present invention has an ulnar section 520f, a middle section 530f and a radial section 540f. The proximal moving member 510f of the parallel handle 500F based on the method for designing parallel handles of the present invention also has a proximal side 516f and a distal side 518f. The radial surface 546f of the radial section 540f of the proximal moving member 510f of the parallel handle 500F based on the method for designing parallel handles of the present invention corresponds to the proximal side 446 of the radial section 440 of the proximal part 410 of the parallel handle schematic 400 of the present invention. The middle surface 536f of the middle section 530f proximal moving member 510f of the parallel handle 500F based on the method for designing parallel handles of the present invention corresponds to the proximal surface 436 of the middle section 430 of the proximal part 410 of the parallel handle schematic 400 of the present invention. The ulnar surface 526f of the ulnar section 520f of the proximal moving member 510f of the parallel handle 500F based on the method for designing parallel handles of the present invention corresponds to the proximal side 426 of the ulnar section 420 of the proximal part 410 of the parallel handle schematic 400 of the present invention. The distal surface 518f of the proximal moving member 510f of the parallel handle 500F based on the method for designing parallel handles of the present invention corresponds to the distal side 418 of the proximal part 410 of the parallel handle schematic 400 of the present invention.

As illustrated in FIG. 10F, the distal moving member 550f of the parallel handle 500F based on the method for designing parallel handles of the present invention has a distal surface 560f and a proximal surface 570f. The distal surface 560f of the distal moving member 550f of the parallel handle 500F based on the method for designing parallel handles of the present invention corresponds to the distal side 460 of the distal part 450 of the parallel handle schematic 400 of the present invention. The proximal surface 570f of the distal moving member 550f of the parallel handle 500F based on the method for designing parallel handles of the present invention can correspond to the proximal side 470 of the distal part 450 of the parallel handle schematic 400 of the present invention.

Figure 10G:
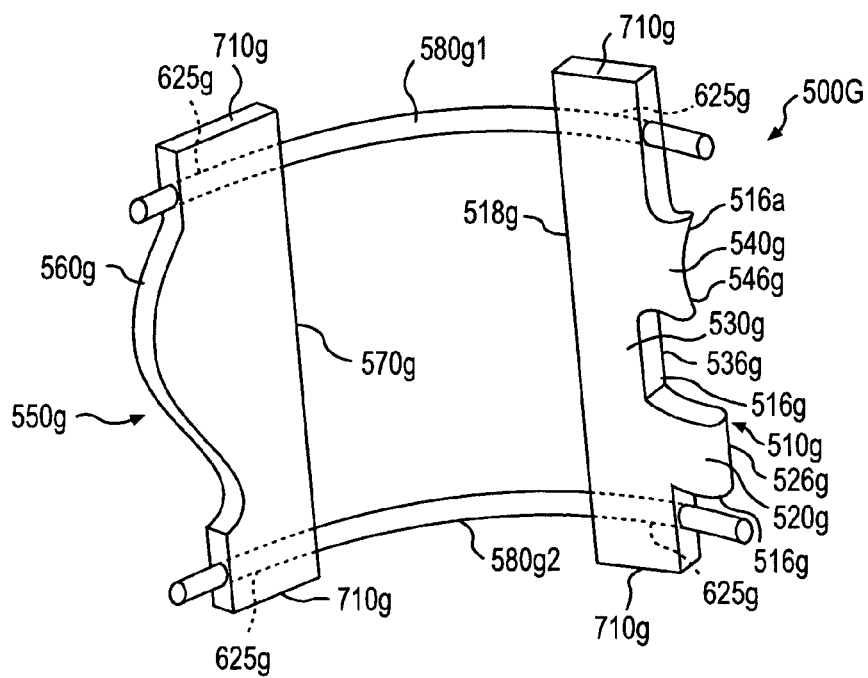

Continuing with reference to FIG. 10G another embodiment of a parallel handle 500G based on the design method of the present invention is illustrated. Similar to the parallel handle 500A of FIG. 10A, parallel handle 500G has a proximal moving member 510g and a distal moving member 550g, whereby the proximal side 536g of the middle section 530g of the proximal moving member 510g of the parallel handle 500G avoids contacting or putting undue pressure on the palm 102 in the area of CT 126 of the hand 100. The proximal moving member 510g and the distal moving member 550g of the parallel handle 500G based on the design method of the present invention correspond to the proximal part 410 and distal part 450 of the parallel handle schematic 400 of the present invention. The guide members 580g1 and 580g2 of the parallel handle 500G based on the design method of the present invention correspond to the radial contiguous line RCL and ulnar contiguous line UCL of the parallel handle schematic 400 of the present invention. However, the guide members 580g1 and 580g2 are arcuately or curved in shape. Also, the guide members 580g1 and 580g2 slideably engage tracks 625g in the proximal moving member 510g and the distal moving member 550g to permit relative movement of the proximal moving member 510g and the distal moving member 550g. The tracks 625g can be or a curved or arcuate shape to conform to the shape of the guide members 580g1 and 580g2. Furthermore, the parallel handle 500G has a working end 710g on each of the proximal moving member 510g and the distal moving member 550g on which an implement, such as a scissors or pincers, can be attached to the parallel handle 500G.

The proximal moving member 510g of the parallel handle 500G in FIG. 10G based on the method for designing parallel handles of the present invention has an ulnar section 520g, a middle section 530g and a radial section 540g. The proximal moving member 510g of the parallel handle 500G based on the method for designing parallel handles of the present invention also has a proximal side 516g and a distal side 518g. The radial surface 546g of the radial section 540g of the proximal moving member 510g of the parallel handle 500G based on the method for designing parallel handles of the present invention corresponds to the proximal side 446 of the radial section 440 of the proximal part 410 of the parallel handle schematic 400 of the present invention. The middle surface 536g of the middle section 530g proximal moving member 510g of the parallel handle 500G based on the method for designing parallel handles of the present invention corresponds to the proximal surface 436 of the middle section 430 of the proximal part 410 of the parallel handle schematic 400 of the present invention. The ulnar surface 526g of the ulnar section 520g of the proximal moving member 510g of the parallel handle 500G based on the method for designing parallel handles of the present invention corresponds to the proximal side 426 of the ulnar section 420 of the proximal part 410 of the parallel handle schematic 400 of the present invention. The distal surface 518g of the proximal moving member 510g of the parallel handle 500G based on the method for designing parallel handles of the present invention corresponds to the distal side 418 of the proximal part 410 of the parallel handle schematic 400 of the present invention.

As illustrated in FIG. 10G, the distal moving member 550g of the parallel handle 500G based on the method for designing parallel handles of the present invention has a distal surface 560g and a proximal surface 570g. The distal surface 560g of the distal moving member 550g of the parallel handle 500G based on the method for designing parallel handles of the present invention corresponds to the distal side 460 of the distal part 450 of the parallel handle schematic 400 of the present invention. The proximal surface 570g of the distal moving member 550g of the parallel handle 500G based on the method for designing parallel handles of the present invention can correspond to the proximal side 470 of the distal part 450 of the parallel handle schematic 400 of the present invention.

Figure 10H:
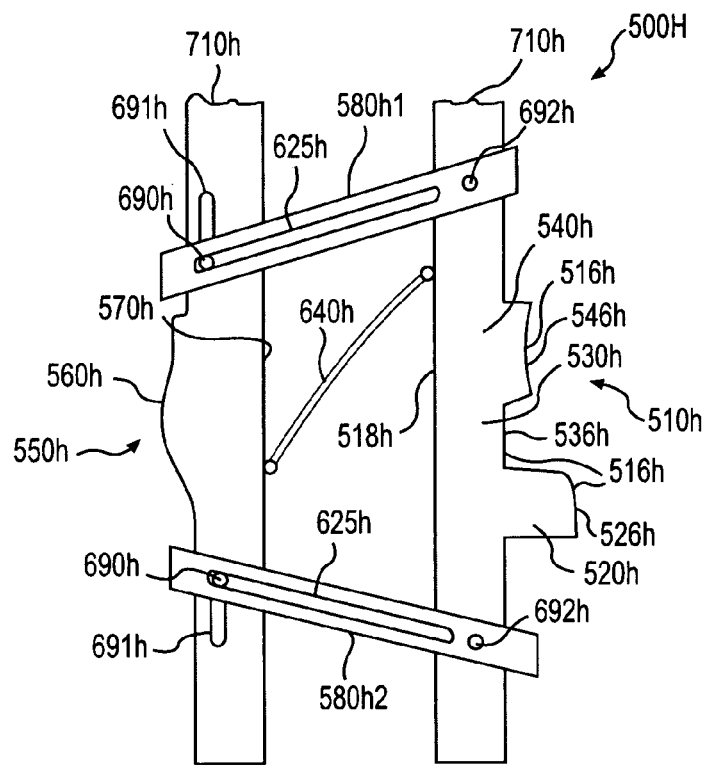

Continuing with reference to FIG. 10H another embodiment of a parallel handle 500H based on the design method of the present invention is illustrated. Similar to the parallel handle 500A of FIG. 10A, parallel handle 500H has a proximal moving member 510h and a distal moving member 550h, whereby the proximal side 536h of the middle section 530h of the proximal moving member 510h of the parallel handle 500H avoids contacting or putting undue pressure on the palm 102 in the area of CT 126 of the hand 100. The proximal moving member 510h and the distal moving member 550h of the parallel handle 500H based on the design method of the present invention correspond to the proximal part 410 and distal part 450 of the parallel handle schematic 400 of the present invention. The guide members 580h1 and 580h2 of the parallel handle 500H based on the design method of the present invention correspond to the radial contiguous line RCL and ulnar contiguous line UCL of the parallel handle schematic 400 of the present invention although, the guide members 580h1 and 580h2 are initially in skewed relation at a rest position for the parallel handle 500H. However, the guide members 580h1 and 580h2 slideably engage a pin member 690h in tracks 625h in the corresponding guide members 580h1 and 580h2 and the pin members 690h also slideably engage corresponding tracks 691h in the distal moving member 550h, and pin members 692h associated with the proximal moving member 510h pivotally engage with the corresponding guide members 580h1 and 580h2, to permit relative movement of the proximal moving member 510h and the distal moving member 550h.

Therefore, as shown in FIG. 10H, it is not necessary for the guide members 580h1 and 580h2 to always be in a parallel relation for parallel movement of the proximal moving member 510h and the distal moving member 550h of the parallel handle 500H based on the method for designing parallel handles of the present invention. However, as a hand 100 closes or opens while engaging the parallel handle 500H, the position and alignment of the guide members 580h1 and 580h2 in relation to each other promote stabilizing and maintaining alignment of the proximal moving member 510h and the distal moving member 550h of the parallel handle 500H. Such alignment promotes reducing MP joint 350 stress when the long fingers 200 of the hand 100 open or close.

Additionally, the parallel handle 500H has leaf spring 640h positioned between and engaging the proximal moving member 510h and the distal moving member 550h for control and biasing of the movement of the proximal moving member 510h and distal moving member 550h. Furthermore, the parallel handle 500H has a working end 710h on each of the proximal moving member 510h and the distal moving member 550h on which an implement, such as a scissors or pincers, can be attached to the parallel handle 500H.

The proximal moving member 510h of the parallel handle 500H in FIG. 10H based on the method for designing parallel handles of the present invention has an ulnar section 520h, a middle section 530h and a radial section 540h. The proximal moving member 510h of the parallel handle 500H based on the method for designing parallel handles of the present invention also has a proximal side 516h and a distal side 518h. The radial surface 546h of the radial section 540h of the proximal moving member 510h of the parallel handle 500H based on the method for designing parallel handles of the present invention corresponds to the proximal side 446 of the radial section 440 of the proximal part 410 of the parallel handle schematic 400 of the present invention. The middle surface 536h of the middle section 530h proximal moving member 510h of the parallel handle 500H based on the method for designing parallel handles of the present invention corresponds to the proximal surface 436 of the middle section 430 of the proximal part 410 of the parallel handle schematic 400 of the present invention. The ulnar surface 526h of the ulnar section 520h of the proximal moving member 510h of the parallel handle 500H based on the method for designing parallel handles of the present invention corresponds to the proximal side 426 of the ulnar section 420 of the proximal part 410 of the parallel handle schematic 400 of the present invention. The distal surface 518h of the proximal moving member 510h of the parallel handle 500H based on the method for designing parallel handles of the present invention corresponds to the distal side 418 of the proximal part 410 of the parallel handle schematic 400 of the present invention.

As illustrated in FIG. 10H, the distal moving member 550h of the parallel handle 500H based on the method for designing parallel handles of the present invention has a distal surface 560h and a proximal surface 570h. The distal surface 560h of the distal moving member 550h of the parallel handle 500H based on the method for designing parallel handles of the present invention corresponds to the distal side 460 of the distal part 450 of the parallel handle schematic 400 of the present invention. The proximal surface 570h of the distal moving member 550h of the parallel handle 500H based on the method for designing parallel handles of the present invention can correspond to the proximal side 470 of the distal part 450 of the parallel handle schematic 400 of the present invention.

Figure 10I:
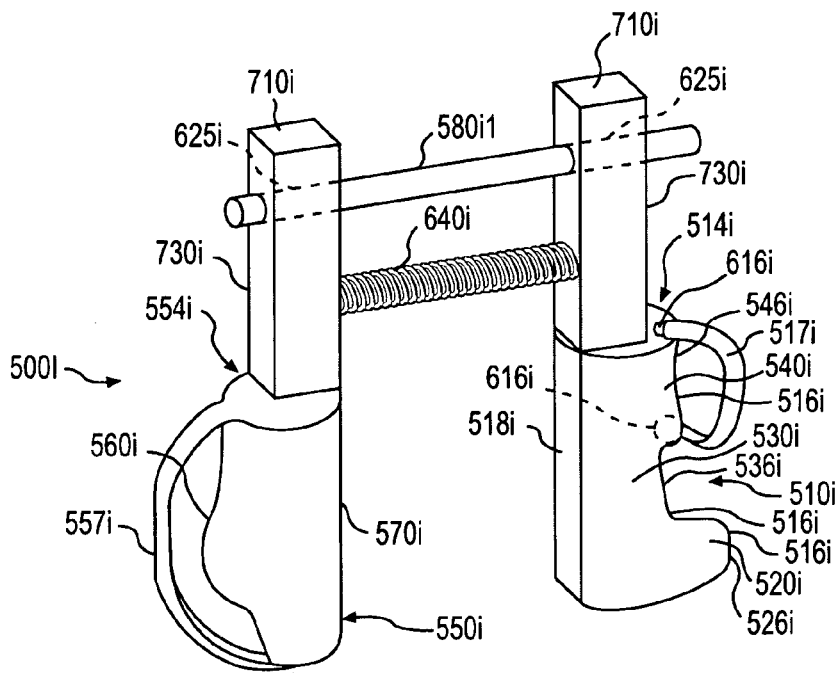

Continuing with reference to FIG. 10I another embodiment of a parallel handle 500I based on the design method of the present invention is illustrated. Similar to the parallel handle 500A of FIG. 10A, parallel handle 500I has a proximal moving member 510i and a distal moving member 550i, whereby the proximal side 536i of the middle section 530i of the proximal moving member 510i of the parallel handle 500I avoids contacting or putting undue pressure on the palm 102 in the area of CT 126 of the hand 100. The proximal moving member 510i and the distal moving member 550i of the parallel handle 500I based on the design method of the present invention correspond to the proximal part 410 and distal part 450 of the parallel handle schematic 400 of the present invention. The parallel handle 500I has a single guide member 580i1 that corresponds to the radial contiguous line RCL of the parallel handle schematic 400 of the present invention. However, the guide member 580i1 is positioned to the radial side 514i of the proximal moving member 510i and the radial side 554i of the parallel handle 500I and has a generally cylindrical shape. Also, the guide member 580i1 slideably engages a track 625i in the proximal moving member 510i and the distal moving member 550i to permit relative movement of the proximal moving member 510i and the distal moving member 550i. Additionally, the parallel handle 500I has coil spring 640i positioned between and engaging the proximal moving member 510i and the distal moving member 550i for control and biasing of the movement of the proximal moving member 510i and distal moving member 550i. Also, the proximal moving member 510i and the distal moving member 550i each have an integrally extending shaft member 730i at the corresponding radial sides 514i and 554i that engage with the guide member 580i1 and with the coil spring 640i. Furthermore, the parallel handle 500I has a working end 710i on each of the proximal moving member 510i and the distal moving member 550I contiguous with shaft members 730i on which an implement, such as a scissors or pincers, can be attached to the parallel handle 500I.

As illustrated in FIG. 10I, parallel handle 500I has a proximal ring member 517i for receiving the thumb 201 and is attached to the proximal moving member 510i. Furthermore, parallel handle 500I has a distal ring member 557i for receiving the long fingers 200 and is attached to the distal moving member 550i of the parallel handle 500I. The proximal ring member 517i for the thumb 201 can have be pivotally attached by pivot members 616i at the radial section 540I to allow the proximal ring member 517i to rotate relative to the proximal moving member 510i so as to receive either the right thumb 201 of the right hand 100 or the left thumb 201 of the left hand 100. The distal ring member 557i is attached at or integral with the radial end 554i and the ulnar end 552i of the distal moving member 550i for receiving the long fingers 200 of either the right hand 100 or the left hand 100. The proximal ring member 517i when engaged with the thumb 201 and the distal ring member 557i when engaged with the long fingers 200 of the hand 100 assist in spreading the proximal moving member 510i from the distal moving member 550i.

The proximal moving member 510i of the parallel handle 500I in FIG. 10I based on the method for designing parallel handles of the present invention has an ulnar section 520i, a middle section 530i and a radial section 540i. The proximal moving member 510i of the parallel handle 500I based on the method for designing parallel handles of the present invention also has a proximal side 516i and a distal side 518i. The radial surface 546i of the radial section 540i of the proximal moving member 510i of the parallel handle 500I based on the method for designing parallel handles of the present invention corresponds to the proximal side 446 of the radial section 440 of the proximal part 410 of the parallel handle schematic 400 of the present invention. The middle surface 536i of the middle section 530i proximal moving member 510i of the parallel handle 500I based on the method for designing parallel handles of the present invention corresponds to the proximal surface 436 of the middle section 430 of the proximal part 410 of the parallel handle schematic 400 of the present invention. The ulnar surface 526i of the ulnar section 520i of the proximal moving member 510i of the parallel handle 500I based on the method for designing parallel handles of the present invention corresponds to the proximal side 426 of the ulnar section 420 of the proximal part 410 of the parallel handle schematic 400 of the present invention. The distal surface 518i of the proximal moving member 510i of the parallel handle 500I based on the method for designing parallel handles of the present invention corresponds to the distal side 418 of the proximal part 410 of the parallel handle schematic 400 of the present invention.

As illustrated in FIG. 10I, the distal moving member 550i of the parallel handle 500I based on the method for designing parallel handles of the present invention has a distal surface 560i and a proximal surface 570i. The distal surface 560i of the distal moving member 550i of the parallel handle 500I based on the method for designing parallel handles of the present invention corresponds to the distal side 460 of the distal part 450 of the parallel handle schematic 400 of the present invention. The proximal surface 570i of the distal moving member 550i of the parallel handle 500I based on the method for designing parallel handles of the present invention can correspond to the proximal side 470 of the distal part 450 of the parallel handle schematic 400 of the present invention.

Figure 10J:
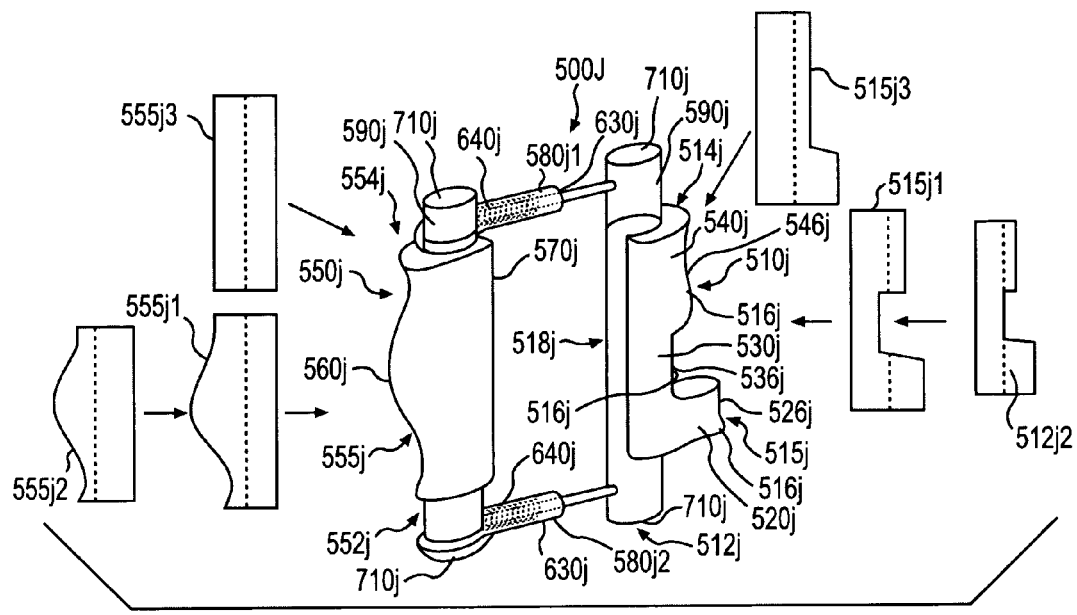

Continuing with reference to FIG. 10J, another embodiment of a parallel handle 500J based on the design method of the present invention is illustrated. Similar to the parallel handle 500A of FIG. 10A, parallel handle 500J has a proximal moving member 510j and a distal moving member 550j, whereby the proximal side 536j of the middle section 530j of the proximal moving member 510j of the parallel handle 500J avoids contacting or putting undue pressure on the palm 102 in the area of CT 126 of the hand 100. The proximal moving member 510j and the distal moving member 550j of the parallel handle 500J based on the design method of the present invention correspond to the proximal part 410 and distal part 450 of the parallel handle schematic 400 of the present invention. The guide members 580j1 and 580j2 of the parallel handle 500J based on the design method of the present invention correspond to the radial contiguous line RCL and ulnar contiguous line UCL of the parallel handle schematic 400 of the present invention. However, the guide members 580j1 and 580j2 are respectively positioned to the radial side 514j and to the ulnar side 512j of the proximal moving member 510j and are respectively positioned to the radial side 554j and to the ulnar side 552j of the distal moving member 550j. Also, the guide member 580j1 and 580*j*2 each have a telescoping device 630*j* to permit relative movement of the proximal moving member 510*j* and the distal moving member 550*j*, and the telescoping device 630*j* can also include a coil spring 640*j* for control and biasing of the movement of the distal moving member 510*j* and proximal moving member 550*j*.

Additionally, referring to FIG. 10J, the parallel handle 500J can have a plurality of replaceable proximal moving members 515*j* and a plurality of replaceable distal moving members 555*j* paired in different sizes so as to engage respective receiving members 590*j* to respectively form the proximal moving member 510*j* and the distal moving member 550*j* for a parallel handle 500J so as to accommodate a plurality of hand sizes for use with a particular device. These replaceable moving members 515*j*, 555*j* based on the method for designing parallel handles of the present invention are interchangeable and can slide, snap, bolt, latch or have other means to connect to the shafts or receiving members 590*j*.

FIG. 10J illustrates a plurality of replaceable proximal moving members 515*j*, such as replaceable proximal moving members 515*j*1, 515*j*2 and 515*j*3, and also illustrates a plurality of replaceable distal moving members 555*j*, such as replaceable proximal moving members 555*j*1, 555*j*2 and 555*j*3. For example, the replaceable proximal moving members 515*j*1 and 515*j*2 are of a similar configuration, but of a different size, and with the replaceable proximal moving member 515*j*1 being paired with the similar size replaceable distal moving member 555*j*1 and with the replaceable proximal moving member 515*j*2 being paired with the similar size replaceable distal moving member 555*j*2.

Further, replaceable proximal moving member 515*j*3 is paired with replaceable distal moving member 555*j*3 which are of a different configuration than the replaceable proximal moving members 515*j*1 and 515*j*2 and the replaceable distal moving members 555*j*1 and 555*j*2. The configuration of the replaceable proximal moving member 515*j*3 is illustrative of configurations for the replaceable proximal moving member 515*j* where distance D', as illustrated in FIG. 10B, can vary so to be equal to or less than distance C' and still avoid contacting or putting undue pressure on the "carpal tunnel zone" CTZ for certain designs of parallel handles, such as the distance D" in FIG. 10B. Furthermore, replaceable distal moving member 555*j*3 can be of any suitable shape or configuration, other than conforming to the curve 310 of the finger cup 108 of the hand 100, such as of a cylindrical, oval or rectangular shape.

The receiving members 590*j* can be of any suitable shape or pattern for receiving the replaceable proximal moving members 515*j* and replaceable distal moving members 555*j* such as for example a circular, oval, square, rectangular or other cross-sectional pattern or shape. Also, the receiving members 590*j* can each have an integral working end 710*j* on each of the proximal moving member 510*j* and the distal moving member 550*j* on which an implement, such as a scissors or pincers, can be attached to the parallel handle 500J.

The proximal moving member 510*j* of the parallel handle 500J in FIG. 10J based on the method for designing parallel handles of the present invention has an ulnar section 520*j*, a middle section 530*j* and a radial section 540*j*. The proximal moving member 510*j* of the parallel handle 500J based on the method for designing parallel handles of the present invention also has a proximal side 516*j* and a distal side 518*j*. The radial surface 546*j* of the radial section 540*j* of the proximal moving member 510*j* of the parallel handle 500J based on the method for designing parallel handles of the present invention corresponds to the proximal side 446 of the radial section 440 of the proximal part 410 of the parallel handle schematic 400 of the present invention. The middle surface 536*j* of the middle section 530*j* proximal moving member 510*j* of the parallel handle 500J based on the method for designing parallel handles of the present invention corresponds to the proximal surface 436 of the middle section 430 of the proximal part 410 of the parallel handle schematic 400 of the present invention. The ulnar surface 526*j* of the ulnar section 520*j* of the proximal moving member 510*j* of the parallel handle 500J based on the method for designing parallel handles of the present invention corresponds to the proximal side 426 of the ulnar section 420 of the proximal part 410 of the parallel handle schematic 400 of the present invention. The distal surface 518*e* of the proximal moving member 510*j* of the parallel handle 500J based on the method for designing parallel handles of the present invention corresponds to the distal side 418 of the proximal part 410 of the parallel handle schematic 400 of the present invention.

As illustrated in FIG. 10J, the distal moving member 550*j* of the parallel handle 500J based on the method for designing parallel handles of the present invention has a distal surface 560*j* and a proximal surface 570*j*. The distal surface 560*j* of the distal moving member 550*j* of the parallel handle 500J based on the method for designing parallel handles of the present invention corresponds to the distal side 460 of the distal part 450 of the parallel handle schematic 400 of the present invention. The proximal surface 570*j* of the distal moving member 550*j* of the parallel handle 500J based on the method for designing parallel handles of the present invention can correspond to the proximal side 470 of the distal part 450 of the parallel handle schematic 400 of the present invention.

Figure 10K:
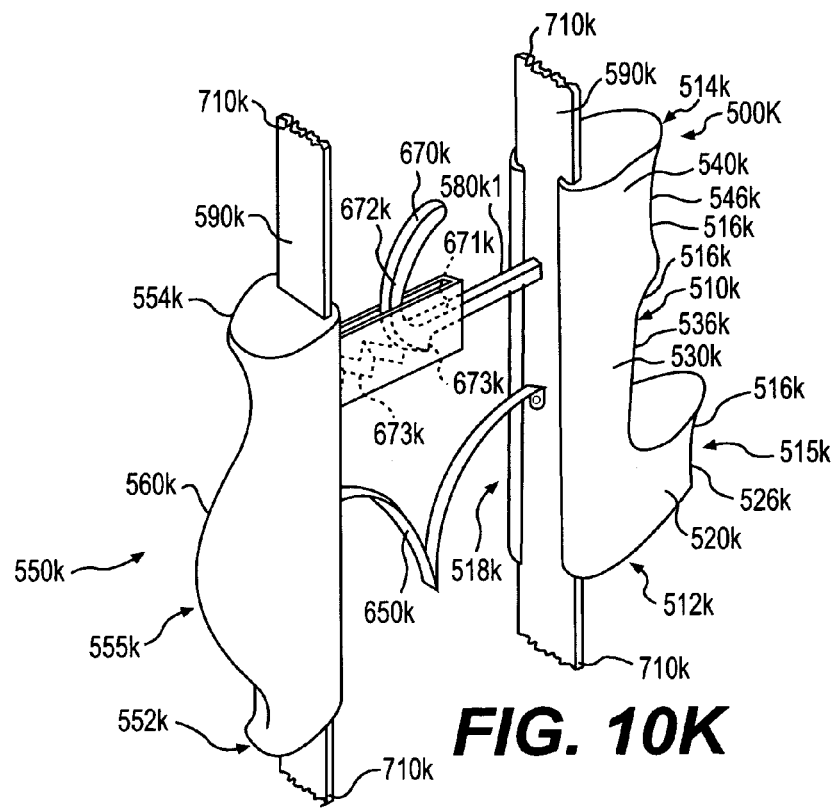

Continuing with reference to FIG. 10K another embodiment of a parallel handle 500K based on the design method of the present invention is illustrated. Similar to the parallel handle 500A of FIG. 10A, parallel handle 500K has a proximal moving member 510*k* and a distal moving member 550*k*, whereby the proximal side 536*k* of the middle section 530*k* of the proximal moving member 510*k* of the parallel handle 500K avoids contacting or putting undue pressure on the palm 102 in the area of CT 126 of the hand 100. The proximal moving member 510*k* and the distal moving member 550*k* of the parallel handle 500K based on the design method of the present invention correspond to the proximal part 410 and distal part 450 of the parallel handle schematic 400 of the present invention. The guide members 580*k*1 of the parallel handle 500K based on the design method of the present invention corresponds to the radial contiguous line RCL of the parallel handle schematic 400 of the present invention. However, the guide member 580*k*1 is positioned between the radial end 514*k* and the ulnar end 512*k* of the proximal moving member 510*k* and positioned between the radial end 554*k* and the ulnar end of 552*k* of the distal moving member 550*k*. Also, the guide member 580*k*1 has a locking device 670*k* including a track 671*k* that engages with a ratchet member 672*k* to selectively lock or retain the parallel handle 500K at one or more predetermined positions 673*k*. The parallel handle 500K can also include a leaf spring 650*k* for control and biasing of the movement of the distal moving member 510*k* and proximal moving member 550*k*.

Additionally, similar to the parallel handle 500J of FIG. 10J, the parallel handle 500K can have a plurality of replaceable proximal moving members 515*k* and a plurality of replaceable distal moving members 555*k* paired in different sizes so as to engage respective receiving members 590*k* to respectively form the proximal moving member 510*k* and the distal moving member 550*k* for a parallel handle 500K so as to accommodate a plurality of hand sizes for use with a particular device. These replaceable moving members 515*k*, 555*k* based on the method for designing parallel handles of the present invention are interchangeable and can slide, snap, bolt, latch or have other means to connect to the shafts or receiving members 590*k*.

The receiving members 590*k* can be of any suitable shape or pattern for receiving the replaceable proximal moving members 515*k* and replaceable distal moving members 555*k* such as for example a circular, oval, square, rectangular or other cross-sectional pattern or shape, with the receiving members 590*k* being of a generally rectangular shape in the parallel handle 500K. Also, the receiving members 590*k* can each have an integral working end 710*k* on each of the proximal moving member 510*k* and the distal moving member 550*k* on which an implement, such as a scissors or pincers, can be attached to the parallel handle 500K.

The proximal moving member 510*k* of the parallel handle 500K in FIG. 10K based on the method for designing parallel handles of the present invention has an ulnar section 520*k*, a middle section 530*k* and a radial section 540*k*. The proximal moving member 510*k* of the parallel handle 500K based on the method for designing parallel handles of the present invention also has a proximal side 516*k* and a distal side 518*k*. The radial surface 546*k* of the radial section 540*k* of the proximal moving member 510*k* of the parallel handle 500K based on the method for designing parallel handles of the present invention corresponds to the proximal side 446 of the radial section 440 of the proximal part 410 of the parallel handle schematic 400 of the present invention. The middle surface 536*k* of the middle section 530*k* proximal moving member 510*k* of the parallel handle 500K based on the method for designing parallel handles of the present invention corresponds to the proximal surface 436 of the middle section 430 of the proximal part 410 of the parallel handle schematic 400 of the present invention. The ulnar surface 526*k* of the ulnar section 520*k* of the proximal moving member 510*k* of the parallel handle 500K based on the method for designing parallel handles of the present invention corresponds to the proximal side 426 of the ulnar section 420 of the proximal part 410 of the parallel handle schematic 400 of the present invention. The distal surface 518*k* of the proximal moving member 510*k* of the parallel handle 500K based on the method for designing parallel handles of the present invention corresponds to the distal side 418 of the proximal part 410 of the parallel handle schematic 400 of the present invention.

As illustrated in FIG. 10K, the distal moving member 550*k* of the parallel handle 500K based on the method for designing parallel handles of the present invention has a distal surface 560*k* and a proximal surface 570*k*. The distal surface 560*k* of the distal moving member 550*k* of the parallel handle 500K based on the method for designing parallel handles of the present invention corresponds to the distal side 460 of the distal part 450 of the parallel handle schematic 400 of the present invention. The proximal surface 570*k* of the distal moving member 550*k* of the parallel handle 500K based on the method for designing parallel handles of the present invention can correspond to the proximal side 470 of the distal part 450 of the parallel handle schematic 400 of the present invention.

Continuing with reference to FIG. 10L1 and 10L2, two further embodiments of parallel handles 500L1 and 500L2 based on the design method of the present invention are illustrated. Similar to the parallel handle 500A of FIG. 10A, parallel handles 500L1 and 500L2 each have a proximal moving member 510*l* and a distal moving member 550*l*, whereby the proximal side 536*l* of the middle section 530*l* of the proximal moving member 510*l* of each of the parallel handles 500L1 and 500L2 avoids contacting or putting undue pressure on the palm 102 in the area of CT 126 of the hand 100. The proximal moving member 510*l* and the distal moving member 550*l* of the parallel handles 500L1 and 500L2 based on the design method of the present invention correspond to the proximal part 410 and distal part 450 of the parallel handle schematic 400 of the present invention. The guide members 580/1 and 580/2 of each of the parallel handles 500L1 and 500L2 based on the design method of the present invention correspond to the radial contiguous line RCL and ulnar contiguous line UCL of the parallel handle schematic 400 of the present invention. However, the guide members 580/1 and 580/2 are positioned between the radial end 514*l* and the ulnar end 512*l* of the proximal moving member 510*l* and positioned between the radial end 554*l* and the ulnar end of 552*l* of the distal moving member 550*l*. Also, the guide members 58011 and 580/2 each have a telescoping device 630*l* to permit relative movement of the proximal moving member 510*l* and the distal moving member 550*l*. Further, a spring 660*l* can be positioned between the proximal moving member 510*l* and the distal moving member 550*l* for control and biasing of the movement of the distal moving member 510*l* and proximal moving member 550*l*.

The proximal moving member 510*l* of the parallel handles 500L1 and 500L2 in FIGS. 10L1 and 10L2 based on the method for designing parallel handles of the present invention has an ulnar section 520*l*, a middle section 530*l* and a radial section 540*l*. The proximal moving member 510*l* of each of the parallel handles 500L1 and 500L2 based on the method for designing parallel handles of the present invention also has a proximal side 516*l* and a distal side 518*l*. The radial surface 546*l* of the radial section 540*l* of the proximal moving member 510*l* of each of the parallel handle 500L1 and 500L2 based on the method for designing parallel handles of the present invention corresponds to the proximal side 446 of the radial section 440 of the proximal part 410 of the parallel handle schematic 400 of the present invention. The middle surface 536*l* of the middle section 530*l* proximal moving member 510*l* of each of the parallel handles 500L1 and 500L2 based on the method for designing parallel handles of the present invention corresponds to the proximal surface 436 of the middle section 430 of the proximal part 410 of the parallel handle schematic 400 of the present invention. The ulnar surface 526*l* of the ulnar section 520*l* of the proximal moving member 510*l* of each of the parallel handles 500L1 and 500L2 based on the method for designing parallel handles of the present invention corresponds to the proximal side 426 of the ulnar section 420 of the proximal part 410 of the parallel handle schematic 400 of the present invention. The distal surface 518*l* of the proximal moving member 510*l* of each of the parallel handles 500L1 and 500L2 based on the method for designing parallel handles of the present invention corresponds to the distal side 418 of the proximal part 410 of the parallel handle schematic 400 of the present invention.

Also, the proximal moving member 510*l* and the distal moving member 550*l* can each have an integral working end 710*l* on which an implement, such as a scissors or pincers, can be attached to the parallel handles 500L1 and 500L2. However, in the embodiment of the parallel handle 500L1 of FIG. 10L1 the integral working ends 710/1 project inwardly with respect to the proximal moving member 510*l* and the distal moving member 550*l* and, in the embodiment of the parallel handle 500L2 of FIG. 10L2 the integral working ends 710*l*2 project outwardly with respect to the proximal moving member 510*l* and the distal moving member 550*l*.

As illustrated in FIGS. 10L1 and 10L2, the distal moving member 550*l* of each of the parallel handles 500L1 and 500L2 based on the method for designing parallel handles of the present invention has a distal surface 560*l* and a proximal surface 570*l*. The distal surface 560*l* of the distal moving member 550*l* of each of the parallel handles 500L1 and 500L2 based on the method for designing parallel handles of the present invention corresponds to the distal side 460 of the distal part 450 of the parallel handle schematic 400 of the present invention. The proximal surface 570*l* of the distal moving member 550*l* of each of the parallel handles 500L1 and 500L2 based on the method for designing parallel handles of the present invention can correspond to the proximal side 470 of the distal part 450 of the parallel handle schematic 400 of the present invention.

Figure 10M:
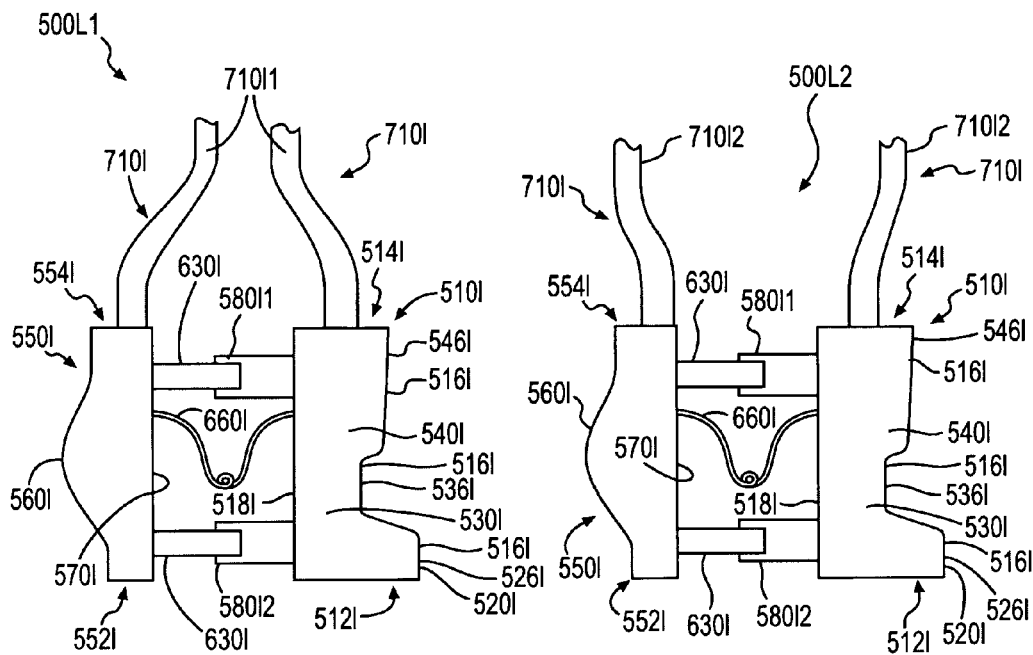
Figure 10M:
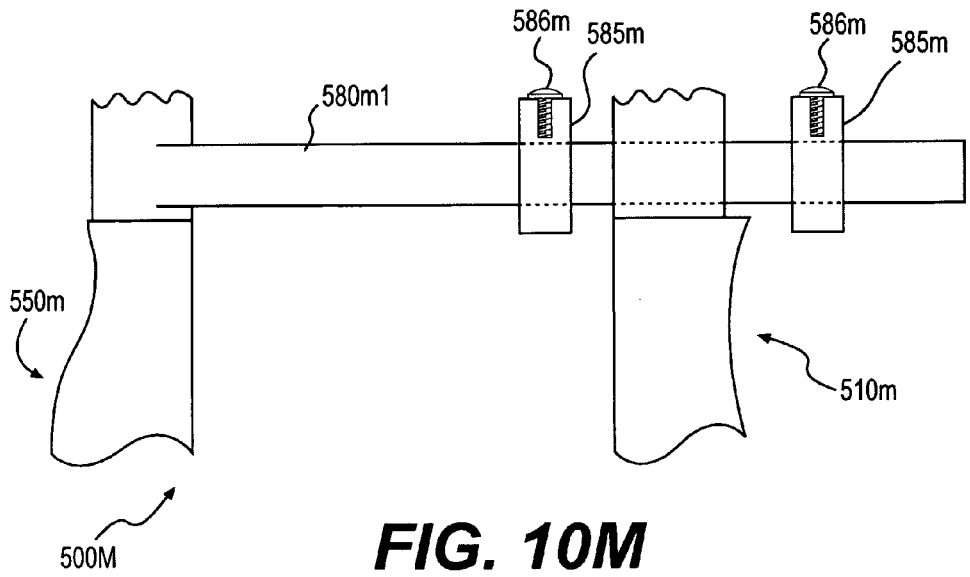

FIG. 10M illustrates a schematic of a parallel handle 500M that can correspond to any of the parallel handles 500A through 500L2 of the present invention that illustrate stops 585*m* attached to a guide member 580*m*1 that functions to limit movement of the proximal moving member 510*m* or the distal moving member 550*m* in relation to each other. The stops 585*m* slideably engage the guide member 580*m*1 and have locking means, such as screws 586*m*, to fix the stops at various positions on the guide member 580*m*1 to limit movement of the proximal moving member 510*m* or the distal moving member 550*m* within a predetermined range of movement.

Figure 11:
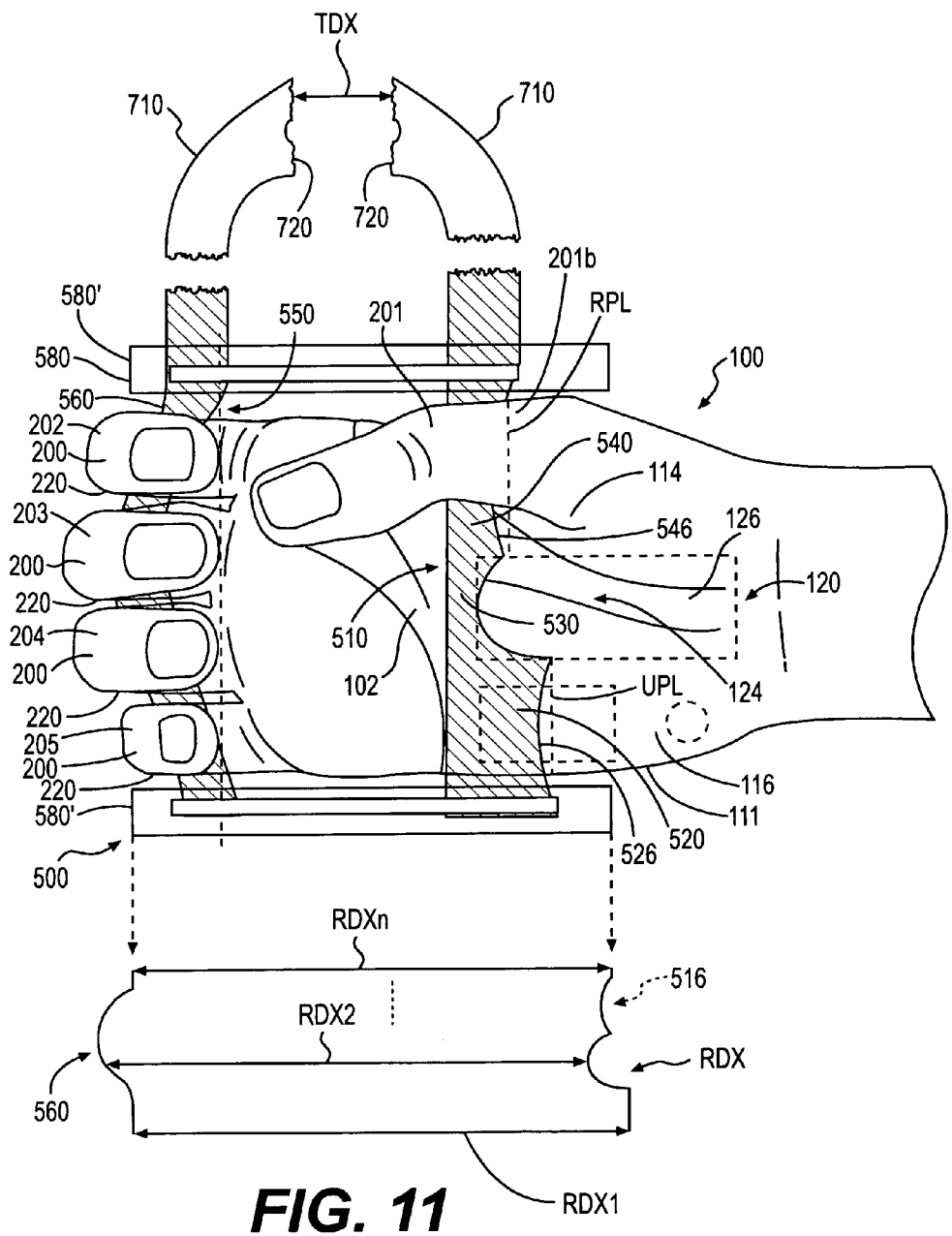
FIG. 11 is a view illustrating the hand contacting an embodiment of a parallel handle of the present invention.

Referring now to FIG. 11, as well as to FIG. 9, FIG. 11 is a schematic view illustrating the hand 100 in engaging relation with a parallel handle 500 of the present invention. Also, FIG. 9 and FIG. 11 relate the parallel handle 500 to the hand 100 in relation to the parallel handle schematic 400 based on the method for designing parallel handles of the present invention.

Continuing with reference to FIGS. 9 and 11, the palm 102 of the hand 100 meets the proximal moving member 510 of the parallel handle 500. Specifically, the thenar muscle area 114 of the palm 102 of the hand 100 contacts the radial surface 546 of the radial section 540 of the proximal moving member 510 of the parallel handle 500 based on the method for designing parallel handles of the present invention at or near the radial palmar line RPL at the base 201*b* of the thumb 201 of the hand 100. The hypothenar muscle area 116 of the palm 102 of the hand 100 contacts the ulnar surface 526 of the ulnar section 520 of the proximal moving member 510 of the parallel handle 500 based on the method for designing parallel handles of the present invention at or near the ulnar palmar line UPL on the ulnar side 111 of the hand 100. The recessed middle section 530 of the proximal moving member 510 of the parallel handle 500 based on the method for designing parallel handles of the present invention avoids contacting or placing undue pressure on the area at CT 126 of the palm 102 of the hand 100.

As further illustrated in FIGS. 9 and 11, the long fingers 200 of the hand 100 contact the distal moving member 550 of the parallel handle 500 based on the method for designing parallel handles of the present invention. Specifically, the inner surface 212 of the middle segment 220 of the index finger 202 of the hand 100 contacts the radial section RS' of the distal moving member 550 of the parallel handle 500 based on the method for designing parallel handles of the present invention. The inner surface 213 of the middle segment 220 of the long finger 203 of the hand 100 contacts the radial section RS' and the middle section MS' of the distal moving member 550 of the parallel handle 500 based on the method for designing parallel handles of the present invention. The inner surface 214 of the middle segment 220 of the ring finger 204 of the hand 100 contacts the middle section MS' and the ulnar section US' of the distal moving member 550 of the parallel handle 500 based on the method for designing parallel handles of the present invention. The inner surface 215 of the middle segment 220 of the small finger 205 of the hand 100 contacts the ulnar section US' of the distal moving member 550 of the parallel handle 500 based on the method for designing parallel handles of the present invention.

Therefore, referring to FIGS. 9 and 11, squeezing a parallel handle 500 based on the method for designing parallel handles of the present invention transmits pressure to underlying bones at the thenar muscle area 114 and the hypothenar muscle area 116 of the palm 102 of the hand 100. Furthermore, squeezing a parallel handle 500 based on the method for designing parallel handles of the present invention transmits pressure to underlying bones and soft tissue of the middle segments 220 of the long fingers 200 of the hand 100. However, squeezing a parallel handle 500 based on the method for designing parallel handles of the present invention can substantially prevent undue direct pressure from being applied to the transverse carpal ligament 124, the underlying median nerve 126*a*, superficial flexor tendons 126*b* or deep flexor tendons 126*c* in the CT 126 of the wrist 120.

Further, the cross-sectional shape of the proximal moving member 510, distal moving member 550, and guide members 580 and 580' can vary depending upon the use and design of a handle 500 based on the method for designing parallel handles of the present invention, such as illustrated in FIGS. 10A through 10M. The proximal moving member 510, distal moving member 550 and guide members 580 and 580' can have a variety of surface characteristics, such rough or smooth or variations thereof, and can be formed or fabricated of various substances and materials, such as a wood material, a plastic material, a metal material or a composite material.

Continuing with reference to FIGS. 9 and 11, as well as with reference to FIGS. 1 through 8, the hand 100 moves through a range of motion while contacting a parallel handle 500 when the proximal moving member 510 and the distal moving member 550 or the proximal moving member moves relatively to the other member. The positions of the distal moving member 550 and the proximal moving member 510 as the hand 100 correspondingly moves relate to corresponding distance movement ranges between the Spread T Position STP and Closed T Position CTP.

As shown in the radial views of the hand 100 in FIG. 2, FIG. 4 and FIG. 6, line A and line B relate to and diagrammatically illustrate the relative position of the hand 100 engaging a parallel handle 500 as the hand 100 moves from the Spread T Position STP to the T Position to the Closed T Position CTP or from Closed T Position CTP to the T Position to the Spread T Position STP the when the hand 100 is positioned as in FIG. 9 and FIG. 11. Line A extends from the base 201*b* of the thumb 201 in the area of the radial palmar line RPL to the curve 310 of the finger cup 108 along the inner surfaces 212, 213, 214, 215 of the middle segments 220 of long fingers 200 of the hand 100. Line B extends from the area of the ulnar palmar line UPL on the hypothenar muscle area 116 to the curve 310 of the finger cup 108 along the inner surfaces 212, 213, 214, 215 of the middle segments 220 of long fingers 200 of the hand 100.

FIG. 11 also diagrammatically illustrates an example for a range of the reach distance RDX. The reach distance RDX is a linear measurement that extends from a point on the distal moving member 560 of the distal moving member 550 to a corresponding point on the proximal side 516 of the proximal moving member 510. FIG. 11 illustrates a plurality of reach distances, RDX1 through RDXn, for a parallel handle 500 when the parallel handle 100 is at a predetermined position. Further, the reach distance RDX varies with the movement of the hand 100 on the parallel handle 500 from either the Spread T Position STP to the T Position, the T Position to the Closed T Position CTP or the Spread T Position STP to the Closed T Position CTP and can correspond to Distance E, Distance F or Distance G with reference to FIG. 7. Reach distance RD can be a factor for consideration in determining the sizes, shapes and properties of handles for tools or implements based on the method for designing parallel handles of the present invention.

FIG. 11 illustrates the travel distance TDX for an embodiment of the parallel handle 500, such as for pliers-type tools, and can be related to the closure requirements of the working ends of tools utilizing a parallel handle based on the method for designing parallel handles of the present invention. Referring to FIG. 11, the travel distance TDX is a linear measurement that extends from a point on one facing part 720 of a working end 710 to a corresponding point on the other facing part 720 of the other working end 710 of a pliers-type tool with a parallel handle 500. The travel distance TDX can therefore be measured at any one of various points and corresponding points on the facing part 720 and can also be measured at various positions of the working ends 710 that extend within a range of the open and closed position for the working ends 710. The travel distance TDX can relate to the function or the use of a working end 710 with a particular embodiment of a parallel handle 500.

Also, with reference to FIG. 11, as well as to FIG. 7, measurements for hand width W, as diagrammatically illustrated in FIG. 7, can be used to determine various sizes for parallel handles 500. Multiple sizes of parallel handles 500, related to width W, can be made to accommodate various hand sizes that can provide a more comfortable, better fitting parallel handle according to the present invention.

Figure 12A:
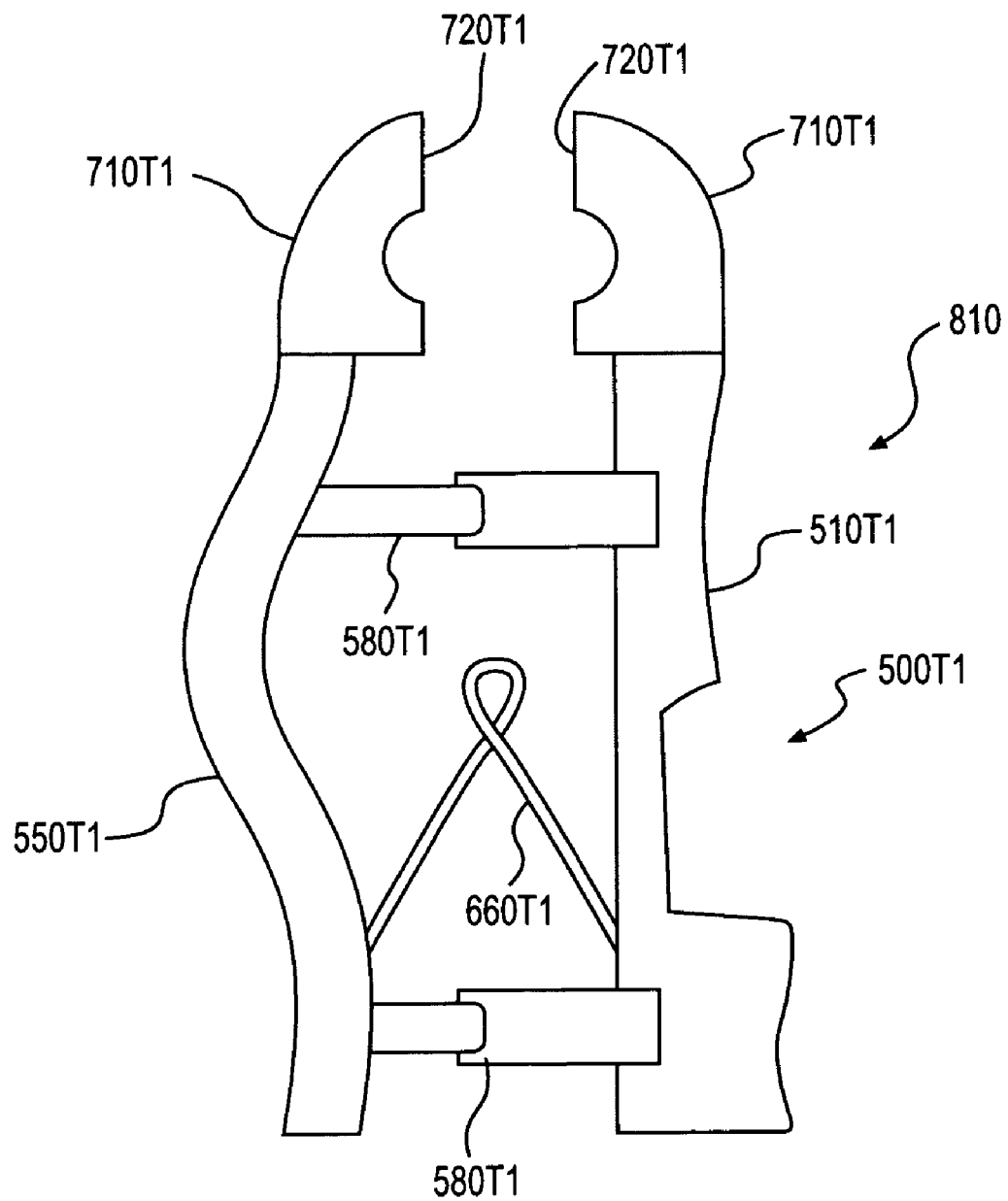

FIG. 12A illustrates an example of a pliers-type tool 810 with a parallel handle 500T1 similar to parallel handles 500L1 and 500L2. The parallel handle 500T1 of pliers-type tool 810 has a proximal moving member 510T1 and a distal moving member 550T1 and has two telescoping guide members 580T1 with a spring 660T1. The pliers-type tool 810 has two opposing facing parts 720T1 at the working ends 710T1. The working ends 710T1 extend from the proximal moving member 510T1 and the distal moving member 550T1.

Figure 12B:
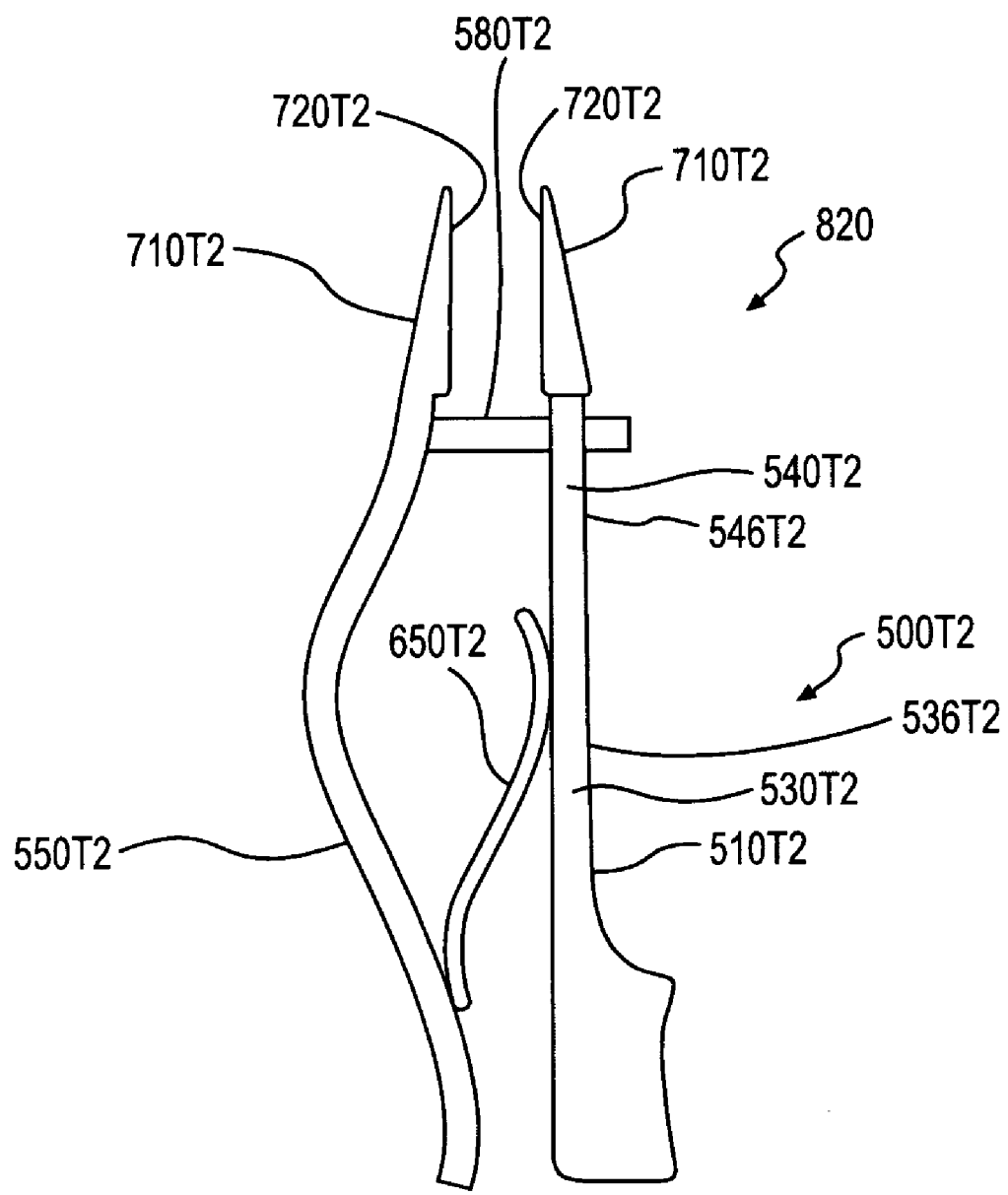
FIG. 12B illustrates an embodiment of a parallel handle of the present invention for use as fine pliers.

FIG. 12B illustrates another example of a pliers-type tool 820 with a parallel handle 500T2 similar to parallel handles 500F and 500I. The parallel handle 500T2 of pliers-type tool 820 has a proximal moving member 510T2 and a distal moving member 550T2 and has a single guide member 580T2 and a leaf spring 650T2. The pliers-type tool 810 has two opposing facing parts 720T2 at the working ends 710T2. The opposing facing parts 720T2 of the working ends 710T2 are tapered, such as to hold or grasp small objects. The working ends 710T2 extend from the proximal moving member 510T2 and the distal moving member 550T2. Further, FIG. 12B illustrates an example where, as discussed with respect to FIG. 10B, the distance D' can vary so to be equal to or less than distance C' and still avoid contacting or putting undue pressure on the "carpal tunnel zone" CTZ. In FIG. 12B the radial surface 546T2 of the radial section 540T2 and the middle surface 536T2 of the middle section 530T2 are in linear alignment such that the distance D' is less than the distance C', and the middle surface 536T2 of the middle section 530T2 of the proximal moving member 510T2 avoids contacting or putting undue pressure on the "carpal tunnel zone" CTZ.

Figure 12C:
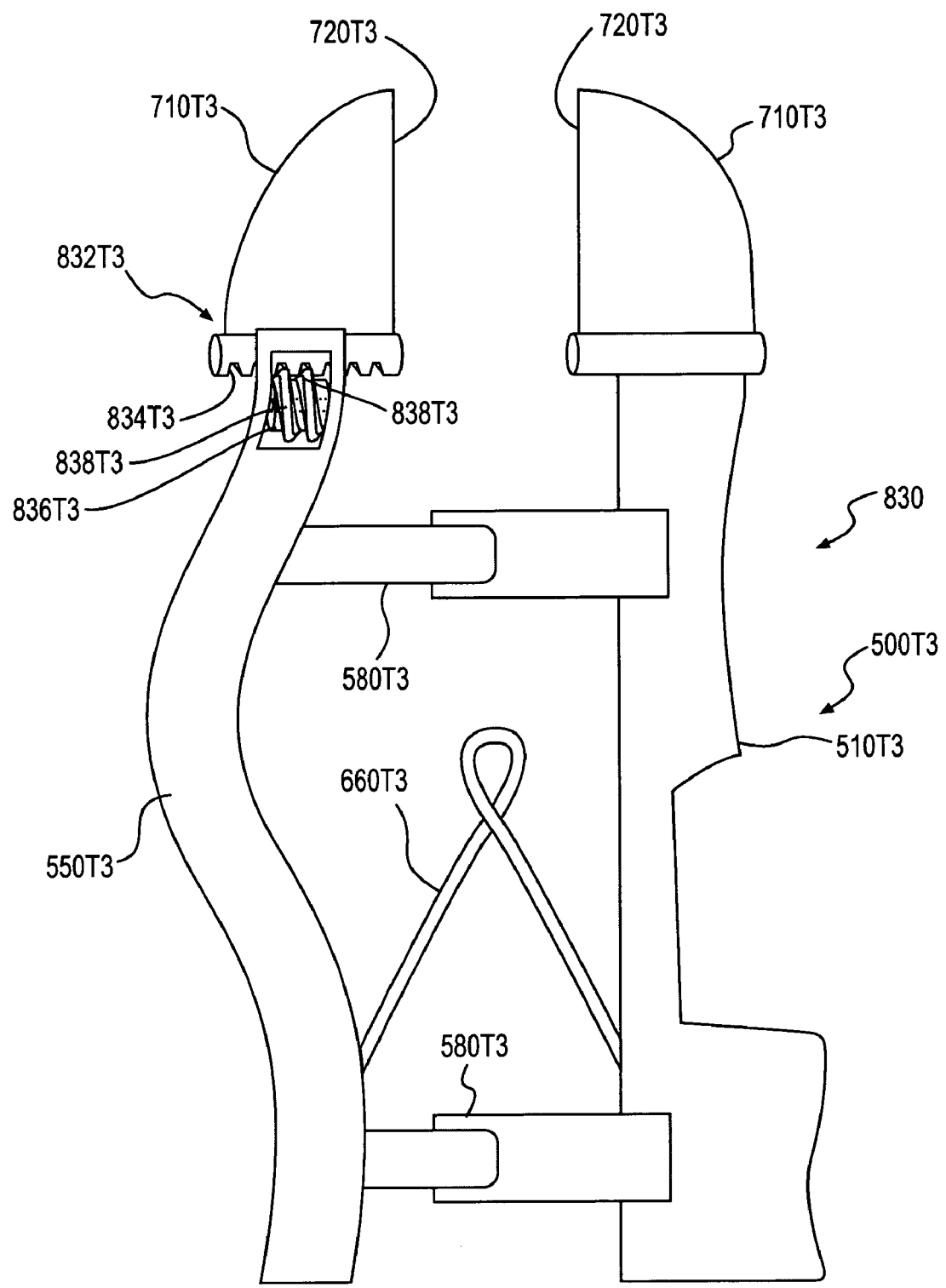
FIG. 12C illustrates an embodiment of a parallel handle of the present invention use as pliers with an adjustable working member.

FIG. 12C illustrates an example an adjustable pliers-type tool 830 with a parallel handle 500T3 similar to parallel handles 500L1 and 500L2. The parallel handle 500T3 of pliers-type tool 830 has a proximal moving member 510T3 and a distal moving member 550T3 and has two telescoping guide members 580T3 with a spring 660T3. The pliers-type tool 810 has two opposing facing parts 720T3 at the working ends 710T3. One of the working ends 710T3 has an adjustable working member 832T3. In this adjustable pliers type-tool 830 one or both of the working ends 710T3 can have an adjustable working end 832T3 in which one or both working ends 710T3 can be moved to different positions along a toothed track 834T3 by engaging elevations 838T3 on a rotating cylinder 836T3.

Figure 12D:
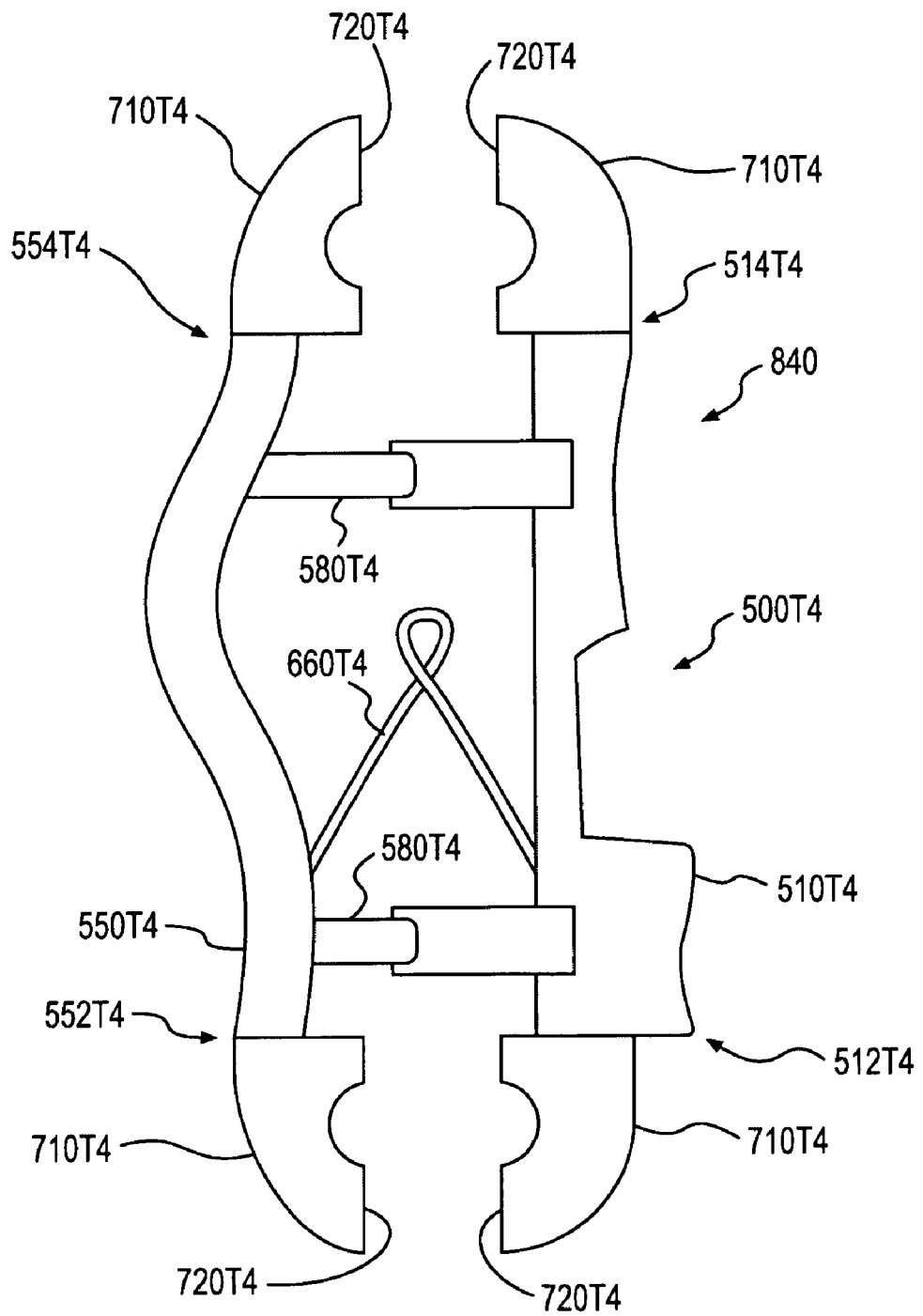
FIG. 12D illustrates an embodiment of a parallel handle of the present invention having two working ends.

FIG. 12D illustrates an example of a pliers-type tool 840 with a parallel handle 500T4 similar to parallel handles 500L1 and 500L2. The parallel handle 500T4 of pliers-type tool 840 has a proximal moving member 510T4 and a distal moving member 550T4 and has two telescoping guide members 580T4 with a spring 660T4. The pliers-type tool 810 has four opposing facing parts 720T4 at the working ends 710T4 at each of the radial side 514T4 and ulnar side 512T4 of the proximal moving member 510T4 and the radial side 554T4 and ulnar side 552T4 of the distal moving member 550T4. The working ends 710T4 do not necessarily have to be the same as to shape, size or function.

Figure 12E:
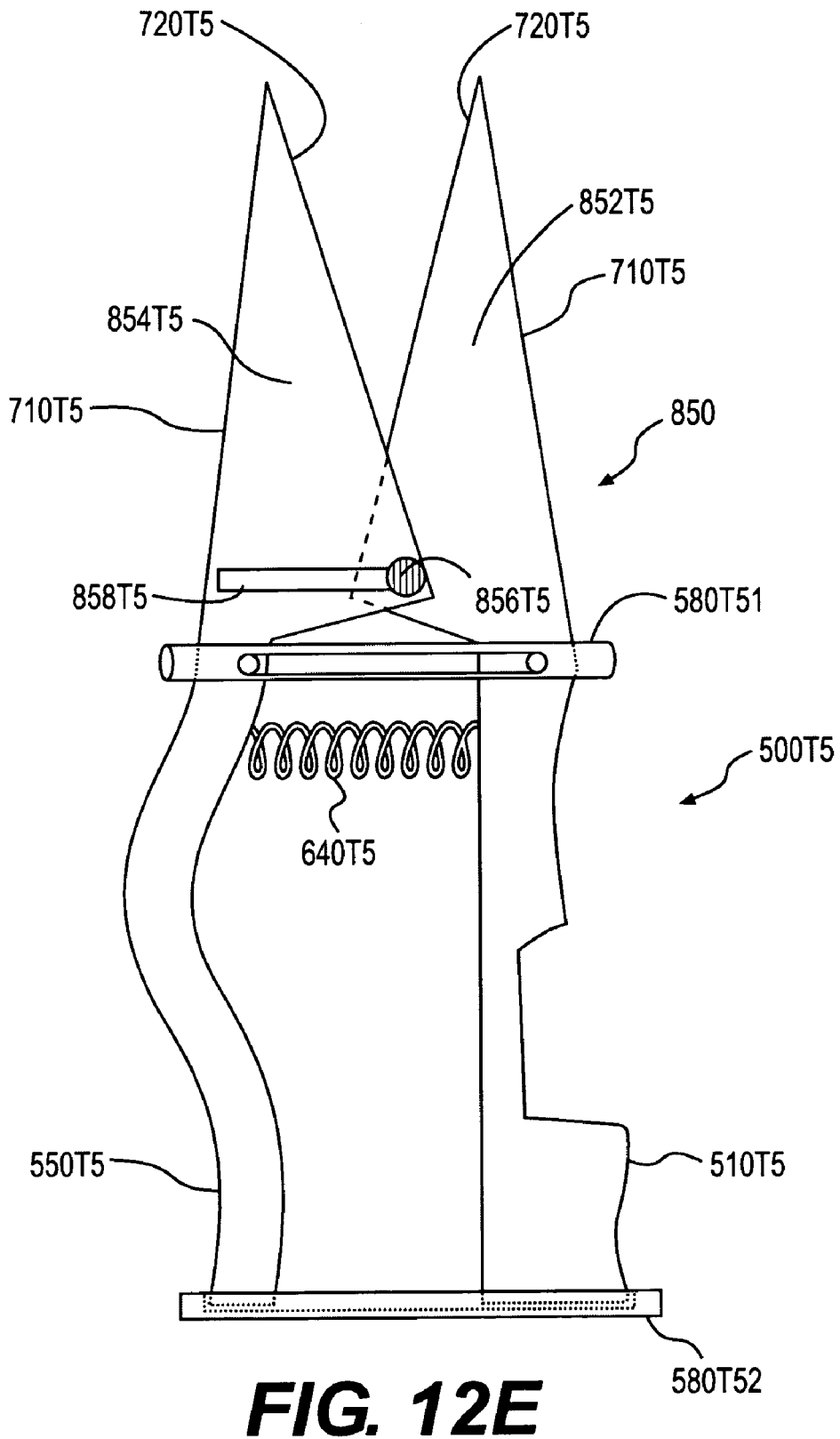
FIG. 12E illustrates an embodiment of a parallel handle of the present invention being a shears.

FIG. 12E illustrates an example of a shears pliers-type tool 850 with a parallel handle 500T5 similar to parallel handle 500A. The parallel handle 500T5 of pliers-type tool 850 has a proximal moving member 510T5 and a distal moving member 550T5 and has two guide members 580T51 and 585T52 with a coil spring 640T5. The pliers-type tool 850 has two opposing facing parts 720T5 at the working ends 710T5. The shears pliers-type tool 850 has one blade 852T5 attached to a proximal moving member 510T5 and another blade 854T5 attached to a distal moving member 550T5. The blades 852T5 and 854T5 slide toward each other to cut objects when the distal moving member 550T5 moves toward the proximal moving member 510T5. The sliding movement is facilitated by a tab 856T5 on blade 854T5 which engages with a guide track 858T5 on blade 852T5, and the tab 856T5 engaging with the guide track 858T5 can also serve to connect blade 852T5 to blade 854T5.

Figure 12F:
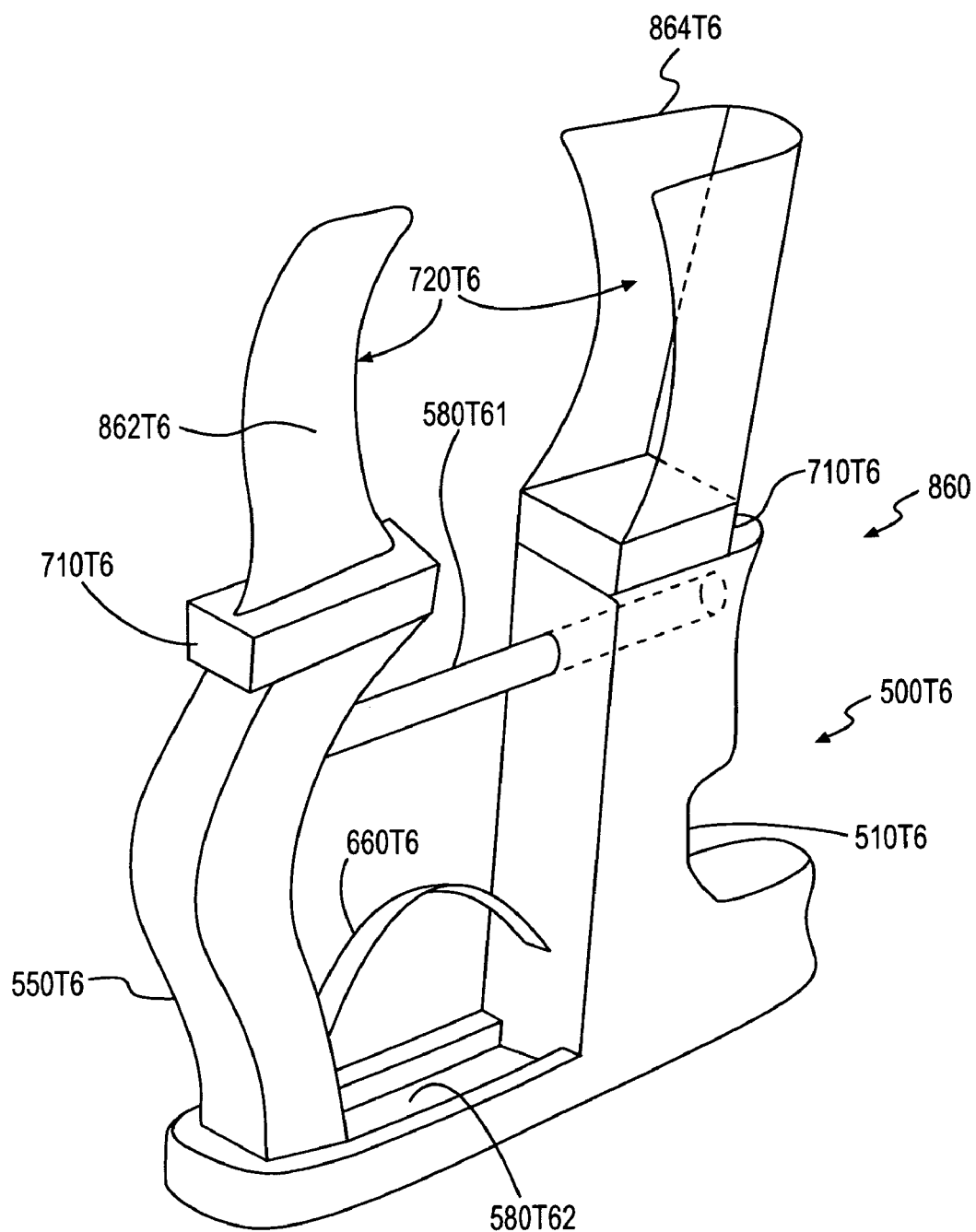
FIG. 12F illustrates an embodiment of a parallel handle of the present invention used to shuck clams.

FIG. 12F illustrates an example of a bivalve or clam shucker pliers-type tool 860 with a parallel handle 500T6 similar to parallel handles 500A and 500I. The parallel handle 500T6 of bivalve or clam shucker pliers-type tool 860 has a proximal moving member 510T6 and a distal moving member 550T6 and has two track guide members 580T61 and 580T62 with a spring 660T6. The bivalve or clam shucker pliers-type tool 860 has two opposing facing parts 720T6 at the working ends 710T6. One of the working ends 710T6 has a single blade 862T6 attached to the distal moving member 550T6 that cuts and pries a bivalve shell or a clamshell open. The other working end 710T6 has a double retaining stop 864T6 attached to a proximal moving member 510T6 for retaining a shell in position while the blade 862T6 of the bivalve or clam shucker pliers-type tool 860 cuts and pries open the shell of the clam or bivalve.

Figure 12G:
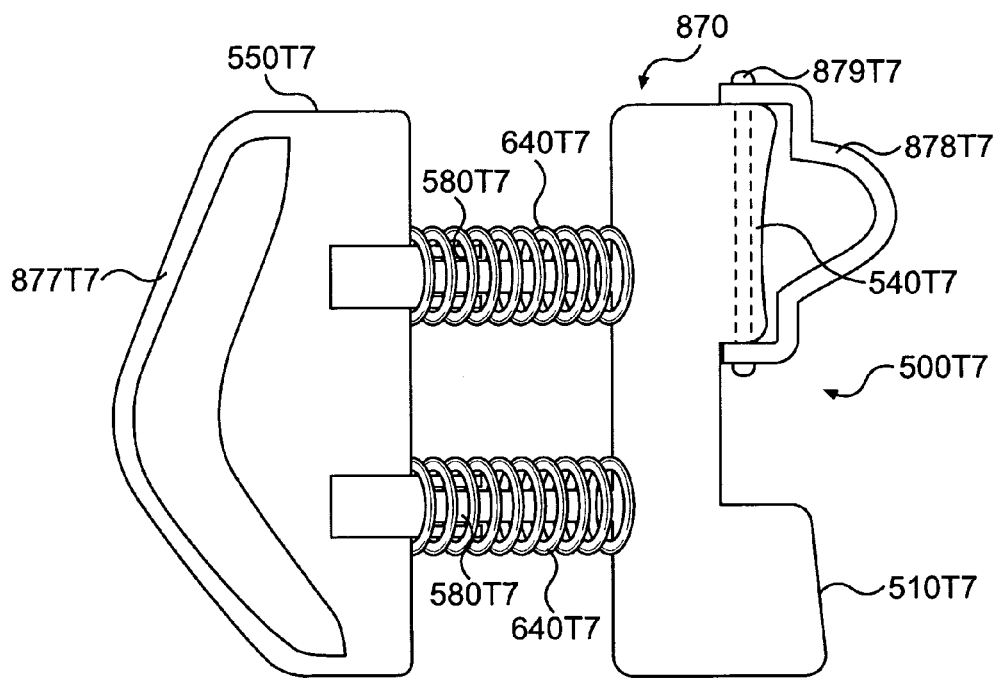
FIG. 12G illustrates an embodiment of a parallel handle of the present invention used as a hand exerciser.

FIG. 12G illustrates and a hand exerciser 870 with a parallel handle 500T7 similar to parallel handles 500E and 500I. The parallel handle 500T7 of hand exerciser 870 has a proximal moving member 510T7 and a distal moving member 550T7 and has two telescoping guide members 580T7 each with a coil spring 640T7. The coil springs 640T7 can be interchangeable so as to be of varying lengths and compressibility. The parallel handle 500T7 of the hand exerciser 870 has a distal ring 877T7 on the distal moving member 550T7 for receiving the long fingers 200 and has a proximal ring 878T7 on the proximal moving member 510T7 for receiving the thumb 201 of the hand 100. Such rings 877T7, 878T7 assist with spreading of the hand 100 against resistance of expansion provided by the guide members 580T7 with the coil springs 640T7. The proximal ring 878T7 can be attached to a shaft 879T7 in the radial section 540T7 of the proximal moving member 510T7 so the proximal ring 878T7 can rotate for use with either a right hand 100 or a left hand 100.

Figure 12H:
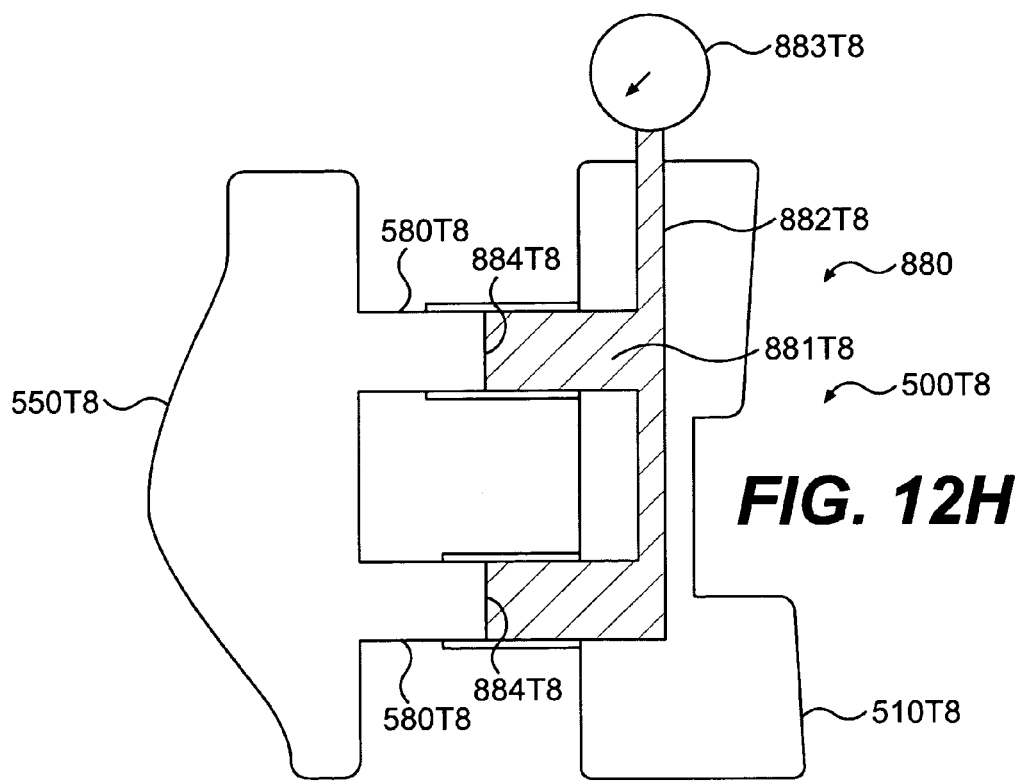
FIG. 12H illustrates an embodiment of a parallel handle of the present invention used as a hand dynamometer.

FIG. 12H illustrates an example of a dynamometer apparatus 880 for evaluating grip strength of the hand 100 with a parallel handle 500T8 similar to parallel handle 500E. The parallel handle 500T8 of dynamometer apparatus 880 has a proximal moving member 510T8 and a distal moving member 550T8 and has two telescoping guide members 580T8.

The dynamometer apparatus 880 can have hydraulic fluid 881T8 in a system of tubes 882T8 within the guide members 580T8 and within the proximal moving member 510T8. The hydraulic fluid 881T8 in the system of tubes 882T8 actuates a meter 883T8 attached to the proximal moving member 510T8. The distal moving member 550T8 of a dynamometer apparatus 880 moves plungers or pistons 884T8 in telescoping guide members 580T8. In turn the meter 883T8 responds to a change of pressure transmitted to the hydraulic fluid 881T8 within the system of tubes 882T8 to measure grip strength.

Figure 12I:
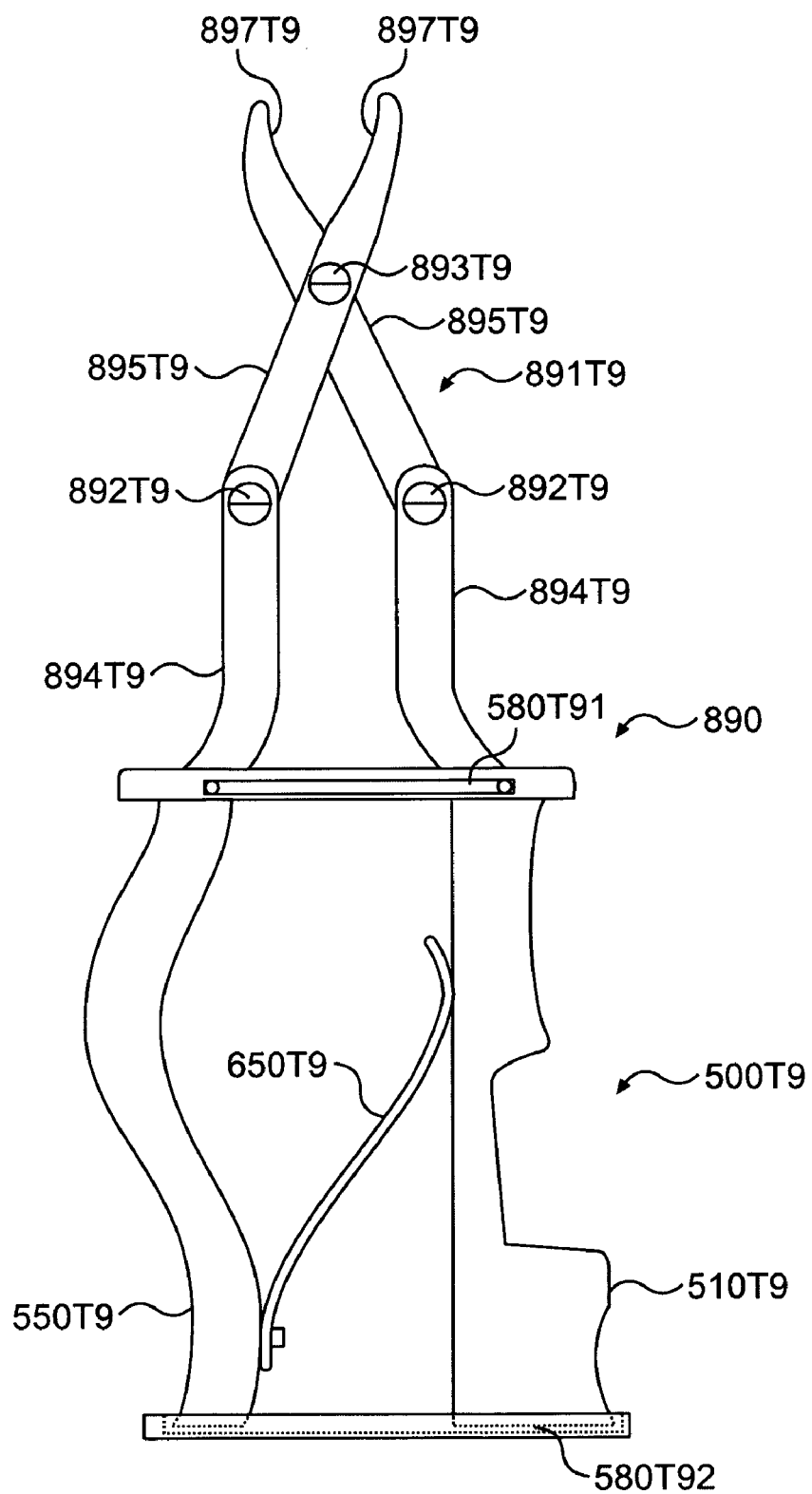
FIG. 12I illustrates an embodiment of a parallel handle of the present invention with a double action hinged mechanism used to cut branches or rongeur bone.

FIG. 12I illustrates an example of a double action implement 890 with a parallel handle 500T9 similar to parallel handle 500A. The parallel handle 500T9 of double action implement 890 has a proximal moving member 510T9 and a distal moving member 550T9 and has two guide members 580T91 and 580T92 with a leaf spring 650T9. The double action implement 890 translates the open and close movement of the parallel handle 500T9 to a scissors-style tool 891T9 of the double action implement 890. The scissors-style tool 891T9 has a pair of supports 894T9 that respectively attach to the proximal moving member 510T9 and the distal moving member 550T9 at one end and to a corresponding pair of proximal hinges 892T9 at the other end. The pair of proximal hinges 892T9 also respectively connect the pair of supports 894T9 to working ends 895T9. A single distal hinge 893T9 movably connects the working ends 895T9. The working ends 895T9 each respectively have an opposing facing part 897T9. Reducing and expanding the distance between the proximal moving member 510T9 and the distal moving member 550T9 of the double action implement 890 actuate the working ends 895T9 to respectively come together and move apart to rongeur bone, snip branches and perform other cutting, grasping or pinching functions.

Figure 12J:
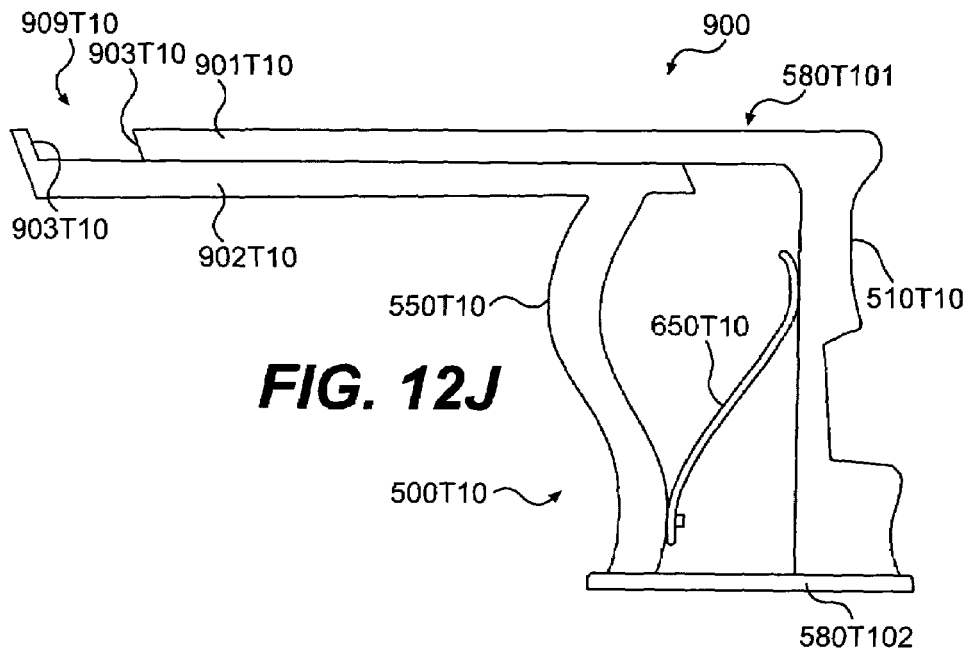
FIG. 12J illustrates an embodiment of a parallel handle of the present invention used as a Kerrison rongeur for spine surgery.

FIG. 12J illustrates an example of a Kerrison-type surgical apparatus 900 with a parallel handle 500T10 similar to parallel handle 500A. The parallel handle 500T10 of the Kerrison-type surgical apparatus 900 has a proximal moving member 510T10 and a distal moving member 550T10 and has two guide members 580T101 and 580T102 with a leaf spring 650T10. The working end 909T10 of the Kerrison-type surgical apparatus 900 is comprised of an upper sliding member 901T10 and a lower sliding member 902T10. The upper sliding member 901T10 and the lower sliding member 902T10 also form one of the guide members 580T101. The proximal moving member 510T10 of the Kerrison-type apparatus 900 can be attached to or integrally formed with the upper sliding member 901T10. The distal moving member 550T10 can be attached or integrally formed with to the lower sliding member 902T10. Alternatively, the proximal moving member 510T10 of the Kerrison-type apparatus 900 can be attached to or integrally formed with the lower sliding member 902T10, and the distal moving member 550T10 can be attached or integrally formed with to the upper sliding member 901T10. Movement of one or both of the sliding members 901T10 and 902T10 by moving the parallel handle 500T10 causes the biting ends 903T10 of the working end 909T10 to engage with an object or a part of the body for grasping, pinching or cutting, such as to nibble bone during spinal surgery, for example.

Figure 12K:
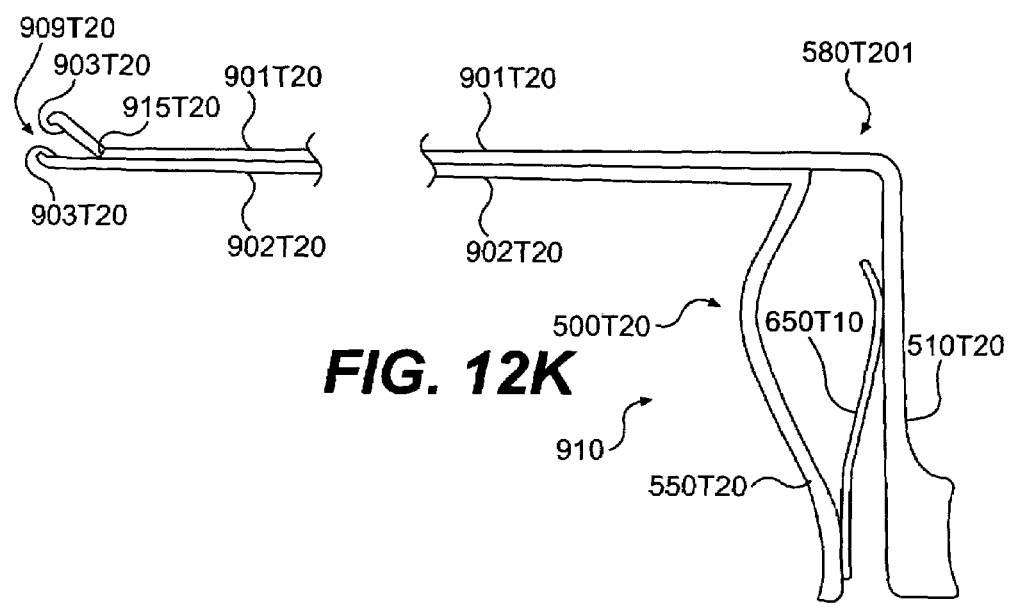
FIG. 12K illustrates an embodiment of a parallel handle of the present invention used for endoscopic surgery.

FIG. 12K illustrates an example of an endoscopic-type surgical apparatus 910 with a parallel handle 500T20 similar to parallel handles 500F and 500I. The parallel handle 500T20 of the endoscopic-type surgical apparatus 910 has a proximal moving member 510T20 and a distal moving member 550T20 and has one guide member 580T201 and a leaf spring 650T10. The working end 909T20 of the endoscopic-type surgical apparatus 910 is comprised of an upper sliding member 901T20 and a lower sliding member 902T20, and a hinge 915T20 connects the biting ends 903T20 of the working end 909T20. The upper sliding member 901T20 and the lower sliding member 902T20 also form the guide member 580T201. The proximal moving member 510T20 of the endoscopic-type surgical apparatus 910 can be attached to or integrally formed with the upper sliding member 901T20. The distal moving member 550T20 can be attached or integrally formed with to the lower sliding member 902T20. Alternatively, the proximal moving member 510T20 of the endoscopic-type surgical apparatus 910 can be attached to or integrally formed with the lower sliding member 902T20, and the distal moving member 550T20 can be attached or integrally formed with to the upper sliding member 901T20. Movement of one or both of the sliding members 901T20 and 902T20 by moving the parallel handle 500T20 causes the biting ends 903T20 of the working end 909T20 to engage with an object or a part of the body for grasping, pinching or cutting, such as to remove tissue during surgery, for example.

Figure 12L:
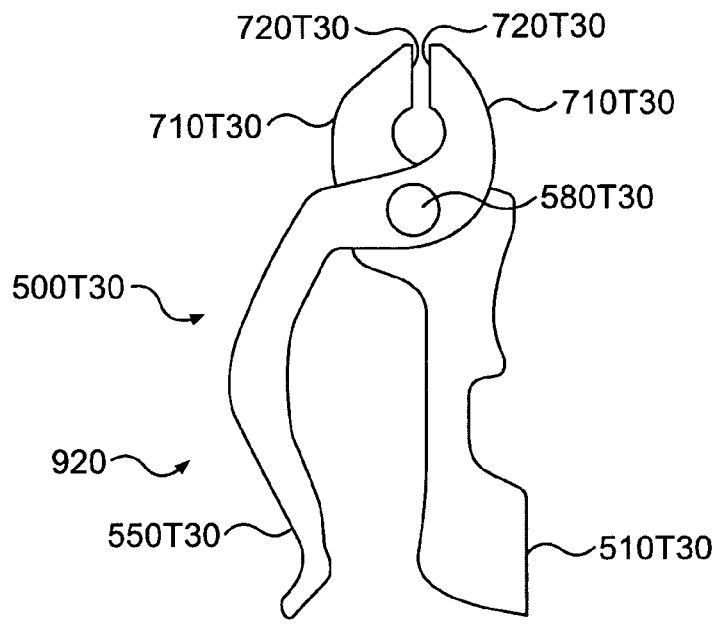
FIG. 12L illustrates an embodiment of a parallel handle of the present invention with a hinge to use as pliers.

FIG. 12L illustrates an example of a pliers-type tool 920 with a parallel handle 500T30 similar to parallel handle 500A. The parallel handle 500T30 of pliers-type tool 920 has a proximal moving member 510T30 and a distal moving member 550T30 and has a guide member 580T30. However, the guide member 580T30 functions as a hinge joining the proximal moving member 510T30 and the distal moving member 550T30. The pliers-type tool 920 has two opposing facing parts 720T30 at the working ends 710T30. The working ends 710T30 can include a pliers-type tool or a cutting tool, for example. The working ends 710T30 extend from the proximal moving member 510T30 and the distal moving member 550T30.

Figure 12M:
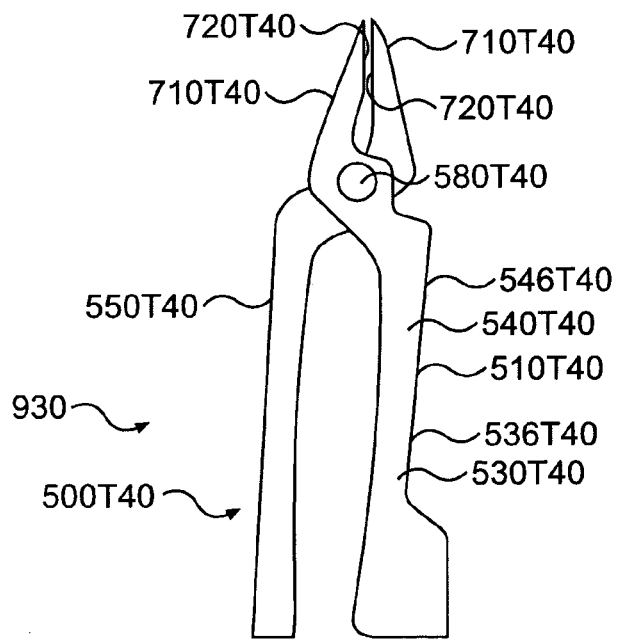
FIG. 12M illustrates an embodiment of a parallel handle of the present invention with a hinge to use as fine pliers.

FIG. 12M illustrates an example of a pliers-type tool 930 with a parallel handle 500T40 similar to parallel handle 500A. The parallel handle 500T40 of pliers-type tool 930 has a proximal moving member 510T40 and a distal moving member 550T40 and has a guide member 580T40. However, the guide member 580T40 functions as a hinge joining the proximal moving member 510T40 and the distal moving member 550T40. The pliers-type tool 930 has two opposing facing parts 720T40 at the working ends 710T40. The working ends 710T40 can include a pliers-type tool or a cutting tool, for example. The working ends 710T40 extend from the proximal moving member 510T40 and the distal moving member 550T40. Further, FIG. 12M illustrates an example where, as discussed with respect to FIG. 10B, the distance D' can vary so to be equal to or less than distance C' and still avoid contacting or putting undue pressure on the "carpal tunnel zone" CTZ. In FIG. 12M the radial surface 546T40 of the radial section 540T40 and the middle surface 536T40 of the middle section 530T40 are in linear alignment such that the distance D' is less than the distance C', and the middle surface 536T40 of the middle section 530T40 of the proximal moving member 510T40 avoids contacting or putting undue pressure on the "carpal tunnel zone" CTZ.

Figure 12P:
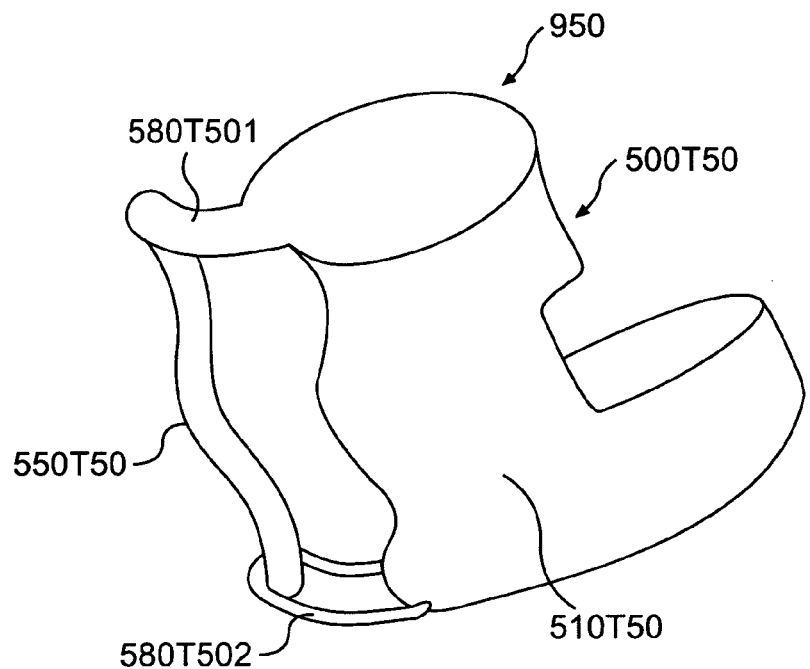
Figure 12Q:
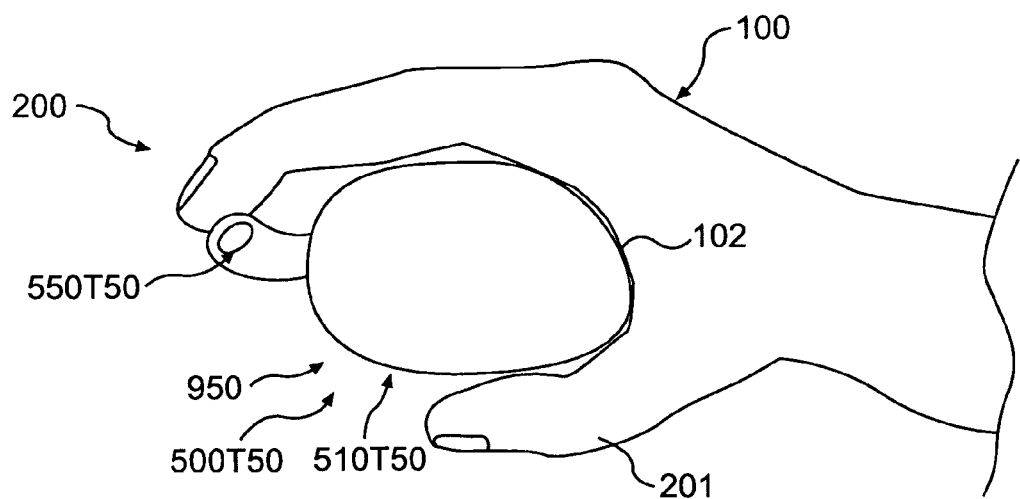

FIGS. 12N through 12S2 illustrate an example of a parallel handle control mechanism 950 that incorporates a parallel handle 500T50, similar to parallel handles 500A and 500G. Parallel handle control mechanism 950 can be used for mechanical or electronic control functions of devices, such as, brakes, valves, pumps, clamps, motors, and steering devices and for various other mechanical, electrical or electronic control functions. FIG. 12N illustrates a profile or side view of the parallel handle control mechanism 950, with FIG. 12O illustrating the distal (front) view of the parallel handle control mechanism 950, with FIG. 12P illustrating a perspective view of the parallel handle control mechanism 950 and FIG. 12Q illustrating a perspective view of the hand 100 engaging the handle control handle mechanism 950. FIG. 12R is similar to FIG. 12N except that it further incorporates a control mechanism, such as for actuating and releasing a brake of a vehicle. FIG. 12S1 illustrates an exploded view of a hinged control mechanism used with the parallel handle control mechanism 950 of FIG. 12N, and FIG. 12S2 illustrates an exploded view of an electrical or electronic control mechanism used with the parallel handle control mechanism 950 of FIG. 12N.

Continuing with reference to FIGS. 12N through 12S2, the parallel handle 500T50 of the parallel handle control mechanism 950 has a proximal moving member 510T50 and a distal moving member 550T50 and has two guide members 580T501 and 580T502 with FIGS. 12R and 12S including a coil spring 650T50 within the guide member 580T502. FIG. 12Q illustrates a hand 100 engaging the parallel handle 500T50 of the parallel handle control mechanism 950 with the long fingers 200 engaging the distal moving member 550T50 and with the palm 102 and the thumb 201 engaging the proximal moving member 510T50.

Referring to FIGS. 12R through 12S2 various control mechanisms are illustrated for mechanical, electrical, electronic or electromechanical for control of various devices and functions. In FIG. 12R, the guide member 580T502 includes coil spring 650T501 for biasing the movement of the distal moving member 550T50 when utilized for controlling a device or function.

FIG. 12S1 illustrates an exploded view of a hinged control mechanism 1000 associated with the guide member 580T501 and with the distal moving member 550T50. The hinged control mechanism 1000 includes an engaging member 1001 associated the distal moving member 550T50 and a pivoting control member 1002. The pivoting control member 1002 includes a proximal arm 1003, a distal arm 1005 and a pivot member or hinge 1004. The pivot member or hinge 1004 permits movement of the distal arm 1005 in response to movement of the proximal arm 1003 when the proximal arm 1003 is moved by the engaging member 1001 in response to movement of the distal moving member 550T50. Engaging of the proximal arm 1003 by the engaging member 1001 permits selective movement or positioning of the distal arm 1005 of the pivoting control member 1002 which actuates control line 1006 for corresponding control of a device 1007.

FIG. 12S2 illustrates an exploded view of an electromechanical control mechanism 1100 associated with the guide member 580T501 and with the distal moving member 550T50. The electromechanical control mechanism 1100 includes an engaging member 1101 associated the distal moving member 550T50. The engaging member 1101 has a contact 1102 for selectively engaging with one or more actuating contacts 1103a, 1103b, 1103c . . . 1103n for corresponding control of a device 1107 when contact 1102 is selectively positioned in engaging relation with one or more actuating contacts 1103a, 1103b, 1103c . . . 1103n by selective movement of the distal moving member 550T50. Selectively engaging one or more of the actuating contacts 1103a, 1103b, 1103c . . . 1103n by the contact 1102 actuates a corresponding control signal CS through line 1104 for corresponding control of the device 1107.

Other applications for tools using a parallel handle 500 based on the method for designing parallel handles of the present invention include handles to actuate or control various mechanical or electronic control functions of devices, such as, brakes, valves, pumps, clamps, motors, and steering devices and for various other mechanical, electrical or electronic control functions. Furthermore, the proximal moving member 510 and distal moving member 550 can have multiple interchangeable working ends. Like a jackknife, such a handle can also have multiple working tools inside each proximal moving member 510 and distal moving member 550 of a parallel handle 500 based on the method for designing parallel handles of the present invention. This list of applications is not comprehensive because there are many common tools that can be actuated by moving the long fingers 200 to and from the palm 102 of the hand.

What is claimed is:

1. A handle for use with a human hand, comprising:
 a proximal part having a first elongated body, the proximal part including a radial section, a middle section and an ulnar section forming a proximal side and a distal side of the first elongated body,
  with the radial section of the proximal part having a radial surface on the proximal side of the first elongated body for engaging a portion of the palmar surface of the hand;
  with the middle section of the proximal part adjoining the radial section of the proximal part and having a middle surface on the proximal side of the first elongated body that avoids placing undue pressure on a surface of the hand located over the carpal tunnel;
  with the ulnar section of the proximal part adjoining the middle section of the proximal part and having an ulnar surface on the proximal side of the first elongated body for engaging a portion of the palmar surface of the hand; and
  with a connecting surface of the proximal part on the proximal side of the first elongated body that connects, on the proximal side of the first elongated body, the middle surface of the middle section of the proximal part to the ulnar surface of the ulnar section of the proximal part, and with the connecting surface extending proximally for a distance from a position at one end of the middle surface of the middle section of the proximal part to a position at one end of the ulnar surface of the ulnar section of the proximal part;

a distal part having a second elongated body, the distal part for receiving at least a portion of one or more fingers of the hand, and the distal part including a radial section, a middle section and an ulnar section forming a proximal side and a distal side of the second elongated body, with the middle section of the distal part adjoining the radial section of the distal part and the ulnar section of the distal part adjoining the middle section of the distal part; and at least one guide member that engages at least one of the proximal part and the distal part for guiding the movement of at least one of the proximal part and distal part, wherein the distance that the connecting surface extends is at least of a length whereby the ulnar surface of the ulnar section of the proximal part extends beyond the middle surface of the middle section of the proximal part on the proximal side of the first elongated body, and whereby the handle is positioned within the hand without placing substantial pressure on the surface of the hand located over the carpal tunnel.

2. The handle according to claim 1, wherein the proximal part comprises a proximal moving member and the distal part comprises a distal moving member.

3. The handle according to claim 2, wherein the proximal moving member includes a proximal surface and a distal surface and the distal moving member includes a proximal surface and a distal surface.

4. The handle according to claim 3, wherein a portion of the proximal surface of the proximal moving member corresponding to the middle surface of the middle section of the proximal part avoids placing undue pressure on a surface of the hand located over the carpal tunnel.

5. The handle according to claim 3, wherein a portion of the proximal surface of the proximal moving member corresponding to the middle surface of the middle section of the proximal part avoids contacting a surface of the hand located over the carpal tunnel.

6. The handle according to claim 1, wherein the length of the proximal part of the handle between a radial end of the radial section of the proximal part and an ulnar end of the ulnar section of the proximal part is in a range of from about 7 cm to about 10 cm, based upon the width of the palm taken across the metacarpal-phalangeal (MP) joints of the hand.

7. The handle according to claim 2, wherein the at least one guide member that engages at least one of the proximal moving member and the distal moving member at least one of guides the movement of the proximal moving member relative to the distal moving member, guides the movement of the distal moving member relative to the proximal moving member, or guides the movement of the proximal moving member and the distal moving member relative to each other.

8. The handle according to claim 7, wherein the at least one guide member aligns the proximal moving member and the distal moving member for parallel movement.

9. The handle according to claim 7, wherein the at least one guide member comprises a hinge for pivotal movement of at least one of the proximal moving member and the distal moving member.

10. The handle according to claim 9, further comprising a working end on at least one of the proximal moving member and the distal moving member.

11. The handle according to claim 9, further comprising a working end on both the proximal moving member and the distal moving member.

12. The handle according to claim 11, wherein the working end on both the proximal moving member and the distal moving member comprise a pliers-type tool.

13. The handle according to claim 11, wherein the working end on both the proximal moving member and the distal moving member comprise a cutting tool.

14. The handle according to claim 8, further comprising a working end on at least one of the proximal moving member and the distal moving member.

15. The handle according to claim 8, further comprising a working end on both the proximal moving member and the distal moving member.

16. The handle according to claim 15, wherein the working end on both the proximal moving member and the distal moving member comprise a pliers-type tool.

17. The handle according to claim 15, wherein the working end on both the proximal moving member and the distal moving member comprise a cutting tool.

18. The handle according to claim 8, wherein the at least one guide member includes a control mechanism for control of mechanical, electrical or electronic functions.

19. The handle according to claim 18, wherein the control mechanism is for control of a braking system.

20. The handle according to claim 18, wherein the braking system is a braking system for a vehicle.

21. The handle according to claim 18, wherein the vehicle comprises a bicycle, a motorcycle or a motor vehicle.

22. The handle according to claim 18, wherein the control mechanism is for control of a device.

23. The handle according to claim 8, wherein the handle comprises a pair of opposing guide members.

24. The handle according to claim 23, further comprising a spring that engages the proximal moving member and the distal moving member for biasing the movement of at least one of the distal moving member and the proximal moving member.

25. The handle according to claim 23, further comprising a spring associated with each of the pair of opposing guide members for biasing the movement of at least one of the distal moving member and the proximal moving member.

26. The handle according to claim 7, further comprising a spring that engages the proximal moving member and the distal moving member for biasing the movement of at least one of the distal moving member and the proximal moving member.

27. The handle according to claim 7, wherein the proximal moving member includes a proximal ring member for receiving the thumb of a hand.

28. The handle according to claim 27, further comprising a spring that engages the proximal moving member and the distal moving member for biasing the movement of at least one of the distal moving member and the proximal moving member.

29. The handle according to claim 7, wherein the distal moving member includes a distal ring member for receiving at least one of the fingers of a hand.

30. The handle according to claim 29, further comprising a spring that engages the proximal moving member and the distal moving member for biasing the movement of at least one of the distal moving member and the proximal moving member.

31. The handle according to claim 7, wherein the proximal moving member includes a proximal ring member for receiving the thumb of a hand and the distal moving member includes a distal ring member for receiving at least one of the fingers of a hand.

32. The handle according to claim 31, further comprising a spring that engages the proximal moving member and the distal moving member for biasing the movement of at least one of the distal moving member and the proximal moving member.

33. The handle according to claim 7, wherein the proximal moving member and the distal moving member comprise a squeezing device.

34. The handle according to claim 33, wherein the squeezing device comprises a hand exerciser.

35. The handle according to claim 33, wherein the squeezing device comprises a control mechanism for control of mechanical, electrical or electronic functions.

36. The handle according to claim 35, wherein the control mechanism comprises a control mechanism for a braking system for a vehicle.

37. The handle according to claim 35, wherein the control mechanism comprises a control mechanism for a device.

38. The handle according to claim 7, wherein the proximal moving member and the distal moving member are hinged at one end for use as a squeezing device.

39. An apparatus for use with a human hand, comprising:
a proximal part having a first elongated body, the proximal part including a radial section, a middle section and an ulnar section forming a proximal side and a distal side of the first elongated body,
  with the radial section of the proximal part having a radial surface on the proximal side of the first elongated body for engaging a portion of the palmar surface of the hand;
  with the middle section of the proximal part adjoining the radial section of the proximal part and having a middle surface on the proximal side of the first elongated body that avoids placing undue pressure on a surface of the hand located over the carpal tunnel;
  with the ulnar section of the proximal part adjoining the middle section of the proximal part and having an ulnar surface on the proximal side of the first elongated body for engaging a portion of the palmar surface of the hand; and
  with a connecting surface of the proximal part on the proximal side of the first elongated body that connects, on the proximal side of the first elongated body, the middle surface of the middle section of the proximal part to the ulnar surface of the ulnar section of the proximal part, and with the connecting surface extending proximally for a distance from a position at one end of the middle surface of the middle section of the proximal part to a position at one end of the ulnar surface of the ulnar section of the proximal part;
a distal part having a second elongated body, the distal part for receiving at least a portion of one or more fingers of the hand, and the distal part including a radial section, a middle section and an ulnar section forming a proximal side and a distal side of the second elongated body, with the middle section of the distal part adjoining the radial section of the distal part and the ulnar section of the distal part adjoining the middle section of the distal part; and
at least one guide member that engages at least one of the proximal part and the distal part for guiding the movement of at least one of the proximal part and distal part, wherein the distance that the connecting surface extends is at least of a length whereby the ulnar surface of the ulnar section of the proximal part extends beyond the middle surface of the middle section of the proximal part on the proximal side of the first elongated body, and whereby the apparatus is positioned within the hand without placing substantial pressure on the surface of the hand located over the carpal tunnel.

40. The apparatus according to claim 39, wherein the proximal part comprises a proximal moving member and the distal part comprises a distal moving member.

41. The apparatus according to claim 40, wherein the proximal moving member includes a proximal surface and a distal surface and the distal moving member includes a proximal surface and a distal surface.

42. The apparatus according to claim 41, wherein a portion of the proximal surface of the proximal moving member corresponding to the middle surface of the middle section of the proximal part avoids placing undue pressure on a surface of the hand located over the carpal tunnel.

43. The apparatus according to claim 41, wherein a portion of the proximal surface of the proximal moving member corresponding to the middle surface of the middle section of the proximal part avoids contacting a surface of the hand located over the carpal tunnel.

44. The apparatus according to claim 39, wherein the length of the apparatus between a radial end of the radial section of the proximal part and an ulnar end of the ulnar section of the proximal part is in a range of from about 7 cm to about 10 cm, based upon the width of the palm taken across the metacarpal-phalangeal (MP) joints of the hand.

45. The apparatus according to claim 40, wherein the at least one guide member that engages at least one of the proximal moving member and the distal moving member at least one of guides the movement of the proximal moving member relative to the distal moving member, guides the movement of the distal moving member relative to the proximal moving member, or guides the movement of the proximal moving member and the distal moving member relative to each other.

46. The apparatus according to claim 45, wherein the at least one guide member aligns the proximal moving member and the distal moving member for parallel movement.

47. The apparatus according to claim 45, wherein the at least one guide member comprises a hinge for pivotal movement of at least one of the proximal moving member and the distal moving member.

48. The apparatus according to claim 47, further comprising a working end on at least one of the proximal moving member and the distal moving member.

49. The apparatus according to claim 47, further comprising a working end on both the proximal moving member and the distal moving member.

50. The apparatus according to claim 49, wherein the working end on both the proximal moving member and the distal moving member comprise a pliers-type tool.

51. The apparatus according to claim 49, wherein the working end on both the proximal moving member and the distal moving member comprise a cutting tool.

52. The apparatus according to claim 46, further comprising a working end on at least one of the proximal moving member and the distal moving member.

53. The apparatus according to claim 46, further comprising a working end on both the proximal moving member and the distal moving member.

54. The apparatus according to claim 53, wherein the working end on both the proximal moving member and the distal moving member comprise a pliers-type tool.

55. The apparatus according to claim 53, wherein the working end on both the proximal moving member and the distal moving member comprise a cutting tool.

56. The apparatus according to claim 46, wherein the at least one guide member includes a control mechanism for control of mechanical, electrical or electronic functions.

57. The apparatus according to claim 56, wherein the control mechanism is for control of a braking system.

58. The apparatus according to claim 57, wherein the braking system is a braking system for a vehicle.

59. The apparatus according to claim 58, wherein the vehicle comprises a bicycle, a motorcycle or a motor vehicle.

60. The apparatus according to claim 56, wherein the control mechanism is for control of a device.

61. The apparatus according to claim 45, wherein the apparatus comprises a pair of opposing guide members.

62. The apparatus according to claim 61, further comprising a spring that engages the proximal moving member and the distal moving member for biasing the movement of at least one of the distal moving member and the proximal moving member.

63. The apparatus according to claim 61, further comprising a spring associated with each of the pair of opposing guide members for biasing the movement of at least one of the distal moving member and the proximal moving member.

64. The apparatus according to claim 45, further comprising a spring that engages the proximal moving member and the distal moving member for biasing the movement of at least one of the distal moving member and the proximal moving member.

65. The apparatus according to claim 45, wherein the proximal moving member includes a proximal ring member for receiving the thumb of a hand.

66. The apparatus according to claim 65, further comprising a spring that engages the proximal moving member and the distal moving member for biasing the movement of at least one of the distal moving member and the proximal moving member.

67. The apparatus according to claim 45, wherein the distal moving member includes a distal ring member for receiving at least one of the fingers of a hand.

68. The apparatus according to claim 67, further comprising a spring that engages the proximal moving member and the distal moving member for biasing the movement of at least one of the distal moving member and the proximal moving member.

69. The apparatus according to claim 45, wherein the proximal moving member includes a proximal ring member for receiving the thumb of a hand and the distal moving member includes a distal ring member for receiving at least one of the fingers of a hand.

70. The apparatus according to claim 69, further comprising a spring that engages the proximal moving member and the distal moving member for biasing the movement of at least one of the distal moving member and the proximal moving member.

71. The apparatus according to claim 45, wherein the proximal moving member and the distal moving member comprise a squeezing device.

72. The apparatus according to claim 71, wherein the squeezing device comprises a hand exerciser.

73. The apparatus according to claim 71, wherein the squeezing device comprises a control mechanism for control of mechanical, electrical or electronic functions.

74. The apparatus according to claim 73, wherein the control mechanism comprises a control mechanism for a braking system for a vehicle.

75. The apparatus according to claim 73, wherein the control mechanism comprises a control mechanism for a device.

76. The apparatus according to claim 45, wherein the proximal moving member and the distal moving member are hinged at one end for use as a squeezing device.

77. The handle according to claim 1, wherein the distance that the connecting surface extends is at least of a length whereby the ulnar surface of the ulnar section of the proximal part extends beyond the radial surface of the radial section of the proximal part on the proximal side of the first elongated body.

78. The handle according to claim 77, wherein, relative to the ulnar surface of the ulnar section of the proximal part on the proximal side of the first elongated body, the radial surface of the radial section of the proximal part extends proximally for a distance equal to or greater than a distance that the middle surface of the middle section of the proximal part extends proximally.

79. The handle according to claim 77, wherein, relative to the ulnar surface of the ulnar section of the proximal part on the proximal side of the first elongated body, the radial surface of the radial section of the proximal part extends proximally for a distance different from a distance that the middle surface of the middle section of the proximal part extends proximally.

80. The handle according to claim 1, wherein, relative to the ulnar surface of the ulnar section of the proximal part on the proximal side of the first elongated body, the radial surface of the radial section of the proximal part extends proximally for a distance equal to or greater than a distance that the middle surface of the middle section of the proximal part extends proximally.

81. The handle according to claim 1, wherein, relative to the ulnar surface of the ulnar section of the proximal part on the proximal side of the first elongated body, the radial surface of the radial section of the proximal part extends proximally for a distance different from a distance that the middle surface of the middle section of the proximal part extends proximally.

82. The handle according to claim 2, wherein at least one of the proximal moving member and the distal moving member comprises a receiving member and a replaceable moving member for selectively engaging the receiving member of the corresponding one of the proximal moving member or the distal moving member.

83. The handle according to claim 82, wherein the size or configuration of the replaceable moving member comprises a plurality of sizes or configurations.

84. The handle according to claim 83, wherein the size or configuration of the receiving member comprises a plurality of sizes or configurations.

85. The handle according to claim 82, wherein the size or configuration of the receiving member comprises a plurality of sizes or configurations.

86. The handle according to claim 82, further comprising a working end on at least one of the receiving member of the proximal member or the receiving member of the distal moving member.

87. The handle according to claim 86, where in the working end is for at least one of grasping, pinching or cutting.

88. The handle according to claim 7, further comprising a working end on at least one of the proximal moving member and the distal moving member.

89. The handle according to claim 88, wherein the working end is for at least one of grasping, pinching or cutting.

90. The handle according to claim 88, wherein the working end comprises a surgical tool.

91. The handle according to claim 90, wherein the surgical tool comprises one of a Kerrison-type surgical apparatus or an endoscopic-type surgical apparatus.

92. The apparatus according to claim 39, wherein the distance that the connecting surface extends is at least of a length whereby the ulnar surface of the ulnar section of the proximal part extends beyond the radial surface of the radial section of the proximal part on the proximal side of the first elongated body.

93. The apparatus according to claim 92, wherein, relative to the ulnar surface of the ulnar section of the proximal part on the proximal side of the first elongated body, the radial surface of the radial section of the proximal part extends proximally for a distance equal to or greater than a distance that the middle surface of the middle section of the proximal part extends proximally.

94. The apparatus according to claim 92, wherein, relative to the ulnar surface of the ulnar section of the proximal part on the proximal side of the first elongated body, the radial surface of the radial section of the proximal part extends proximally for a distance different from a distance that the middle surface of the middle section of the proximal part extends proximally.

95. The apparatus according to claim 39, wherein, relative to the ulnar surface of the ulnar section of the proximal part on the proximal side of the first elongated body, the radial surface of the radial section of the proximal part extends proximally for a distance equal to or greater than a distance that the middle surface of the middle section of the proximal part extends proximally.

96. The apparatus according to claim 39, wherein, relative to the ulnar surface of the ulnar section of the proximal part on the proximal side of the first elongated body, the radial surface of the radial section of the proximal part extends proximally for a distance different from a distance that the middle surface of the middle section of the proximal part extends proximally.

97. The apparatus according to claim 40, wherein at least one of the proximal moving member and the distal moving member comprises a receiving member and a replaceable moving member for selectively engaging the receiving member of the corresponding one of the proximal moving member or the distal moving member.

98. The apparatus according to claim 97, wherein the size or configuration of the replaceable moving member comprises a plurality of sizes or configurations.

99. The apparatus according to claim 98, wherein the size or configuration of the receiving member comprises a plurality of sizes or configurations.

100. The apparatus according to claim 97, wherein the size or configuration of the receiving member comprises a plurality of sizes or configurations.

101. The apparatus according to claim 97, further comprising a working end on at least one of the receiving member of the proximal member or the receiving member of the distal moving member.

102. The apparatus according to claim 101, where in the working end is for at least one of grasping, pinching or cutting.

103. The apparatus according to claim 45, further comprising a working end on at least one of the proximal moving member and the distal moving member.

104. The apparatus according to claim 103, wherein the working end is for at least one of grasping, pinching or cutting.

105. The apparatus according to claim 103, wherein the working end comprises a surgical tool.

106. The apparatus according to claim 105, wherein the surgical tool comprises one of a Kerrison-type surgical apparatus or an endoscopic-type surgical apparatus.

* * * * *